United States Patent [19]

Dubroeucq et al.

[11] Patent Number: 5,102,667
[45] Date of Patent: Apr. 7, 1992

[54] ISOINDOLONE DERIVATIVES, THEIR PREPARATION AND THE PHARMACEUTICAL COMPOSITIONS CONTAINING THEM

[75] Inventors: Marie-Christine Dubroeucq, Enghien Les Bains; Claude Moutonnier, Le Plessis Robinson; Jean-Francois Peyronel, Palaiseau; Michel Tabart, Paris; Alain Truchon, Lyons, all of France

[73] Assignee: Rhone-Poulenc Sante, Antony Cedex, France

[21] Appl. No.: 616,262

[22] Filed: Nov. 20, 1990

[30] Foreign Application Priority Data

Nov. 23, 1989 [FR]  France .................. 89 15406

[51] Int. Cl.$^5$ .................. A61K 9/14; A61K 31/40
[52] U.S. Cl. .................. 424/489; 424/436; 514/416; 514/885
[58] Field of Search .............. 514/415, 420, 412, 416, 514/414, 826, 885, 886; 548/452, 469, 470, 425; 424/489, 464, 436, 422, 59

[56]  References Cited
U.S. PATENT DOCUMENTS 3,890,347 6/1975 Middlemiss ............ 260/326.1
4,042,707 8/1977 Ripka ..................... 424/274

OTHER PUBLICATIONS

European Search Report, dated Feb. 8, 1990.

Primary Examiner—Thurman K. Page
Assistant Examiner—David J. Colucci
Attorney, Agent, or Firm—Morgan & Finnegan

[57]  ABSTRACT

This invention relates to isoindolone derivatives of general formula (I) in which the radicals R are hydrogen atoms or together form a bond, the symbols R' are phenyl radicals which can be substituted by a halogen atom or a methyl radical in position 2 or 3, X is an oxygen or sulphur atom or a radical N—$R_3$, $R_3$ being H, optionally substituted alkyl or dialkylamino, $R_1$ is optionally substituted phenyl or cyclohexadienyl, naphthyl or a heterocycle and $R_2$ is H, halogen, OH, alkyl, amionoalkyl, alkylaminoalkyl, dialkylaminoalkyl, alkoxy, alkylthio, acyloxy, carboxyl, optionally substituted alkoxycarbonyl, benzyloxycarbonyl, amino or acylamino, in their (3aR,7aR) forms or in the (3aRS,7aRS) form or their mixtures, and if appropriate their salts where such exist, and their preparation.

The new derivatives according to the invention are particularly valuable as antagonists of substance P.

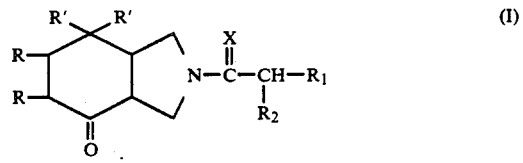

16 Claims, No Drawings

ISOINDOLONE DERIVATIVES, THEIR PREPARATION AND THE PHARMACEUTICAL COMPOSITIONS CONTAINING THEM

FIELD OF THE INVENTION

The present invention relates to new isoindolone derivatives of general formula:

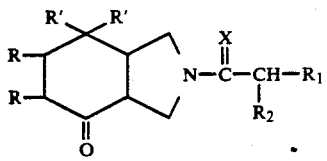

and their salts where such exist, which antagonize the effects of substance P and by virtue of this fact are particularly valuable in the therapy fields where this substance is known to be involved.

BACKGROUND OF THE INVENTION

Products derived from isoindole of general formula:

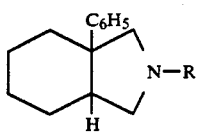

having an opiate activity had been described in U.S. Pat. No. 4,042,707. These products do not have any activity towards substance P.

To date, despite the research carried out and despite the interest raised [M. R. Hanley, TINS, (5) 139 (1982)], no product acting specifically on substance P and having a non-peptide structure had been discovered and it is for this reason that the isoindolone derivatives of formula (I) are of considerable value.

DETAILED DESCRIPTION OF THE INVENTION

In general formula (I):
the radicals R are identical and represent hydrogen atoms or together form a bond,
the symbols R' are identical and represent phenyl radicals optionally substituted by a halogen atom or by a methyl radical in position 2 or 3,
the symbol X represents an oxygen or sulphur atom or a radical N-$R_3$, for which $R_3$ is a hydrogen atom, an alkyl radical containing 1 to 12 carbon atoms and optionally substituted [by one or more carboxyl, dialkylamino, acylamino, alkoxycarbonyl, alkoxycarbonylamino, carbamoyl, alkylcarbamoyl or dialkylcarbamoyl (the alkyl portions of these radicals being able themselves to carry a dialkylamino or phenyl substituent by phenyl, substituted phenyl (substituted by halogen, alkyl, alkoxy or dialkylamino), naphthyl, thienyl, furyl, pyridyl or imidazolyl radicals] or a dialkylamino radical,
the symbol $R_1$ represents a phenyl radical optionally substituted by one or more halogen atoms or hydroxyl or alkyl radicals which can optionally be substituted (by halogen atoms or amino, alkylamino or dialkylamino radicals) or alkoxy or alkylthio radicals, which can optionally be substituted (by hydroxyl or dialkylamino radicals in which the alkyl parts can form, with the nitrogen atom to which they are attached, a 5- to 6-membered heterocycle which can contain another hetero-atom chosen from oxygen, sulphur or nitrogen, optionally substituted by an alkyl radical), or substituted by amino, alkylamino or dialkylamino radicals in which the alkyl parts can form, with the nitrogen atom to which they are attached, a heterocycle as defined above, or represents a cyclohexadienyl or naphthyl radical or a saturated or unsaturated monocyclic or polycyclic heterocycle containing 5 to 9 carbon atoms and one or more hetero-atoms chosen from oxygen, nitrogen or sulphur, and the symbol $R_2$ represents a hydrogen or halogen atom or a hydroxyl, alkyl, aminoalkyl, alkylaminoalkyl, dialkylaminoalkyl, alkoxy, alkylthio, acyloxy, carboxyl, alkoxycarbonyl, dialkylaminoalkoxycarbonyl, benzyloxycarbonyl, amino, acylamino or alkoxycarbonylamino radical.

It is understood that the abovementioned alkyl or acyl radicals contain 1 to 4 carbon atoms in a straight or branched chain.

When R' carries a halogen substituent, the latter can be chosen from chlorine or fluorine.

When $R_1$ or $R_3$ contains a halogen atom, the latter can be chosen from chlorine, bromine, fluorine or iodine.

When $R_1$ represents a saturated or unsaturated monocyclic or polycyclic heterocyclic radical it can be chosen, by way of example, from thienyl, furyl, pyridyl, dithiinyl, indolyl, isoindolyl, thiazolyl, isothiazolyl, oxazolyl, imidazolyl, pyrrolyl, triazolyl, thiadiazolyl, quinolyl, isoquinolyl or naphthyridinyl.

Moreover, the products of general formula (I) have various stereoisomer forms and it is understood that the isoindolone derivatives in the (3aR,7aR) form in the pure state, or in the form of a mixture of the cis forms (3aRS,7aRS), fall within the scope of the present invention. Moreover, when the symbol $R_2$ is other than a hydrogen atom, the substituted chain on the isoindolone has a chiral center and it is understood that the enantiomer forms and their mixtures also fall within the scope of the present invention.

According to the invention, the isoindolone derivatives of general formula (I) can be obtained by the action of the acid of general formula:

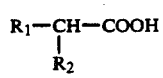

or of a reactive derivative of this acid, in which $R_1$ and $R_2$ are defined as above, on an isoindole derivative of general formula:

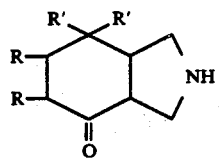

in which the symbols R and R' are defined as above, followed, if necessary, by the conversion of the amide obtained to the thioamide or to an amidine for which X represents a radical N-$R_3$, $R_3$ having the definition given above.

It is understood that the amino, alkylamino or carboxyl radicals contained in $R_1$ and/or $R_2$ are preferably protected beforehand. The protection is effected by any compatible group, the positioning and the removal of which have no effect on the remainder of the molecule. In particular, the methods described by T. W. Greene, Protective Groups in Organic Synthesis, by A. Wiley - Interscience Publication (1981), or by McOmie, Protective Groups in Organic Chemistry, Plenum Press (1973) are used.

By way of example, the amino or alkylamino groups can be protected by the following radicals: methoxycarbonyl, ethoxycarbonyl, t-butoxycarbonyl, allyloxycarbonyl, vinyloxycarbonyl, trichloroethoxycarbonyl, trichloroacetyl, trifluoroacetyl, chloroacetyl, trityl, benzhydryl, benzyl, allyl, formyl, acetyl, benzyloxycarbonyl or its substituted derivatives; and the acid groups can be protected by the following radicals: methyl, ethyl, t-butyl, benzyl, substituted benzyl or benzhydryl. Moreover, when $R_2$ represents a hydroxyl radical it is preferable to protect this radical beforehand. The protection is effected, for example, by an acetoxy, trialkylsilyl or benzyl radical, or in the form of a carbonate by a radical —COORa, in which Ra is an alkyl or benzyl radical.

When the condensation of the product of general formula (II) in its acid form (in which, if necessary, the amino, alkylamino, carboxyl and/or hydroxyl substituents have been protected beforehand) is carried out, the reaction is generally carried out in the presence of a condensing agent such as a carbodiimide [for example dicyclohexylcarbodiimide or 1-(3-dimethylaminopropyl)-3-ethylcarbodiimide], N,N'-carbonyldiimidazole or 2-ethoxy-1-ethoxycarbonyl-1,2-dihydroquinoline, in an organic solvent such as a chlorinated solvent (dichloromethane, dichloroethane or chloroform, for example), an ether (tetrahydrofuran or dioxane, for example), an ester (ethyl acetate, for example), an amide (dimethylacetamide or dimethylformamide, for example), a nitrile (acetonitrile, for example) or a ketone (acetone, for example) or in an aromatic hydrocarbon, such as toluene, for example, at a temperature of between −20° and 40° C. and, if necessary, the product obtained is then converted to a thioamide or an amidine and, if necessary, the protective radicals are removed.

When the condensation of a reactive derivative of the acid of general formula (II) is carried out, the reaction is advantageously carried out by means of an acid chloride, an anhydride, a mixed anhydride or a reactive ester in which the ester radical is a succinimido, 1-benzotriazolyl, 4-nitrophenyl, 2,4-dinitrophenyl, pentachlorophenyl or phthalimido radical. The reaction generally takes place at a temperature of between −40° and +40° C., in an organic solvent, such as a chlorinated solvent (dichloromethane, dichloroethane or chloroform, for example), an ether (tetrahydrofuran or dioxane, for example), an amide (dimethylacetamide or dimethylformamide, for example) or a ketone (acetone, for example) or in a mixture of these solvents, in the presence of an acid acceptor, such as a nitrogen-containing organic base, such as, for example, pyridine, dimethylaminopyridine, N-methylmorpholine or a trialkylamine (in particular triethylamine) or such as an epoxide (propylene oxide, for example) or a carbodiimide, or in an aqueous/organic medium, in the presence of an alkaline condensing agent such as sodium bicarbonate, and, if necessary, the amide obtained is converted to a thioamide or to an amidine as defined above.

The conversion of the amide of general formula (I) to a thioamide is effected by any thionation method which does not alter the remainder of the molecule.

In particular, the reaction is carried out by the action of Lawesson's reagent [2,4-bis(4-methoxyphenyl)-2,4-dithioxo-1,3,2,4-dithiadiphosphetane] or by the action of phosphorus pentasulphide, in an organic solvent, such as an ether (tetrahydrofuran, 1,2-dimethoxyethane or dioxane, for example) or an aromatic hydrocarbon (toluene, for example), at a temperature between 0° C. and the reflux temperature of the reaction mixture.

The conversion of the amide of general formula (I) to an amidine for which X is a radical N-$R_3$ takes place, either directly or via the corresponding thioamide, by preparing the isoindolium derivative of general formula:

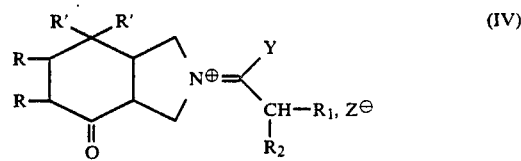

(IV)

in which R, R', $R_1$ and $R_2$ are defined as above and either Y represents a chlorine atom or a methoxy or ethoxy radical and $Z^-$ represents a chloride, tetrafluoborate, fluorosulphonate, trifluoromethylsulphonate, methylsulphate or ethylsulphate ion or Y represents a chlorine atom or a methylthio, ethylthio, benzylthio or alkoxycarbonylmethylthio radical and $Z^-$ is defined as above or represents an iodide or bromide ion, and then subjecting this to the action of an amine of general formula:

$R_3$-$NH_2$ (V)

in which $R_3$ is defined as above.

The preparation of the isoindolium derivative of general formula (IV) in which Y is a chlorine atom or a methoxy or ethoxy radical takes place by the action of a reagent such as phosgene, phosphorus oxychloride, phosphorus pentachloride, thionyl chloride, oxalyl chloride, trichloromethyl chloroformate, triethyl(or trimethyl)oxonium tetrafluoborate, methyl(or ethyl) triflate, methyl(or ethyl) fluorosulphonate or methyl(or ethyl) sulphate. The preparation of the isoindolium derivative of general formula (IV) in which Y is a chlorine atom or a methyl(or ethyl)thio, benzylthio or alkoxycarbonylmethylthio radical takes place using the isoindolone derivative of general formula (I) in which X is a sulphur atom as the starting material, by the action of a reagent such as mentioned above or by the action of methyl, ethyl or benzyl bromide or iodide. The reaction takes place in a chlorinated solvent (dichloromethane or dichloroethane, for example) or in an aromatic hydrocarbon (toluene, for example), at a temperature between 0° C. and the reflux temperature of the reaction mixture. When the reaction is carried out using the thioamide of general formula (I) as starting material, it is also possible to use solvents such as ethers, ketones, esters or nitriles. The action of the amine of general formula (V) on the derivative of general formula (IV) takes place in an anhydrous organic solvent, such as a chlorinated solvent (dichloromethane or dichloroethane, for example), in an alcohol/chlorinated solvent mixture, in an ether (tetrahydrofuran, for example), in an ester (for example ethyl acetate), in an aromatic solvent (toluene, for example) or in a mixture of these solvents, at a temperature between −20° C. and the reflux temperature of the reaction mixture.

It is not essential to have isolated the isoindolium derivative of general formula (IV) in order to use it in this reaction.

According to the invention, the isoindolone derivatives of general formula (I) in which $R_1$ and $R_2$ are defined as above, with the exception of representing or carrying hydroxyl, amino, alkylamino, dialkylamino or carboxyl substituents, and R, R', $R_3$ and X are defined as above, can also be obtained from a cyclohexenone derivative of general formula:

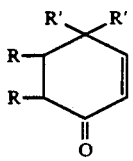
(VI)

in which R and R' are defined as above, by the action of 1,3,5-tris-trimethylsilylmethyl-1,3,5-triazine and an acid fluoride of general formula:

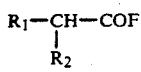
(VII)

in which $R_1$ and $R_2$ are defined as above, followed, if necessary, by the conversion of the amide obtained to a thioamide or to an amidine for which X represents a radical N-$R_3$ having the definition given above. The reaction generally takes place in an organic solvent, such as a chlorinated solvent (dichloroethane or trichloroethane, for example) or in an aromatic hydrocarbon (toluene or xylene, for example), at a temperature between 80° C. and the reflux temperature of the reaction mixture.

The conversion of the amide to the thioamide or to the amidine takes place in accordance with the methods described above.

According to the invention, the isoindolone derivatives of general formula (I) for which the symbol $R_1$ is an alkoxyphenyl radical in which the alkyl part is substituted or unsubstituted and the symbol $R_2$ is other than a hydroxyl radical can also be prepared from an isoindole derivative of general formula (I) for which $R_1$ is a hydroxyphenyl radical, by the action, in a basic medium, of the corresponding halogenated derivative, of general formula:

Hal-$R_4$ (VIII)

in which Hal is a halogen atom and $R_4$ is an alkyl radical optionally substituted by a hydroxyl radical, or dialkylamino in which the alkyl parts can optionally form, with the nitrogen atom to which they are attached, a heterocycle as defined in general formula (I).

The reaction generally takes place in the presence of a base, such as a hydride, an alkali metal hydroxide, an alkali metal alcoholate or an alkali metal carbonate, in an organic solvent, such as an amide (dimethylformamide, for example), an aromatic hydrocarbon (toluene, for example) or a ketone (butanone, for example) or in a mixture of these solvents, at a temperature between 20° C. and the reflux temperature of the reaction mixture.

When the radical $R_4$ carries a hydroxyl substituent it is understood that the latter is protected beforehand. The protection and the removal of the protective radical takes place in accordance with the methods described above.

According to the invention, isoindolone derivatives of general formula (I) for which X is a radical N-$R_3$ can also be obtained from the isoindolone derivative of general formula (III) by the action of a product of general formula:

(IX)

optionally in the form of a salt, in which $R_1$, $R_2$ and $R_3$ are defined as above and $R_5$ represents an alkoxy radical containing 1 to 4 carbon atoms in a straight or branched chain or a methylthio, ethylthio, benzylthio or alkoxycarbonylmethylthio radical, or, if $R_3$ is other than a hydrogen atom, $R_5$ represents an acyloxy radical containing 1 to 4 carbon atoms or a chlorine atom.

The reaction is carried out using the derivative of general formula (IX), optionally prepared in situ, in an organic solvent, such as a chlorinated solvent (dichloromethane or dichloroethane, for example), an ether (tetrahydrofuran, for example), an aromatic hydrocarbon (toluene, for example) or a nitrile, for example acetonitrile, at a temperature between 0° C. and the reflux temperature of the reaction mixture.

It is understood that if the radicals $R_1$, $R_2$ and/or $R_3$ of the product of general formula (IX) carry substituents which are able to interfere with the reaction, said substituents must be protected beforehand.

The acids of general formula (II) can be prepared by the methods described below in the examples, or by analogy with these methods.

The isoindole derivative of general formula (III) can be obtained from the corresponding derivative of general formula:

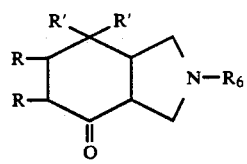
(X)

in which R and R' are defined as above and $R_6$ represents an allyl radical or a radical of structure —$CR_aR_bR_c$, in which $R_a$ and $R_b$ are hydrogen atoms or phenyl radicals, which are optionally substituted (by a halogen atom or an alkyl, alkoxy or nitro radical), and $R_c$ is defined as $R_a$ and $R_b$ or represents an alkyl or alkoxyalkyl radical, at least one of $R_a$, $R_b$ and $R_c$ being a substituted or unsubstituted phenyl radical and the alkyl radicals containing 1 to 4 carbon atoms in a straight or branched chain, by removal of the radical $R_6$ by any known method which does not affect the remainder of the molecule.

In particular, when R is a hydrogen atom and when $R_6$ is other than an allyl radical, the group $R_6$ can be removed by catalytic hydrogenation in the presence of palladium. In general, the reaction takes place in an acid medium, in a solvent such as an alcohol (methanol or ethanol), in water or directly in acetic acid or formic acid, at a temperature between 20° and 60° C.

When $R_6$ is a benzhydryl or trityl radical, the removal can be effected by treatment in an acid medium, working at a temperature between 0° C. and the reflux temperature of the reaction mixture, in an alcohol, in an ether, in water or directly in acetic acid, formic acid or trifluoroacetic acid. The group $R_6$ can also be removed by the action of vinyl chloroformate, 1-chloroethyl chloroformate or phenyl chloroformate, a product of general formula:

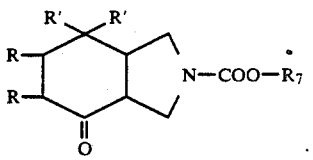

in which R and R' are defined as above and $R_7$ is a vinyl, 1-chloroethyl or phenyl radical, being formed as an intermediate, followed by removal of the radical $R_7$ by acid treatment. The action of the chloroformate generally takes place in an organic solvent, such as a chlorinated solvent (dichloromethane, dichloroethane or chloroform, for example), an ether (tetrahydrofuran or dioxane, for example) or a ketone (acetone, for example) or in a mixture of the solvents, the reaction being carried out at a temperature between 20° C. and the reflux temperature of the reaction mixture.

The removal of the radical $R_7$ is effected by treatment in an acid medium, for example by trifluoroacetic acid, formic acid, methanesulphonic acid, p-toluenesulphonic acid, hydrochloric acid or hydrobromic acid, in a solvent, such as an alcohol, an ether, an ester, a nitrile or a mixture of these solvents or in water, at a temperature between 0° C. and the reflux temperature of the reaction mixture.

Under the abovementioned conditions for removal of the radicals $R_7$, the isoindolone derivative of general formula (III) is obtained in the form of a salt of the acid employed, which salt can be used directly in the subsequent step.

The isoindolone derivative of general formula (X) can be obtained by a cycloaddition reaction by the action of a silyl derivative of general formula:

in which $R_6$ is defined as above, $(R^o)_3$ represents alkyl radicals or alkyl and phenyl radicals and $R^{\infty}$ represents an alkoxy, cyano or phenylthio radical, on the cyclohexenone derivative of general formula (VI).

The reaction is carried out in the presence of a catalytic amount of an acid chosen from trifluoroacetic acid, acetic acid, methanesulphonic acid or the acids mentioned in the undermentioned references, in an organic solvent, such as a chlorinated solvent (dichloromethane or dichloroethane, for example), in an aromatic hydrocarbon, in a nitrile (acetonitrile) or in an ether, at a temperature between 0° C. and the reflux temperature of the reaction mixture.

The silyl derivative of general formula (XII) can be obtained by the methods described by:

Y. Terao et al., Chem. Pharm. Bull., 33, 2762 (1985);
A. Hosomi et al., Chem. Lett., 1117 (1984);
A. Padwa et al., Chem. Ber., 119, 813 (1986) or
Tetrahedron, 41, 3529 (1985).

It is understood that the isoindolone derivatives of general formula (III) and (X) have several stereoisomer forms. When it is desired to obtain a product of general formula (I) in (3aR,7aR) form, the separation of the isomer forms is preferably carried out at the level of the derivative of general formula (III). The separation takes place by any known method compatible with the molecule.

By way of example, the separation can be effected by preparation of an optically active salt, by the action of L(+)- or D(−)- mandelic acid or of dibenzoyltartaric acid followed by separation of the isomers by crystallization. The desired isomer is liberated from its salt in a basic medium.

The new isoindolone derivatives of general formula (I) can be purified, if necessary, by physical methods such as crystallization or chromatography.

If necessary, the new derivatives of general formula (I) for which the symbols $R_1$ and/or $R_2$ contain amino or alkylamino substituents and/or X represents a radical $NR_3$ can be converted to addition salts with acids. Examples which may be mentioned of addition salts with pharmaceutically acceptable acids are the salts formed with inorganic acids (hydrochlorides, hydrobromides, sulphates, nitrates or phosphates) or with organic acids (succinates, fumarates, tartrates, acetates, propionates, maleates, citrates, methanesulphonates, p-toluenesulphonates or isethionates) or with substituted derivatives of these compounds.

The new isoindolone derivatives of general formula (I) can also, if necessary, when $R_2$ represents a carboxyl radical, be converted to metal salts or to addition salts with a nitrogenous base, by the methods known per se. These salts can be obtained by the action of a metal (for example alkali metal or alkaline earth metal) base, ammonia or an amine on a product according to the invention, in an appropriate solvent, such as an alcohol, an ether or water, or by exchange reaction with a salt of an organic acid. The salt formed precipitates, after concentration of the solution if necessary, and is separated off by filtration, settling or lyophilization. Examples which may be mentioned of pharmaceutically acceptable salts are the salts with the alkali metals (sodium, potassium or lithium) or with the alkaline earth metals (magnesium or calcium), the ammonium salt and the salts of nitrogenous bases (ethanolamine, diethanolamine, trimethylamine, triethylamine, methylamine, propylamine, diisopropylamine, N,N-dimethylethanolamine, benzylamine, dicyclohexylamine, N-benzyl-β-phenethylamine, N,N'-dibenzylethylenediamine, diphenylenediamine, benzhydrylamine, quinine, choline, arginine, lysine, leucine or dibenzylamine).

The new isoindolone derivatives according to the present invention which antagonize the effects of substance P can find application in the fields of analgesia, inflammation, asthma and allergies, on the central nervous system, on the cardiovascular system, as an antispasmodic agent, or on the immune system, as well as in the field of stimulation of lachrymal secretions.

In fact, the products according to the invention show an affinity for the substance P receptors at doses of between 5 and 2,000 nM according to the technique described by C. M. Lee et al., Mol. Pharmacol., 23, 563–69 (1983).

It has also been demonstrated that the effect concerned is an antagonist effect on substance P, by means of various products. In the technique described by S. Rosell et al., Substance P, Ed. by U.S. Von Euler and B. Pernow, Raven Press, New-York (1977), pages 83 to 88, the products studied were shown to be active at doses of between 20 and 1,000 nM.

Substance P is known to be involved in some pathological fields:

Agonists and antagonists of substance P, A. S. Dutta Drugs of the future, 12 (8), 782 (1987);

Substance P and pain: an updating, J. L. Henry, TINS, 3 (4), 97 (1980);

Substance P in inflammatory reactions and pain, S. Rosell, Actual. Chim. Ther., 12th series, 249 (1985);

Effects of Neuropeptides on Production of Inflammatory Cytokines by Human Monocytes, M. Lotz et al., Science, 241, 1218 (1988);

Neuropeptides and the pathogenesis of allergy, Allergy, 42, 1 to 11 (1987);

Substance P in Human Essential Hypertension, J. Cardiovascular Pharmacology, 10 (suppl. 12), 5172 (1987).

In particular, it has been demonstrated, by the study of several products, that the new isoindolone derivatives show an analgesic activity in the technique of E. Siegmund et al., Proc. Soc. Exp. Biol. Med., 95, 729 (1957).

| Product of general formula (I) | ED$_{50}$ mg/kg p.o. |
| --- | --- |
| Example 4 | 42 |
| Example 13 | 19 |
| Example 27 | 29 |
| Example 48 | 4 |
| Example 50 | 0.3 |
| Example 60 | 38 |

The study of several isoindolone derivatives of general formula (I) using the technique of A. Saria et al., Arch. Pharmacol., 324, 212–218 (1983) enabled an inhibitory effect on the increase in the capillary permeability caused by substance P to be demonstrated in rats, this being evidence of an anti-inflammatory activity:

| Product of general formula (I) | ED$_{50}$ mg/kg i.v. |
| --- | --- |
| Example 50 | about 0.05 |
| Example 60 | about 1 |

It has also been demonstrated using several products that the new isoindolone derivatives have an impact on the central nervous system: they antagonize the behavioural effects induced by an antagonist of substance P (septide) administered intrathecally to rats using the technique of R. E. Rodriguez et al., Neuropharmacology, 22, (2), 173–176 (1983):

| Product of general formula (I) | % inhibition of the behaviour at a dose of 10 mg/kg sc |
| --- | --- |
| Example 50 | 50 |
| Example 60 | 80 |

The injection of substance P into the animal causes hypotension. The products studied using the technique of C. A. Maggi et al., J. Auton. Pharmac., 7, 11–32 (1987) show an antagonist effect in rats towards this hypotension. In particular, the product of Example 60 administered in a dose of 0.2 mg/kg i.v./min, for 5 min, causes an approximately 50% antagonism of the hypotension induced by an i.v. injection of 250 μg of septide.

Substance P plays a role in the modulation of immune processes (J. P. McGillis et al., Fed. Proc., 46 (1), 196–199 (1987)). Substance P binds to receptors of human cells in cultures: the lymphoblasts of line IM 9 [D. G. Payan et al., J. of Immunology, 133 (6), 3260–5 (1984)]. The products according to the invention displace substance P at these locations.

| Product of general formula (I) | Binding substance P—H$^3$ (concentration 1 nM) on washed homogenates of IM-9 cells after freezing |
| --- | --- |
| Example 49 | 680 |
| Example 76 | 315 |

Finally, the technique of S. ROSELL, Substance P, page 83–88, Raven Press, New-York (1977) used to demonstrate the antagonist effect towards substance P also shows an antagonist activity towards spasms induced by substance P or an agonist of substance P.

Moreover, the isoindolone derivatives according to the present invention are not toxic; they have been shown to be atoxic in mice, administered subcutaneously in a dose of 40 mg/kg or orally in a dose of 100 mg/kg.

Products of general formula (I) which are of particular value are those for which the radicals R are identical and represent hydrogen atoms or together form a bond, the symbols R' are identical and represent phenyl radicals optionally substituted by a fluorine or chlorine atom or by a methyl radical in position 2 or 3, the symbol X represents an oxygen or sulphur atom or a radical N-R$_3$ for which R$_3$ is a hydrogen atom, an alkyl radical containing 1 to 12 carbon atoms and optionally substituted [by one or more carboxyl, dialkylamino, acylamino, alkoxycarbonyl, alkoxycarbonylamino, carbamoyl, alkylcarbamoyl or dialkylcarbamoyl radicals (the alkyl portions of these radicals being able themselves to carry a dialkylamino or phenyl substitutent) or substituted by phenyl, substituted phenyl (substituted by a fluorine or chlorine atom or by an alkyl, alkoxy or dialkylamino radical), naphthyl, 2-thienyl, 2-furyl, pyridyl or imidazolyl radicals] or a dialkylamino radical, the symbol R$_1$ represents a phenyl radical optionally substituted by one or more fluorine, chlorine or bromine atoms or hydroxyl radicals, or alkyl radicals, which can optionally be substituted (by halogen atoms or amino radicals), or alkoxy or alkylthio radicals, which can optionally be substituted (by hydroxyl or dialkylamino radicals in which the alkyl parts can form, with the nitrogen atom to which they are attached, a 6-membered heterocycle which can contain another nitrogen atom optionally substituted by an alkyl radical), or substituted by amino, alkylamino or dialkylamino radicals, in which the alkyl parts can form, with the nitrogen atom to which they are attached, a saturated 5- or 6-membered heterocycle, which can also contain another oxygen atom, or represents a cyclohexadienyl or naphthyl radical or a saturated or unsaturated monocyclic or polycyclic heterocyclic radical containing 5 to 9 carbon atoms and one or more hetero-atoms chosen from nitrogen or sulphur, and the symbol $R_2$ represents a hydrogen or fluorine atom or a hydroxyl, alkyl, aminoalkyl, alkylaminoalkyl, dialkylaminoalkyl, alkoxy, alkylthio, acyloxy, carboxyl, alkoxycarbonyl, dialkylaminoalkoxycarbonyl, benzyloxycarbonyl, amino, acylamino or alkoxycarbonylamino radical, the abovementioned alkyl and acyl radicals being straight-chain or branched and containing 1 to 4 carbon atoms.

And amongst these products, the following products are particularly valuable:

2-[1-imino-2-(2-methoxyphenyl)ethyl]-7,7-diphenyl-4-perhydroisoindolone in its (3aR,7aR) or (3aR,7aRS) forms;

7,7-diphenyl-2-[2-(2-dimethylaminophenyl)acetyl]-4-perhydroisoindolone in its (3aR,7aR) or (3aRS,7aRS) forms;

7,7-diphenyl-2-[(R)-2-(2-methoxyphenyl)propionyl]-4-perhydroisoindolone in its (3aR,7aR) or (3aRS,7aRS) forms;

2-{[2-(3-dimethylaminopropoxy)phenyl]acetyl}-7,7-diphenyl-4-perhydroisoindolone in its (3aR,7aR) or (3aRS,7aRS) forms; and 2-[(S)-1-carboxybenzylimino-2-(2-methoxyphenyl)ethyl]-7,7-diphenyl-4-perhydroisoindolone in its (3aR,7aR) or (3aRS,7aRS) forms.

EXAMPLES

The following examples, given without any limitation being implied, illustrate the present invention.

In the examples which follow it is understood that, unless mentioned in particular, the proton NMR spectra were recorded at 250 MHz in dimethylsulphoxide; the chemical shifts are expressed in ppm.

EXAMPLE 1

N,N'-Carbonyldiimidazole (1.7 g) is added to a solution of phenylacetic acid (1.34 g) in dry dichloromethane (30 cc) cooled to +5° C. The mixture is stirred for 1 hour at +5° C. and a solution of 7,7-diphenyl-4-perhydroisoindolone hydrochloride (3.27 g) and triethylamine (1.7 cc) in dichloromethane (30 cc) is then added. The reaction mixture is stirred for 1 hour at +5° C. and then for 1 hour at 20° C. The reaction mixture is washed with a saturated aqueous solution (50 cc) of sodium bicarbonate, dried over magnesium sulphate and filtered and the filtrate is concentrated to dryness under reduced pressure (2.7 kPa). The residue is crystallized from acetonitrile (15 cc). The crystals are drained, washed with isopropyl ether (10 cc) and dried. (3aRS,7aRS)-7,7-diphenyl-2-(phenylacetyl)-4-perhydroisoindolone (2.7 g) melting at 216° C. is obtained.

(3aRS,7aRS)-7,7-diphenyl-4-perhydroisoindolone hydrochloride can be prepared by one of the following methods:

a) (3aRS,7aRS)-2-benzyl-7,7-diphenyl-4-perhydroisoindolone (150 g), methanol (1,500 cc) and 1N hydrochloric acid (450 cc) are added to 10% palladium-on-charcoal (15 g); the reaction mixture is hydrogenated, with stirring, at ambient temperature and under atmospheric pressure. After a reaction time of 5 hours, the theoretical volume of hydrogen has been absorbed; the reaction mixture is filtered and the filtrate is then concentrated to dryness under reduced pressure (2.7 kPa); the residue is crystallized from ethanol (200 cc); the crystals obtained are drained, washed with ethanol (50 cc) and dried. (3aRS,7aRS)-7,7-diphenyl-4-perhydroisoindolone hydrochloride (110 g) melting at 270° C. with decomposition is obtained.

Proton NMR spectrum: 2.03 (Mt, 1H, 1H of the H in 5 or 6); 2.3 (Mt, 1H, 1H of the —H in 5 or 6); 2.48 (DD, partially masked, 1H of the —CH$_2$— in 1); 2.69 (DD, 1H, 1H of the —CH$_2$— in 1); 2.8 (Mt, 2H, —CH$_2$— in 6 or 5); 3.34 (DD, partially masked, 1H of the —CH$_2$— in 3); 3.5 (Mt, 1H, —CH— in 3a); 3.82 (DD, 1H, 1H of the —CH$_2$— in 3); 3.95 (Mt, 1H, —CH— in 7a); 7.15 to 7.65 (Mt, 10H, aromatic); 9.43 (Mf, 2H, —NH$_2$—Cl).

Infrared spectrum (KBr), characteristic bands in cm$^{-1}$; 3600–3300, 3100–3000, 3000–2850, 3100–2400, 1715, 1595, 1580, 1495, 1470, 1445, 775, 750, 705.

b) Vinyl chloroformate (56 cc) is added dropwise in the course of 10 minutes to a solution of (3aRS,7aRS)-2-benzyl-7,7-diphenyl-4-perhydroisoindolone (193 g) in 1,2-dichloroethane (1,225 cc) cooled to +5° C. After stirring for 30 minutes at between 10° and 20° C., the reaction mixture is refluxed for 90 minutes, cooled and concentrated to dryness under reduced pressure (2.7 kPa then 1 kPa). The crystalline mass obtained is pounded with cold isopropyl ether (200 cc). The crystals obtained are drained, washed with isopropyl ether (2 * 100 cc) and dried. (3aRS,7aRS)-7,7-diphenyl-2-vinyloxycarbonyl-4-perhydroisoindolone (177 g) melting at 178° C. is obtained.

(3aRS,7aRS)-7,7-diphenyl-2-vinyloxycarbonyl-4-perhydroisoindolone (177 g) is treated with a 5.7N solution (1,000 cc) of hydrochloric acid in dry dioxane for 30 minutes at 20° C. The solution is concentrated to dryness under reduced pressure (2.7 kPa) and the residue is taken up in ethanol (500 cc) and the reaction mixture is stirred at 60° C. for 30 minutes and then cooled to +5° C. The crystals obtained are drained, washed with ethanol (50 cc) and dried. (3aRS,7aRS)-7,7-diphenyl-4-perhydroisoindolone hydrochloride (130 g) melting at 270° C. is obtained.

(3aRS,7aRS)-2-benzyl-7,7-diphenyl-4-perhydroisoindolone can be prepared in the following way:

Trifluoroacetic acid (5 drops) is added to a solution of 4,4-diphenyl-cyclohex-2-en-1-one (155 g) and N-butoxymethyl-N-trimethylsilylmethyl-benzylamine (202 cc) in dry dichloromethane (1,000 cc) and the reaction mixture is refluxed for 45 minutes. N-Butoxymethyl-N-trimethylsilylmethyl-benzylamine (50 cc) and trifluoroacetic acid (3 drops) are added and the mixture is stirred for a further 45 minutes under reflux before adding further N-butoxymethyl-N-trimethylsilylmethyl-benzylamine (25 cc) and trifluoroacetic acid (3 drops). The reaction mixture is stirred under reflux for 45 minutes and then treated with potassium carbonate (50 g) and filtered and the filtrate is concentrated to dryness under reduced pressure (2.7 kPa). The residue is dissolved in isopropyl ether (200 cc) and the solution is cooled at 0° C. for 1 hour. The crystals are drained, washed with isopropyl ether (2 * 15 cc) and dried to give (3aRS,-

7aRS)-2-benzyl-7,7-diphenyl-4-perhydroisoindolone (193 g) in the form of white crystals melting at 132° C.

N-Butoxymethyl-N-trimethylsilylmethyl-benzylamine can be prepared by the method of Y. Terao et al., Chem. Pharm. Bull., 33, 2762 (1985).

EXAMPLE 2

A solution of phenylacetyl chloride (4 cc) and triethylamine (8.6 cc) in dichloromethane (10 cc) is added dropwise to a solution of (3aR,7aR)-7,7-diphenyl-4-perhydroisoindolone hydrochloride (10 g) in dry dichloromethane (80 cc) cooled to +5° C. The reaction mixture is stirred for 2 hours at +5° C. and then for 20 hours at 20° C. The reaction mixture is treated with a saturated aqueous solution (30 cc) of sodium bicarbonate; the organic phase is washed with distilled water (2 * 50 cc), dried over magnesium sulphate and filtered and the filtrate is concentrated to dryness under reduced pressure (2.7 kPa). The residue is crystallized from acetonitrile (15 cc). The crystals are drained, washed with acetonitrile (10 cc) and with isopropyl ether (10 cc) and dried. (3aR,7aR)-7,7-diphenyl-2-(phenylacetyl)-4-perhydroisoindolone (5.7 g) melting at 173° C. is obtained; $[\alpha]_D^{20} = -282°$ (c=1, methanol).

(3aR,7aR)-7,7-diphenyl-4-perhydroisoindolone hydrochloride can be prepared in the following way:

4N aqueous sodium hydroxide solution (500 cc) is added slowly, with stirring, to a suspension of (3aRS,7aRS)-7,7-diphenyl-4-perhydroisoindolone hydrochloride (200 g) in ethyl acetate (2,000 cc); stirring is continued until all of the starting material has dissolved. The organic solution is washed with distilled water (250 cc) and with a saturated aqueous solution (250 cc) of sodium chloride, dried over magnesium sulphate and filtered. A solution of L(+)-mandelic acid (92.8 g) in ethyl acetate (1,000 cc) is added to the solution thus obtained, with stirring; after stirring for 4 hours, the crystals obtained are drained, washed with ethyl acetate (2 * 250 cc) and dried. The crystals are taken up in distilled water (2,000 cc); the mixture is refluxed, with stirring, for 15 minutes; the insoluble crystals are drained, washed with distilled water (2 * 100 cc) and dried. They are recrystallized from a mixture of acetonitrile (1,100 cc) and distilled water (500 cc); the crystals obtained are drained, washed with acetonitrile (3 * 40 cc) and dried. (3aR,7aR)-7,7-diphenyl-4-perhydroisoindolone (L)-mandelate (80 g) is obtained; $[\alpha]_D^{20} = -164°$ (c=1, methanol).

1N aqueous sodium hydroxide solution (400 cc) and ethyl acetate (600 cc) are added to (3aR,7aR)-7,7-diphenyl-4-perhydroisoindolone (L)-mandelate (80 g); the mixture is stirred at ambient temperature until the starting material has dissolved; the organic solution is washed with distilled water (250 cc) and with a saturated aqueous solution (250 cc) of sodium chloride, dried over magnesium sulphate and filtered; the filtrate is acidified, with stirring, by the addition of 9N hydrochloric acid (30 cc); the crystals obtained are drained, washed with ethyl acetate (2 * 50 cc) and with isopropyl ether (50 cc) and dried. (3aR,7aR)-7,7-diphenyl-4-perhydroisoindolone hydrochloride (52.3 g) melting at 270° C. with decomposition is obtained; $[\alpha]_D^{20} = -282°$ (c=0.5, methanol).

EXAMPLE 3

2,4-Bis-(4-methoxyphenyl)-2,4-dithioxo-1,3,2,4-dithiadiphosphetane (3.95 g) is added to a solution of (3aRS,7aRS)-7,7-diphenyl-2-phenylacetyl-4-perhydroisoindolone (4 g) in tetrahydrofuran (160 cc); stirring of the reaction mixture is continued for 20 hours at ambient temperature. The reaction mixture is treated with a 20% aqueous ammonia solution (10 cc) and with distilled water (30 cc) and is then extracted with ethyl acetate (2 * 150 cc); the organic phases are combined and washed with distilled water (2 * 200 cc) and with a saturated aqueous solution (100 cc) of calcium chloride, dried over magnesium sulphate and concentrated to dryness under reduced pressure (2.7 kPa). The residue is chromatographed on a silica gel column (0.06–0.2 mm, diameter 3 cm, height 30 cm) eluting with a mixture of cyclohexane and ethyl acetate (50/50 by volume), recovering 25 cc fractions. Fractions 1 to 6 are combined and concentrated to dryness under reduced pressure (2.7 kPa). The crystals obtained are washed with isopropyl ether (20 cc), drained and dried. (3aRS,7aRS)-7,7-diphenyl-2-(2-phenylthioacetyl)-4-perhydroisoindolone (1.5 g) melting at 221° C. is obtained.

EXAMPLE 4

Triethyloxonium tetrafluoborate (10.45 g) is added to a solution of (3aRS,7aRS)-7,7-diphenyl-2-phenylacetyl-4-perhydroisoindolone (20 g) in dichloromethane (50 cc). Stirring of the reaction mixture is continued for 20 hours at ambient temperature. The precipitate obtained is drained, washed with anhydrous dichloromethane (10 cc) and with anhydrous ether (10 cc) and dried; (3aRS,7aRS)-2-[(1-ethoxy-2-phenyl)ethylidene]-4-oxo-7,7-diphenyl-perhydroisoindolium tetrafluoborate (11.1 g) is obtained in the form of a white powder used in the crude state for the following operations.

A 0.8N solution (8.8 cc) of dichloromethane in ammonia is added to a stirred suspension of (3aRS,7aRS)-2-[(1ethoxy-2-phenyl)ethylidene]-4-oxo-7,7-diphenyl-perhydroisoindolium tetrafluoborate (3.75 g) in anhydrous dichloromethane (30 cc), which is cooled to −20° C. The temperature of the reaction mixture is allowed to return to ambient temperature and stirring is continued for 5 hours. The reaction mixture is treated with a 10% aqueous solution (30 cc) of potassium carbonate. The precipitate present is removed by filtration and the organic phase is then washed with distilled water (15 cc) and with a saturated aqueous solution (15 cc) of sodium chloride, dried over magnesium sulphate and concentrated to dryness under reduced pressure (2.7 kPa). The residue is recrystallized from acetonitrile (22 cc). The crystals obtained are drained and dried. (3aRS,7aRS)-2-(α-iminophenethyl)-7,7-diphenyl-4-perhydroisoindolone (1.3 g) melting at 202° C. is obtained.

EXAMPLE 5

Methylamine (0.43 cc) is added to a stirred suspension of (3aRS,7aRS)-2-[(1-ethoxy-2-phenyl)-ethylidene]-4-oxo-7,7-diphenyl-perhydroisoindolium tetrafluoborate (3 g), prepared according to Example 4, in anhydrous dichloromethane (5 cc). Stirring of the reaction mixture is continued for 3 hours at ambient temperature; the reaction mixture is diluted with dichloromethane (40 cc) and treated with an aqueous solution (15 cc) containing potassium carbonate (22 g). The precipitate present is removed by filtration and the organic phase is then washed with distilled water (15 cc) and with a saturated aqueous solution (10 cc) of sodium chloride, dried over magnesium sulphate and concentrated to dryness under reduced pressure (2.7 kPa). The residue is chromatographed on a Péchiney CBT1 neutral alumina gel column (diameter 3 cm, height 23.5 cm) eluting with a mixture (750 cc) of cyclohexane and ethyl acetate (10/90 by volume), with ethyl acetate (250 cc) and with a mixture (500 cc) of ethyl acetate and methanol (95/5 by volume) and collecting 25 cc fractions. Fractions 41 to 65 are combined and concentrated to dryness under reduced pressure (2.7 kPa). The residue is crystallized from acetonitrile (0.5 cc); the crystals obtained are drained, washed with acetonitrile (0.5 cc) and dried. (3aRS,7aRS)-2-(α-methyliminophenethyl)-7,7-diphenyl-4-perhydroisoindolone (0.5 g) melting at 110° C. is obtained.

EXAMPLE 6

Ethylamine (0.3 cc) is added to a stirred suspension of (3aRS,7aRS)-2-[(1-ethoxy-2-phenyl)ethylidene]-4-oxo-7,7-diphenyl-perhydroisoindolium tetrafluoroborate (3 g), prepared in accordance with Example 4, in anhydrous dichloromethane (5 cc). Stirring of the reaction mixture is continued for 20 hours at ambient temperature. The precipitate obtained is drained, washed with ethyl ether (30 cc) and dried. It is dissolved in dichloromethane (40 cc) and the solution is washed with an aqueous solution (15 cc) containing potassium carbonate (44 g), with distilled water (30 cc) and with a saturated aqueous solution (15 cc) of sodium chloride; it is dried over magnesium sulphate and concentrated to dryness under reduced pressure (2.7 kPa). The residue is recrystallized from isopropanol (15 cc); the crystals obtained are drained and dried. (3aRS,7aRS)-2-(α-ethyliminophenethyl)-7,7-diphenyl-4-perhydroisoindolone (1.15 g) melting at 108° C. is obtained.

EXAMPLE 7

Propylamine (0.6 cc) is added to a stirred suspension of (3aRS,7aRS)-2-[(1-ethoxy-2-phenyl)-ethylidene]-4-oxo-7,7-diphenyl-perhydroisoindolium tetrafluoborate (3.5 g), prepared in accordance with Example 4, in anhydrous dichloromethane (30 cc), which is cooled to +5° C. Stirring of the reaction mixture is continued for 20 hours at ambient temperature; the reaction mixture is treated with a 10% aqueous solution (30 cc) of potassium carbonate. The precipitate present is removed by filtration and the organic phase is then washed with distilled water (15 cc) and with a saturated aqueous solution (15 cc) of sodium chloride, dried over magnesium sulphate and concentrated to dryness under reduced pressure (2.7 kPa). The residue is recrystallized from acetonitrile (5 cc). The crystals obtained are drained and dried. (3aRS,7aRS)-2-(α-propyliminophenethyl)-7,7-diphenyl-4-perhydroisoindolone (0.5 g) melting at 86° C. is obtained.

EXAMPLE 8

2-N,N-Dimethylaminoethylamine (0.77 cc) is added to a stirred suspension of (3aRS,7aRS)-2-[(1-ethoxy-2-phenyl)ethylidene]-4-oxo-7,7-diphenyl-perhydroisoindolium tetrafluoborate (3.75 g), prepared in accordance with Example 4, in anhydrous dichloromethane (30 cc), which is cooled to +5° C. Stirring of the reaction mixture is continued for 20 hours at ambient temperature. The reaction mixture is treated with a 10% aqueous solution (30 cc) of potassium carbonate. The precipitate present is removed by filtration and the organic phase is then washed with distilled water (15 cc) and with a saturated aqueous solution (15 cc) of sodium chloride, dried over magnesium sulphate and concentrated to dryness under reduced pressure (2.7 kPa). The residue is crystallized from acetonitrile (5 cc). The crystals obtained are drained and dried. They are recrystallized from acetonitrile (6 cc). The crystals obtained are drained and dried. (3aRS,7aRS)-2-[α-(2-N,N-dimethylaminoethylimino)phenethyl]-7,7-diphenyl-4-perhydroisoindolone (1.6 g) melting at 134° C. is obtained.

EXAMPLE 9

6-Acetylaminohexylamine (0.63 g) is added to a suspension of (3aRS,7aRS)-2-[(1-ethoxy-2-phenyl)-ethylidene]-4-oxo-7,7-diphenyl-perhydroisoindolium tetrafluoborate (2.1 g) in anhydrous dichloromethane (15 cc). The reaction mixture is stirred for 16 hours at 20° C. and then diluted with a 20% aqueous solution (50 cc) of potassium carbonate and dichloromethane (50 cc), stirred and then filtered. The organic phase is washed with a saturated solution (50 cc) of sodium chloride, dried over magnesium sulphate and concentrated to dryness under reduced pressure (2.7 kPa). The residue is chromatographed on a CBT1 alumina column (diameter 3 cm, height 24 cm) eluting under a pressure of 0.5 bar with ethyl acetate (1 liter) and then with a mixture of 1,2-dichloroethane and ethanol (90/10 by volume), collecting 75 cc fractions. Fractions 15 to 23 are combined and concentrated to dryness under reduced pressure (2.7 kPa) to give (3aRS,7aRS)-2-[-1-(6-acetamido-1-hexyl)imino-2-phenylethyl]-7,7-diphenyl-4-perhydroisoindolone (1.2 g) in the form of a white meringue.

Proton NMR spectrum (DMSO-$d_6$): 1.18 (m, 4H, =N—$\underline{CH_2}$—CH_2—CH_2—CH_2—CH_2—$\underline{CH_2}$—NHAc); 1.32 (m, 4H, =N—$\overline{CH_2}$—$\underline{CH_2}$—$\underline{CH_2}$—$\underline{CH_2}$—$\underline{CH_2}$—NHAc); 1.8 (s, 3H, —$\overline{COCH_3}$); 1.95 to 2.30 (m, 2H, —CH_2— in 5); 2.55 to 2.95 (m, 4H, —CH_2— in 6 and in 1); 2.96 (m, 2H, —$\underline{CH_2}$—NHAc); 3.05 (t, J=7, =N—$\underline{CH_2}$—); 3.24 (m, 1H, $\overline{H}$ in 3a); 3.34 (dd, J=11 and 6, 1H, 1H in 3); 3.69 (AB, 2H, ArCH_2); 4 (m, 1H, H in 7a); 4.12 (d, J=11, 1H, 1H in 3); 7 to 7.7 (m, 15H, aromatic); 7.8 (t, J=5, 1H, —NHAc).

Infrared spectrum (characteristic bands in cm$^{-1}$): 3290, 3100–3000, 3000–2825, 1715, 1655, 1615, 1600, 1580, 1495, 1550, 750, 700.

EXAMPLE 10

A solution of iodomethane (20 g) in acetone (200 cc) is added to a solution of (3aRS,7aRS)-7,7-diphenyl-2-(2-phenylthioacetyl)-4-perhydroisoindolone (20 g) in acetone (150 cc). The reaction mixture is stirred at +50° C. for 20 hours. The precipitate obtained is drained, washed with isopropyl ether and dried. (3aRS,7aRS)-2-[(1-methylthio-2-phenyl)ethylidene]-4-oxo-7,7-diphenyl-perhydroisoindolium iodide (23.7 g) is obtained in the form of white solid.

A solution of isobutylamine (0.65 g) in tetrahydrofuran (5 cc) is added dropwise at ambient temperature to a solution of (3aRS,7aRS)-2-[(1-methylthio-2-phenyl)ethylidene]-4-oxo-7,7-diphenylperhydroisoindolium iodide (5 g) in anhydrous tetrahydrofuran (50 cc). Stirring of the reaction mixture is continued for 20 hours at ambient temperature. The precipitate obtained is drained and dried. (3aRS,7aRS)-7,7-diphenyl-2-[(isobutylimino)phenethyl]-4-perhydroisoindolone hydroiodide (4.3 g) is obtained in the form of white crystals melting at 241° C.

EXAMPLE 11

6-Acetylaminohexylamine (0.63 g) is added to a suspension of (3aRS,7aRS)-2-[(1-ethoxy-2-phenyl)ethylidene]-4-oxo-7,7-diphenyl-perhydroisoindolium tetrafluoborate (2.1 g) in anhydrous dichloromethane (15 cc). The reaction mixture is stirred for 16 hours at 20° C. and then diluted with a 20% aqueous solution (50 cc) of potassium carbonate and dichlormethane (50 cc), stirred and then filtered. The organic phase is washed with a saturated solution (50 cc) of sodium chloride, dried over magnesium sulphate and concentrated to dryness under reduced pressure (2.7 kPa). The residue is chromatographed on a CBT1 alumina column (diameter 3 cm, height 24 cm) eluting under a pressure of 0.5 bar with ethyl acetate (1 liter) and then with a mixture of 1,2-dichloroethane and ethanol (90/10), collecting 75 cc fractions. Fractions 15 to 23 are combined and concentrated to dryness under reduced pressure (2.7 kPa) to give (3aRS,7aRS)-2-[1-(6-acetamido-1-hexyl)imino-2-phenylethyl]-7,7-diphenyl-4-perhydroisoindolone (1.2 g) in the form of a white meringue.

Proton NMR spectrum (DMSO-d$_6$): 1.18 (m, 4H, =N—CH$_2$—CH$_2$—CH$_2$—CH$_2$—CH$_2$—CH$_2$—NHAc); 1.32 (m, 4H, =N—$\overline{\text{CH}_2}$—CH$_2$—CH$_2$—CH$_2$—$\overline{\text{CH}}$$_2$—CH$_2$—NHAc); 1.8 (s, 3H, —COCH$_3$); 1.95 to 2.30 (m, 2H, —CH$_2$— in 5); 2.55 to 2.95 (m, 4H, —CH$_2$— in 6 and in 1); 2.96 (m, 2H, —CH$_2$—NHAc); 3.05 (t, J=7, =N—CH$_2$—); 3.24 (m, 1H, $\overline{\text{H}}$ in 3a); 3.34 (dd, J=11 and 6, 1H, 1H in 3); 3.69 (AB, 2H, ArCH$_2$—); 4 (m, 1H, H in 7a); 4.12 (d, J=11, 1H, 1H in 3); 7 to 7.7 (m, 15H, aromatic); 7.8 (t, J=5, 1H, —NHAc).

Infrared spectrum (characteristic bands in cm$^{-1}$): 3290, 3100-3000, 3000-2825, 1715, 1655, 1615, 1600, 1580, 1495, 1550, 750, 700.

EXAMPLE 12

Triethylamine (1.2 cc) and then (3aRS,7aRS)-2-[(1-ethoxy-2-phenyl)ethylidene]-4-oxo-7,7-diphenylperhydroisoindolium tetrafluoborate (5 g), prepared in accordance with Example 4, are added to a solution of methyl glycinate hydrochloride (1.2 g) in anhydrous dichloromethane (40 cc). Stirring of the reaction mixture is continued for 20 hours at ambient temperature; the reaction mixture is washed with distilled water (2×50 cc), dried over magnesium sulphate and concentrated to dryness under reduced pressure (2.7 kPa). The residue is chromatographed on a Péchiney CBT1 neutral alumina gel column (diameter 3 cm, height 23.5 cm), eluting with a mixture of cyclohexane and ethyl acetate (30/70 by volume) and collecting 60 cc fractions. Fractions 9 to 23 are combined and concentrated to dryness under reduced pressure (2.7 kPa). (3aRS,7aRS)-2-(α-methoxycarbonylmethyliminophenethyl)-7,7-diphenyl-4-perhydroisoindolone (0.4 g) melting at 147° C. is obtained.

EXAMPLE 13

Benzylamine (1.3 cc) is added to a stirred suspension of (3aRS,7aRS)-2-[(1-ethoxy-2-phenyl)ethylidene]-4-oxo-7,7-diphenyl-perhydroisoindolium tetrafluoborate (6.5 g), prepared in accordance with Example 4, in anhydrous dichloromethane (25 cc). Stirring of the reaction mixture is continued for 20 hours at ambient temperature; the reaction mixture is diluted with dichloromethane (30 cc) and treated with an aqueous solution (30 cc) containing potassium carbonate (44 g). The precipitate present is removed by filtration and the organic phase is then washed with distilled water (2×30 cc) and with a saturated aqueous solution (30 cc) of sodium chloride, dried over magnesium sulphate and concentrated to dryness under reduced pressure (2.7 kPa). The residue is chromatographed on a Péchiney CBT1 neutral alumina gel column (diameter 4.5 cm, height 28 cm), eluting with ethyl acetate and collecting 60 cc fractions. Fractions 2 to 4 are combined and concentrated to dryness under reduced pressure (2.7 kPa). The residue is crystallized from acetonitrile (10 cc); the crystals obtained are drained, washed with acetonitrile (5 cc) and dried. (3aRS,7aRS)-2-(α-benzyliminophenethyl)-7,7-diphenyl-4-perhydroisoindolone (2.5 g) melting at 165° C. is obtained.

EXAMPLE 14

Phenethylamine (0.9 cc) is added to a stirred suspension of (3aRS,7aRS)-2-[(1-ethoxy-2-phenyl)ethylidene]-4-oxo-7,7-diphenyl-perhydroisoindolium tetrafluoborate (3.75 g), prepared in accordance with Example 4, in anhydrous dichloromethane (40 cc), which is cooled to +5° C. Stirring of the reaction mixture is continued for 20 hours at ambient temperature; the reaction mixture is treated with a 10% aqueous solution (30 cc) of potassium carbonate. The precipitate present is removed by filtration and the organic phase is then washed with distilled water (15 cc) and with a saturated aqueous solution (10 cc) of sodium choloride, dried over magnesium sulphate and concentrated to dryness under reduced pressure (2.7 kPa). The residue is recrystallized from acetonitrile (100 cc). The crystals obtained are drained and dried. (3aRS,7aRS)-2-(α-phenethyliminophenethyl)-7,7-diphenyl-4-perhydroisoindolone (2.05 g) melting at 188° C. is obtained.

EXAMPLE 15

3-Phenylpropylamine (1.15 cc) is added to a stirred suspension of (3aRS,7aRS)-2-[(1-ethoxy-2-phenyl)ethylidene]-4-oxo-7,7-diphenyl-perhydroisoindolium tetrafluoborate (5.25 g), prepared in accordance with Example 4, in anhydrous dichloromethane (30 cc), which is cooled to +5° C. The temperature of the reaction mixture is then allowed to rise to ambient temperature and stirring is continued for 20 hours. The reaction mixture is treated with a 10% aqueous solution (20 cc) of potassium carbonate. The precipitate present is removed by filtration and the organic phase is then washed with distilled water (25 cc) and with a saturated aqueous solution (25 cc) of sodium chloride, dried over magnesium sulphate and concentrated to dryness under reduced pressure (2.7 kPa). The residue is crystallized from acetonitrile (5 cc). The crystals obtained are drained and dried. They are recrystallized from acetonitrile (15 cc); the crystals obtained are drained and dried. (3aRS,7aRS)-7,7-diphenyl-2-[α-(3-phenylpropylimino)-phenethyl]-4-perhydroisoindolone (1.9 g) melting at 144° C. is obtained.

EXAMPLE 16

Aminodiphenylmethane (1.7 cc) is added to a stirred suspension of (3aRS,7aRS)-2-[(1-ethoxy-2-phenyl)ethylidene]-4-oxo-7,7-diphenyl-perhydroisoindolium tetrafluoborate (5 g), prepared in accordance with Example 4, in anhydrous dichloromethane (10 cc). Stirring of the reaction mixture is continued for 20 hours at ambient temperature and the reaction mixture is then treated with a saturated aqueous solution (20 cc) of potassium carbonate. The precipitate present is removed by filtration and the organic phase is then dried over magnesium sulphate and concentrated to dryness under reduced pressure (2.7 kPa). The residue is chromatographed on a Péchiney CBT1 neutral alumina gel column (diameter 3.4 cm, height 28 cm), eluting with 1,2-dichloroethane and collecting 60 cc fractions. Fractions 8 to 10 are combined and concentrated to dryness under reduced pressure (2.7 kPa). The residue is crystallized from acetonitrile (2 cc); the crystals obtained are drained, washed with acetonitrile (2 cc) and dried. (3aRS,7aRS)-7,7-diphenyl-2-(α-diphenylmethyliminophenethyl)-4-perhydroisoindolone (0.17 g) melting at 172° C. is obtained.

EXAMPLE 17

2-Fluorobenzylamine (1 cc) is added to a stirred suspension of (3aRS,7aRS)-2-[(1-ethoxy-2-phenyl)ethylidene]-4-oxo-7,7-diphenyl-perhydroisoindolium tetrafluoborate (4.5 g), prepared in accordance with Example 4, in anhydrous dichloromethane (10 cc). Stirring of the reaction mixture is continued for 20 hours at ambient temperature; the reaction mixture is diluted with dichloromethane (20 cc) and treated with a saturated aqueous solution (20 cc) of potassium carbonate. The precipitate present is removed by filtration and the organic phase is then dried over magnesium sulphate and concentrated to dryness under reduced pressure (2.7 kPa). The residue is crystallized from a mixture of acetonitrile (10 cc) and isopropyl ether (5 cc); the crystals obtained are drained, washed with acetonitrile (5 cc) and dried. (3aRS,7aRS)-2-[α-(2-fluorobenzyl)iminophenethyl]-7,7-diphenyl-4-perhydroisoindolone (1.3 g) melting at 160° C. is obtained.

EXAMPLE 18

3-Fluorobenzylamine (0.95 cc) is added to a stirred suspension of (3aRS,7aRS)-2-[(1-ethoxy-2-phenyl)ethylidene]-4-oxo-7,7-diphenyl-perhydroisoindolium tetrafluoborate (4.2 g), prepared in accordance with Example 4, in anhydrous dichloromethane (10 cc). Stirring of the reaction mixture is continued for 20 hours at ambient temperature; the reaction mixture is diluted with dichloromethane (20 cc) and treated with a saturated aqueous solution (20 cc) of potassium carbonate. The precipitate present is removed by filtration and the organic phase is then dried over magnesium sulphate and concentrated to dryness under reduced pressure (2.7 kPa). The residue is crystallized from acetonitrile (10 cc); the crystals obtained are drained, washed with acetonitrile (5 cc) and dried. (3aRS,7aRS)-2-[α-(3-fluorobenzyl)iminophenethyl]-7,7-diphenyl-4-perhydroisoindolone (1.7 g) melting at 156° C. is obtained.

EXAMPLE 19

4-Fluorobenzylamine (0.95 cc) is added to a stirred suspension of (3aRS,7aRS)-2-[(1-ethoxy-2-phenyl)ethylidene]-4-oxo-7,7-diphenyl-perhydroisoindolium tetrafluoborate (4.2 g), prepared in accordance with Example 4, in anhydrous dichloromethane (10 cc). Stirring of the reaction mixture is continued for 20 hours at ambient temperature; the reaction mixture is diluted with dichloromethane (20 cc) and treated with a saturated aqueous solution (20 cc) of potassium carbonate. The precipitate present is removed by filtration and the organic phase is then dried over magnesium sulphate and concentrated to dryness under reduced pressure (2.7 kPa). The residue is crystallized from acetonitrile (10 cc); the crystals obtained are drained, washed with acetonitrile (5 cc) and dried. (3aRS,7aRS)-2-[α-(4-fluorobenzyl)iminophenethyl]-7,7-diphenyl-4-perhydroisoindolone (2.7 g) melting at 180° C. is obtained.

EXAMPLE 20

2-Chlorobenzylamine (1.2 cc) is added to a stirred suspension of (3aRS,7aRS)-2-[(1-ethoxy-2-phenyl)ethylidene]-4-oxo-7,7-diphenyl-perhydroisoindolium tetrafluoborate (5 g), prepared in accordance with Example 4, in anhydrous dichloromethane (10 cc). Stirring of the reaction mixture is continued for 20 hours at ambient temperature; the reaction mixture is treated with a saturated aqueous solution (20 cc) of potassium carbonate. The precipitate present is removed by filtration and the organic phase is then dried over magnesium sulphate and concentrated to dryness under reduced pressure (2.7 kPa). The residue is crystallized from acetonitrile (5 cc); the crystals obtained are drained, washed with acetonitrile (5 cc) and dried. (3aRS,7aRS)-2-[α-(2-chlorobenzyl)iminophenethyl]-7,7-diphenyl-4-perhydroisoindolone (2.2 g) melting at 192° C. is obtained.

EXAMPLE 21

4-Chlorobenzylamine (1.2 cc) is added to a stirred suspension of (3aRS,7aRS)-2-[(1-ethoxy-2-phenyl)ethylidene]-4-oxo-7,7-diphenyl-perhydroisoindolium tetrafluoborate (5 g), prepared in accordance with Example 4, in anhydrous dichloromethane (10 cc). Stirring of the reaction mixture is continued for 20 hours at ambient temperature; the reaction mixture is treated with a saturated aqueous solution (20 cc) of potassium carbonate. The precipitate present is removed by filtration and the organic phase is then dried over magnesium sulphate and concentrated to dryness under reduced pressure (2.7 kPa). The residue is crystallized from acetonitrile (20 cc); the crystals obtained are drained, washed with acetonitrile (10 cc) and dried. (3aRS,7aRS)-2-[α-(4-chlorobenzyl)iminophenethyl])-7,7-diphenyl-4-perhydroisoindolone (2.9 g) melting at 198° C. is obtained.

EXAMPLE 22

2-Methoxybenzylamine (1 cc) is added to a stirred suspension of (3aRS,7aRS)-2-[(1-ethoxy-2-phenyl)ethylidene]-4-oxo-7,7-diphenyl-perhydroisoindolium tetrafluoborate (4.1 g), prepared in accordance with Example 4, in anhydrous dichloromethane (10 cc). Stirring of the reaction mixture is continued for 20 hours at ambient temperature; the reaction mixture is diluted with dichloromethane (20 cc) and treated with a saturated aqueous solution (20 cc) of potassium carbonate. The precipitate present is removed by filtration and the organic phase is then dried over magnesium sulphate and concentrated to dryness under reduced pressure (2.7 kPa). The residue is crystallized from a mixture of acetonitrile (5 cc) and isopropyl ether (10 cc); the crystals obtained are drained, washed with acetonitrile (5 cc) and dried. (3aRS,7aRS)-2-[α-(2-methoxybenzyl)iminophenethyl]-7,7-diphenyl-4-perhydroisoindolone (1.6 g) melting at 146° C. is obtained.

EXAMPLE 23

3-Methoxybenzylamine (1 cc) is added to a stirred suspension of (3aRS,7aRS)-2-[(1-ethoxy-2-phenyl)ethylidene]-4-oxo-7,7-diphenyl-perhydroisoindolium tetrafluoborate (4.1 g), prepared in accordance with Example 4, in anhydrous dichloromethane (10 cc). Stirring of the reaction mixture is continued for 20 hours at ambient temperature; the reaction mixture is diluted with dichloromethane (20 cc) and treated with a saturated aqueous solution (20 cc) of potassium carbonate. The precipitate present is removed by filtration and the organic phase is then dried over magnesium sulphate and concentrated to dryness under reduced pressure (2.7 kPa). The residue is crystallized from acetonitrile (15 cc); the crystals obtained are drained, washed with acetonitrile (5 cc) and dried. (3aRS,7aRS)-2-[α-(3-methoxybenzyl)iminophenethyl]-7,7-diphenyl-4-perhydroisoindolone (2.7 g) melting at 127° C. is obtained.

EXAMPLE 24

4-Methoxybenzylamine (1.1 cc) is added to a stirred suspension of (3aRS,7aRS)-2-[(1-ethoxy-2-phenyl)ethylidene]-4-oxo-7,7-diphenyl-perhydroisoindolium tetrafluoborate (4.5 g), prepared in accordance with Example 4, in anhydrous dichloromethane (10 cc). Stirring of the reaction mixture is continued for 20 hours at ambient temperature; the reaction mixture is diluted with dichloromethane (20 cc) and treated with a saturated aqueous solution (20 cc) of potassium carbonate. The precipitate present is removed by filtration and the organic phase is then dried over magnesium sulphate and concentrated to dryness under reduced pressure (2.7 kPa). The residue is crystallized from acetonitrile (15 cc); the crystals obtained are drained, washed with acetonitrile (5 cc) and dried. (3aRS,7aRS)-2-[α-(4-methoxybenzyl)iminophenethyl]-7,7-diphenyl-4-perhydroisoindolone (2.7 g) melting at 158° C. is obtained.

EXAMPLE 25

4-Dimethylaminobenzylamine (1.4 g) is added to a stirred suspension of (3aRS,7aRS)-2-[(1-ethoxy-2-phenyl)ethylidene]-4-oxo-7,7-diphenyl-perhydroisoindolium tetrafluoborate (5 g), prepared in accordance with Example 4, in anhydrous dichloromethane (10 cc). Stirring of the reaction mixture is continued for 20 hours at ambient temperature and the reaction mixture is then treated with a saturated aqueous solution (20 cc) of potassium carbonate. The precipitate present is removed by filtration and the organic phase is then dried over magnesium sulphate and concentrated to dryness under reduced pressure (2.7 kPa). The residue is crystallized from acetonitrile (5 cc); the crystals obtained are drained, washed with acetonitrile (5 cc) and dried. (3aRS,7aRS)-2-[α-(4-dimethylaminobenzylimino)phenethyl]-7,7-diphenyl-4-perhydroisoindolone (3.5 g) melting at 186° C. is obtained.

EXAMPLE 26

1-Aminomethylnaphthalene (1.4 cc) is added to a stirred suspension of (3aRS,7aRS)-2-[(1-ethoxy-2-phenyl)ethylidene]-4-oxo-7,7-diphenyl-perhydroisoindolium tetrafluoborate (5 g), prepared in accordance with Example 4, in anhydrous dichloromethane (10 cc). Stirring of the reaction mixture is continued for 20 hours at ambient temperature and the reaction mixture is then treated with a saturated aqueous solution (20 cc) of potassium carbonate. The precipitate present is removed by filtration and the organic phase is then dried over magnesium sulphate and concentrated to dryness under reduced pressure (2.7 kPa). The residue is crystallized from acetonitrile (15 cc); the crystals obtained are drained, washed with acetonitrile (10 cc) and dried. (3aRS,7aRS)-2-[α-(1-naphthylmethyl)iminophenethyl]-7,7-diphenyl-4-perhydroisoindolone (3.2 g) melting at 192° C. is obtained.

EXAMPLE 27

2-Aminomethylthiophene (1 cc) is added to a stirred suspension of (3aRS,7aRS)-2-[(1-ethoxy-2-phenyl)ethylidene]-4-oxo-7,7-diphenyl-perhydroisoindolium tetrafluoborate (5 g), prepared in accordance with Example 4, in anhydrous dichlormethane (10 cc). Stirring of the reaction mixture is continued for 20 hours at ambient temperature and the reaction mixture is then treated with a saturated aqueous solution (20 cc) of potassium carbonate. The precipitate present is removed by filtration and the organic phase is then dried over magnesium sulphate and concentrated to dryness under reduced pressure (2.7 kPa). The residue is crystallized from acetonitrile (5 cc); the crystals obtained are drained, washed with acetonitrile (5 cc) and dried. (3aRS,7aRS)-2-[α-(2-thienylmethyl)iminophenethyl]-4-perhydroisoindolone (2.5 g) melting at 114° C. is obtained.

EXAMPLE 28

Furfurylamine (0.85 cc) is added to a stirred suspension of (3aRS,7aRS)-2-[(1-ethoxy-2-phenyl)ethylidene]-4-oxo-7,7-diphenyl-perhydroisoindolium tetrafluoborate (5 g), prepared in accordance with Example 4, in anhydrous dichloromethane (10 cc). Stirring of the reaction mixture is continued for 20 hours at ambient temperature and the reaction mixture is then treated with a saturated aqueous solution (20 cc) of potassium carbonate. The precipitate present is removed by filtration and the organic phase is then dried over magnesium sulphate and concentrated to dryness under reduced pressure (2.7 kPa). The residue is crystallized from petroleum ether (100 cc); the crystals obtained are drained and dried. The crystals are recrystallized from acetonitrile (10 cc); the crystals obtained are drained, washed with acetonitrile (10 cc) and dried. (3aRS,7aRS)-2-[α-(2-furylmethyl)iminophenethyl]-7,7-diphenyl-4-perhydroisoindolone (1.7 g) melting at 128° C. is obtained.

EXAMPLE 29

2-Aminomethylpyridine (0.9 cc) is added to a stirred suspension of (3aRS,7aRS)-2-[(1-ethoxy-2-phenyl)ethylidene]-4-oxo-7,7-diphenyl-perhydroisoindolium tetrafluoborate (4.5 g), prepared in accordance with Example 4, in anhydrous dichloromethane (10 cc). Stirring of the reaction mixture is continued for 20 hours at ambient temperature; the reaction mixture is treated with a saturated aqueous solution (20 cc) of potassium carbonate. The precipitate present is removed by filtration and the organic phase is then dried over magnesium sulphate and concentrated to dryness under reduced pressure (2.7 kPa). The residue is crystallized from a mixture of acetonitrile (3 cc) and isopropyl ether (5 cc); the crystals obtained are drained, washed with acetonitrile (5 cc) and dried. (3aRS,7aRS)-7,7-diphenyl-2-[α-(2-pyridylmethyl)iminophenethyl]-4-perhydroisoindolone (2 g) melting at 180° C. is obtained.

EXAMPLE 30

3-Aminomethylpyridine (0.9 cc) is added to a stirred suspension of (3aRS,7aRS)-2-[(1-ethoxy-2-phenyl)ethylidene]-4-oxo-7,7-diphenyl-perhydroisoindolium tetrafluoborate (4.5 g), prepared in accordance with Example 4, in anhydrous dichloromethane (10 cc). Stirring of the reaction mixture is continued for 20 hours at ambient temperature; the reaction mixture is treated with a saturated aqueous solution (20 cc) of potassium carbonate. The precipitate present is removed by filtration and the organic phase is then dried over magnesium sulphate and concentrated to dryness under reduced pressure (2.7 kPa). The residue is crystallized from a mixture of acetonitrile (3 cc) and isopropyl ether (5 cc);

the crystals obtained are drained, washed with acetonitrile (5 cc) and dried. (3aRS,7aRS)-7,7-diphenyl-2-[α-(3-pyridylmethyl)iminophenethyl]-4-perhydroisoindolone (1.7 g) melting at 102° C. is obtained.

EXAMPLE 31

4-Aminomethylpyridine (0.9 cc) is added to a stirred suspension of (3aRS,7aRS)-2-[(1-ethoxy-2-phenyl)ethylidene]-4-oxo-7,7-diphenyl-perhydroisoindolium tetrafluoborate (4.5 g), prepared in accordance with Example 4, in anhydrous dichloromethane (20 cc). Stirring of the reaction mixture is continued for 20 hours at ambient temperature; the reaction mixture is treated with a saturated aqueous solution (20 cc) of potassium carbonate. The precipitate present is removed by filtration and the organic phase is then dried over magnesium sulphate and concentrated to dryness under reduced pressure (2.7 kPa). The residue is crystallized from a mixture of acetonitrile (5 cc) and isopropyl ether (5 cc); the crystals obtained are drained, washed with acetonitrile (5 cc) and dried. They are recrystallized from acetonitrile (5 cc). The crystals obtained are drained and dried. (3aRS,7aRS)-7,7-diphenyl-2-[α-(4-pyridylmethyl)iminophenelethyl]-4-perhydroisoindolone (2.3 g) melting at 150° C. is obtained.

EXAMPLE 32

N,N-Dimethylhydrazine (0.53 cc) is added to a stirred suspension of (3aRS,7aRS)-2-[(1-ethoxy-2-phenyl)ethylidene]-4-oxo-7,7-diphenyl-perhydroisoindolium tetrafluoborate (3.75 g), prepared in accordance with Example 4, in anhydrous dichloromethane (40 cc), cooled to +5° C. The reaction mixture is stirred for 1 hour at +5° C. and then for 20 hours at ambient temperature; it is treated with a saturated aqueous solution (30 cc) of potassium carbonate. The precipitate present is removed by filtration and the organic phase is then washed with distilled water (30 cc), dried over magnesium sulphate and concentrated to dryness under reduced pressure (2.7 kPa). The residue is chromatographed on a Péchiney CBT1 neutral alumina gel column (diameter 3 cm, height 30 cm), eluting with a mixture of cyclohexane and ethyl acetate (50/50 by volume) and collecting 60 cc fractions. Fraction 2 is concentrated to dryness under reduced pressure (2.7 kPa). The residue is recrystallized from acetonitrile (10 cc); the crystals obtained are drained. The recrystallization liquors are concentrated to dryness under reduced pressure (2.7 kPa); the residue is crystallized from isopropyl ether (5 cc); the crystals are drained and dried. (3aRS,7aRS)-2-[(1-N,N-dimethylhydrazono-2-phenyl)ethyl]-7,7-diphenyl-4-perhydroisoindolone (0.22 g) melting at 142° C. is obtained.

EXAMPLE 33

N,N'-Carbonyldiimidazole (1.14 g) is added to a solution of 2-fluorophenylacetic acid (1.08 g) in dry dichloromethane (30 cc) cooled to +5° C. The mixture is stirred for 20 minutes at +5° C. and a solution of (3aRS,7aRS)-7,7-diphenyl-4-perhydroisoindolone hydrochloride (2.3 g) and triethylamine (1.98 cc) in dichloromethane (20 cc) is then added. The reaction mixture is stirred at 20° C. for 72 hours and then washed with water (2×150 cc), dried over magnesium sulphate and filtered and the filtrate is concentrated to dryness under reduced pressure (2.7 kPa). The solid obtained is crystallized from a mixture of acetonitrile (30 cc) and isopropyl ether (50 cc). The crystals are drained, washed with isopropyl ether and dried. (3aRS,7aRS)-7,7-diphenyl-2-[(2-fluorophenyl)acetyl]-4-perhydroisoindolone (1.53 g) is obtained in the form of white crystals melting at 186° C.

EXAMPLE 34

N,N'-Carbonyldiimidazole (1.13 g) is added to a solution of 2-(4-fluorophenyl)acetic acid (1.08 g) in dry dichloromethane (30 cc), cooled to +5° C. The mixture is stirred for 1 hour at +5° C. and a solution of 7,7-diphenyl-4-perhydroisoindolone hydrochloride (2.3 g) and triethylamine (0.98 cc) in dichloromethane (40 cc) is then added. The reaction mixture is stirred for 1 hour at +5° C. and then for 16 hours at 20° C. The reaction mixture is washed with distilled water (3×50 cc), dried over magnesium sulphate and filtered and the filtrate is concentrated to dryness under reduced pressure (2.7 kPa). The residue is recrystallized form acetonitrile (5 cc). The crystals are drained, washed with isopropyl ether (10 cc) and dried. (3aRS,7aRS)-2-[(4-fluorophenyl)acetyl]-7,7-diphenyl-4-perhydroisoindolone (2 g) melting at 210° C. is obtained.

EXAMPLE 35

N,N'-Carbonyldiimidazole (1.13 g) is added to a solution of 2-(2,6-difluorophenyl)acetic acid (1.2 g) in dry dichloromethane (30 cc), cooled to +5° C. The mixture is stirred for 45 minutes at +5° C. and a solution of (3aRS,7aRS)-7,7-diphenyl-4-perhydroisoindolone hydrochloride (2.3 g) and triethylamine (0.98 cc) in dichloromethane (40 cc) is then added. The reaction mixture is stirred at 20° C. for 16 hours, then washed with distilled water (2×50 cc), dried over magnesium sulphate and filtered and the filtrate is concentrated to dryness under reduced pressure (2.7 kPa). The residue is crystallized from ethyl acetate (10 cc). The crystals obtained are drained, washed with isopropyl ether (10 cc) and dried. (3aRS,7aRS)-2-[(2,6-difluorophenyl)acetyl]-7,7-diphenyl-4-perhydroisoindolone (2.1 g) melting at 218° C. is obtained.

EXAMPLE 36

N,N'-Carbonyldiimidazole (1.13 g) is added to a solution of 2-chlorophenylacetic acid (1.19 g) in dry dichloromethane (30 cc), cooled to +5° C. The mixture is stirred for 15 minutes at +5° C. and a solution of (3aRS,7aRS)-7,7-diphenyl-4-perhydroisoindolone hydrochloride (2.28 g) and triethylamine (1.96 cc) in dichloromethane (20 cc) is then added. The reaction mixture is stirred at 20° C. for 2.5 hours, then washed with water (2×150 cc), dried over magnesium sulphate and filtered and the filtrate is concentrated to dryness under reduced pressure (2.7 kPa). The solid obtained is crystallized from a mixture of acetonitrile (25 cc) and isopropyl ether (25 cc). The crystals are drained, washed with isopropyl ether and dried. (3aRS,7aRS)-7,7-diphenyl-2-[(2-chlorophenyl)acetyl]-4-perhydroisoindolone (1.9 g) is obtained in the form of white crystals melting at 206° C.

EXAMPLE 37

N,N'-Carbonyldiimidazole (1.13 g) is added to a solution of 3-chlorophenylacetic acid (1.19 g) in dry dichloromethane (30 cc), cooled to +5° C. The mixture is stirred for 15 minutes at +5° C. and a solution of (3aRS,7aRS)-7,7-diphenyl-4-perhydroisoindolone hydrochloride (2.28 g) and triethylamine (1.96 cc) in dichloromethane (20 cc) is then added. The reaction mixture is stirred at 20° C. for 16 hours, then washed with water (2×150 cc), dried over magnesium sulphate and filtered and the filtrate is concentrated to dryness under reduced pressure (2.7 kPa). The meringue obtained is crystallized from a mixture of acetonitrile (30 cc) and isopropyl ether (100 cc). The crystals are drained, washed with isopropyl ether and dried. (3aRS,7aRS)-7,7-diphenyl-2-[(3-chlorophenyl)acetyl]-4-perhydroisoindolone (2.2 g) is obtained in the form of white crystals melting at 179° C.

EXAMPLE 38

N,N'-Carbonyldiimidazole (1.3 g) is added to a solution of 2-(4-chlorophenyl)acetic acid (1.36 g) in dry dichloromethane (30 cc), cooled to +5° C. The mixture is stirred for 1 hour at +5° C. and a solution of (3aRS,7aRS)-7,7-diphenyl-4-perhydroisoindolone hydrochloride (2.62 g) and triethylamine (1.12 cc) in dichloromethane (20 cc) is then added. The reaction mixture is stirred for 2 hours at +5° C. and 16 hours at 20° C.; it is washed with distilled water (3×50 cc), dried over magnesium sulphate and filtered and the filtrate is concentrated to dryness under reduced pressure (2.7 kPa). The residue is crystallized from a mixture of acetonitrile (5 cc) and isopropyl ether (10 cc). The crystals obtained are drained and dried. The residue is recrystallized from acetonitrile (40 cc). The crystals obtained are drained, washed with isopropyl ether (10 cc) and dried. (3aRS,7aRS)-2-[(4-chlorophenyl)acetyl]-7,7-diphenyl-4-perhydroisoindolone (2.4 g) melting at 213° C. is obtained.

EXAMPLE 39

N,N'-Carbonyldiimidazole (1.13 g) is added to a solution of 2-(2,6-dichlorophenyl)acetic acid (1.43 g) in dry dichloromethane (30 cc), cooled to +5° C. The mixture is stirred for 30 minutes at +5° C. and a solution of (3aRS,7aRS)-7,7-diphenyl-4-perhydroisoindolone hydrochloride (2.3 g) and triethylamine (0.98 cc) in dichloromethane (40 cc) is then added. The reaction mixture is stirred at 20° C. for 20 hours, then washed with distilled water (3×50 cc), dried over magnesium sulphate and filtered and the filtrate is concentrated to dryness under reduced pressure (2.7 kPa). The residue is chromatographed on a silica gel column (0.2–0.063 mm, diameter 1.8 cm, height 23.5 cm), eluting with dichloromethane and collecting 15 cc fractions. Fractions 1 and 2 are combined and concentrated to dryness under reduced pressure (2.7 kPa). The residue is crystallized from a mixture of acetonitrile (5 cc) and isopropyl ether (4 cc). The crystals obtained are drained, washed with isopropyl ether (10 cc) and dried. (3aRS,7aRS)-2-[(2,6-dichlorophenyl)acetyl]-7,7-diphenyl-4-perhydroisoindolone (0.62 g) melting at 201° C. is obtained.

EXAMPLE 40

N,N'-Carbonyldiimidazole (1.13 g) is added to a solution of 2-(2-bromophenyl)acetic acid (1.5 g) in dry dichloromethane (30 cc), cooled to +5° C. The mixture is stirred for 45 minutes at +5° C. and a solution of (3aRS,7aRS)-7,7-diphenyl-4-perhydroiso-indolone hydrochloride (2.3 g) and triethylamine (0.98 cc) in dichloromethane (40 cc) is then added. The reaction mixture is stirred for 4 hours at 20° C. The reaction mixture is washed with distilled water (3×50 cc), dried over magnesium sulphate and filtered and the filtrate is concentrated to dryness under reduced pressure (2.7 kPa). The residue is recrystallized from acetonitrile (74 cc). The crystals are drained, washed with isopropyl ether (10 cc) and dried. (3aRS,7aRS)-2-[(2-bromophenyl)acetyl]-7,7-diphenyl-4-perhydroisoindolone (2.04 g) melting at 217° C. is obtained.

EXAMPLE 41

N,N'-Carbonyldiimidazole (1.14 g) is added to a solution of 2-hydroxyphenylacetic acid (1.06 g) in dry dichloromethane (30 cc), cooled to +5° C. The mixture is stirred for 30 minutes at +5° C. and a solution of (3aRS,7aRS)-7,7-diphenyl-4-perhydroisoindolone hydrochloride (2.23 g) and triethylamine (1.96 cc) in dichloromethane (20 cc) is then added. The reaction mixture is stirred at 20° C. for 16 hours, then washed with water (2×100 cc), dried over magnesium sulphate and filtered and the filtrate is concentrated to dryness under reduced pressure (2.7 kPa). The residue is chromatographed on a silica gel column (0.2–0.063 mm, diameter 4 cm, height 40 cm), eluting under a nitrogen pressure of 0.7 bar with a mixture of cyclohexane and ethyl acetate (70/30 by volume) and collecting 125 cc fractions. Fractions 4 to 11 are combined and concentrated to dryness under reduced pressure (2.7 kPa). The residue is crystallized from a mixture of acetonitrile (15 cc) and isopropyl ether (30 cc). The crystals are drained, washed with isopropyl ether and dried. (3aRS,7aRS)-7,7-diphenyl-2-[(2-hydroxyphenyl)acetyl]-4-perhydroisoindolone (0.8 g) is obtained in the form of white crystals melting at 232° C.

EXAMPLE 42

N,N'-Carbonyldiimidazole (1.13 g) is added to a solution of 2-(2-methylphenyl)acetic acid (1.05 g) in dry dichloromethane (30 cc), cooled to +5° C. The mixture is stirred for 40 minutes at +5° C. and a solution of (3aRS,7aRS)-7,7-diphenyl-4-perhydroisoindolone hydrochloride (2.3 g) and triethylamine (0.98 cc) in dichloromethane (20 cc) is then added. The reaction mixture is stirred at 20° C. for 16 hours, then washed with distilled water (2×50 cc), dried over magnesium sulphate and filtered and the filtrate is concentrated to dryness under reduced pressure (2.7 kPa). The residue is chromatographed on a silica gel column (0.2–0.063 mm, diameter 2 cm, height 16 cm), eluting with ethyl acetate and collecting 45 cc fractions. Fractions 2 to 4 are combined and concentrated to dryness under reduced pressure (2.7 kPa). The residue is recrystallized from a mixture of acetonitrile (8 cc) and isopropyl ether (7.5 cc). The crystals are drained, washed with isopropyl ether (10 cc) and dried. (3aRS,7aRS)-2-[(2-methylphenyl)acetyl]-7,7-diphenyl-4-perhydroisoindolone (1.25 g) melting at 196° C. is obtained.

EXAMPLE 43

N,N'-Carbonyldiimidazole (1.13 g) is added to a solution of 2-(3-methylphenyl)acetic acid (1.05 g) in dry dichloromethane (30 cc), cooled to +5° C. The mixture is stirred for 35 minutes at +5° C. and a solution of (3aRS,7aRS)-7,7-diphenyl-4-perhydroisoindolone hydrochloride (2.3 g) and triethylamine (0.98 cc) in dichloromethane (20 cc) is then added. The reaction mixture is stirred at 20° C. for 16 hours, then washed with distilled water (2×50 cc), dried over magnesium sulphate and filtered and the filtrate is concentrated to dryness under reduced pressure (2.7 kPa). The residue is crystallized by dissolving in boiling ethyl acetate (10 cc). The crystals are drained, dried and recrystallized from a mixture of acetonitrile (8 cc) and isopropyl ether (7.5 cc). The crystals are drained, washed with isopropyl ether (10 cc) and dried. (3aRS,7aRS)-2-[(3-methylphenyl)acetyl]-7,7-diphenyl-4-perhydroisoindolone (1.37 g) melting at 184° C. is obtained.

EXAMPLE 44

N,N'-Carbonyldiimidazole (1.13 g) is added to a solution of 3-(trifluoromethyl)phenylacetic acid (1.43 g) in dry dichloromethane (30 cc), cooled to +5° C. The mixture is stirred for 15 minutes at +5° C. and a solution of (3aRS,7aRS)-7,7-diphenyl-4-perhydroisoindolone hydrochloride (2.28 g) and triethylamine (1.96 cc) in dichloromethane (20 cc) is then added. The reaction mixture is stirred at 20° C. for 2 hours, then washed with water (2×150 cc), dried over magnesium sulphate and filtered and the filtrate is concentrated to dryness under reduced pressure (2.7 kPa). The meringue obtained is crystallized from a mixture of acetonitrile (30 cc) and isopropyl ether (30 cc). The crystals are drained, washed with isopropyl ether and dried. (3aRS,7aRS)-7,7-diphenyl-2-[(3-(trifluoromethyl)phenyl)acetyl]-4-perhydroisoindolone (2 g) is obtained in the form of white crystals melting at 184° C.

EXAMPLE 45

N,N'-Carbonyldiimidazole (1.13 g) is added to a solution of 2-(2-(trifluoromethyl)phenyl)acetic acid (1.42 g) in dry dichloromethane (30 cc), cooled to +5° C. The mixture is stirred for 1 hour 45 minutes at +5° C. and a solution of (3aRS,7aRS)-7,7-diphenyl-4-perhydroisoindolone hydrochloride (2.3 g) and triethylamine (0.98 cc) in dichloromethane (40 cc) is then added. The reaction mixture is stirred at 20° C. for 18 hours, then washed with distilled water (3×50 cc), dried over magnesium sulphate and filtered and the filtrate is concentrated to dryness under reduced pressure (2.7 kPa). The residue is crystallized from acetonitrile (10 cc). The crystals obtained are drained, washed with isopropyl ether (10 cc) and dried. (3aRS,7aRS)-7,7-diphenyl-2-[(2-(trifluoromethyl)phenyl)acetyl]-4-perhydroisoindolone (1.68 g) melting at 207° C. is obtained.

EXAMPLE 46

N,N'-Carbonyldiimidazole (0.37 g) is added to a solution of 2-(tert-butoxycarbonylaminomethyl)phenylacetic acid (0.6 g) in dry dichloromethane (20 cc), cooled to +5° C. The mixture is stirred for 30 minutes at +5° C. and a solution of (3aRS,7aRS)-7,7-diphenyl-4-perhydroisoindolone hydrochloride (0.75 g) and triethylamine (0.6 cc) in dichloromethane (20 cc) is then added. The reaction mixture is stirred at 20° C. for 16 hours, then washed with water (2×100 cc), dried over magnesium sulphate and filtered and the filtrate is concentrated to dryness under reduced pressure (2.7 kPa). (3aRS,7aRS)-2-[(2-(tert-butoxycarbonylaminomethyl)phenyl)acetyl]-7,7-diphenyl-4-perhydroisoindolone (105 g) is obtained in the form of a white meringue.

(3aRS,7aRS)-2-[(2-(tert-butoxycarbonylaminomethyl)phenyl)acetyl]-7,7-diphenyl-4-perhydroisoindolone (1 g) is treated with a 5.7N solution (10 cc) of hydrochloric acid in dry dioxane at 20° C. for 16 hours. The reaction mixture is concentrated to dryness under reduced pressure (2.7 kPa) and the residue is solidified by scratching with isopropyl ether and reprecipitated by cooling a solution in boiling acetonitrile (20 cc). The solid is drained, washed with isopropyl ether and dried. The solid is dissolved in water, the solution is filtered, rendered alkaline to pH 10 by the action of a decinormal sodium hydroxide solution and extracted with ethyl acetate. The organic phase is dried over magnesium sulphate and filtered and the filtrate is treated with a 3N solution (1 cc) of hydrochloric acid in dioxane. The precipitate is drained, washed with isopropyl ether and dried. (3aRS,7aRS)-2-[(2-aminomethylphenyl)acetyl]-7,7-diphenyl-4-perhydroisoindolone (0.5 g) is obtained in the form of a cream-white solid.

Proton NMR spectrum: At ambient temperature, the mixture of the two rotamers is observed: 2 to 2.35 (Mt, 2H, —CH$_2$— in 5 or 6); 2.65 to 3.15 (Mt, 4H, —CH$_2$— in 1 and —CH$_2$— in 6 or 5); 3.20 to 4.5 (Mt, —CH$_2$— in 3, —CH— in 3a, —CH— in 7, —N—CO—CH$_2$— and —CH$_2$N—); 7.05 to 7.7 (Mt, 14H, aromatic).

Infrared spectrum (KBr), characteristic bands (cm$^{-1}$): 3600–3250, 3100–3000, 3000–2800, 2750–2250, 1715, 1620, 1600, 1580, 1495, 1475, 1445, 1440, 755, 703.

2-(tert-Butoxycarbonylaminomethyl)phenyl acetic acid is prepared by the method described in Japanese Patent Application 74 24 975.

EXAMPLE 47

N,N'-Carbonyldiimidazole (1.13 g) is added to a solution of 2-methoxyphenylacetic acid (1.16 g) in dry dichloromethane (30 cc), cooled to +5° C. The mixture is stirred for 15 minutes at +5° C. and a solution of (3aRS,7aRS)-7,7-diphenyl-4-perhydroisoindolone hydrochloride (2.28 g) and triethylamine (1.96 cc) in dichloromethane (20 cc) is then added. The reaction mixture is stirred at 20° C. for 16 hours, then washed with water (2×150 cc), dried over magnesium sulphate and filtered and the filtrate is concentrated to dryness under reduced pressure (2.7 kPa). The meringue obtained is crystallized from a mixture of acetonitrile (30 cc) and isopropyl ether (30 cc). The crystals are drained, washed with isopropyl ether (25 cc) and dried. (3aRS,7aRS)-7,7-diphenyl-2-[(2-methoxyphenyl)acetyl]-4-perhydroisoindolone (2 g) is obtained in the form of white crystals melting at 163° C.

EXAMPLE 48

Triethyloxonium tetrafluoborate (2.35 g) is added to a solution of (3aRS,7aRS)-7,7-diphenyl-2-[(2-methoxyphenyl)acetyl]-4-perhydroisoindolone (5 g) in dichloromethane (10 cc). Stirring of the reaction mixture is continued for 20 hours at ambient temperature; the reaction mixture is then treated with ether (100 cc) and the precipitate obtained is drained, washed with ether (100 cc) and dried. (3aRS,7aRS)-2-[(1-ethoxy-2-(2-methoxyphenyl))ethylidene]-4-oxo-7,7-diphenyl-perhydroisoindolium tetrafluoborate (5.75 g) is obtained in the form of a yellow powder used in the crude state for the following operation.

A 5.4N ethanolic ammonia solution (1.3 cc) is added to a stirred suspension of (3aRS,7aRS)-2-[(1-ethoxy-2-(2-methoxyphenyl))ethylidene]-4-oxo-7,7-diphenyl-perhydroisoindolium tetrafluoborate (5.7 g) in anhydrous dichloromethane (15 cc), which is cooled to to −10° C. The temperature of the reaction mixture is then allowed to rise to ambient temperature and stirring is continued for 20 hours. The reaction mixture is diluted with dichloromethane (20 cc) and treated with a 10% aqueous solution (20 cc) of potassium carbonate. The precipitate present is removed by filtration and the organic phase is then washed with distilled water (25 cc) and with a saturated aqueous solution (25 cc) of sodium chloride, dried over magnesium sulphate and concentrated to dryness under reduced pressure (2.7 kPa). The residue is crystallized from acetonitrile (10 cc). The crystals obtained are drained, washed with acetonitrile (10 cc) and dried. (3aRS,7aRS)-2-[1-imino-2-(2-methoxyphenyl)ethyl]-7,7-diphenyl-4-perhydroisoindolone (1 g) melting at a temperature higher than 260° C. is obtained.

EXAMPLE 49

N,N'-Carbonyldiimidazole (1 g) is added to a solution of 2-methoxyphenylacetic acid (1 g) in dry dichloromethane (30 cc), cooled to +5° C. The mixture is stirred for 40 minutes at +5° C. and a solution of (3aRS,7aRS)-7,7-diphenyl-4-perhydroisoindolone hydrochloride (2 g) and triethylamine (1.7 cc) in dichloromethane (40 cc) is then added. The reaction mixture is stirred at 20° C. for 16 hours, then washed with water (2×50 cc), dried over magnesium sulphate and filtered and the filtrate is concentrated to dryness under reduced pressure (2.7 kPa). The residue is chromatographed on a silica gel column (0.2–0.063 mm, diameter 1.8 cm, height 13 cm), eluting with ethyl acetate and collecting 25 cc fractions. Fractions 3 to 5 are combined and concentrated to dryness under reduced pressure (2.7 kPa). The residue is crystallized from a mixture of acetonitrile (5 cc) and isopropyl ether (10 cc). The crystals are drained, washed with isopropyl ether (25 cc) and dried. (3aR,7aR)-(-)-7,7-diphenyl-2-[(2-methoxyphenyl)acetyl]-4-perhydroisoindolone (1.7 g) is obtained in the form of white crystals melting at 200° C.; $[\alpha]^{20}_D = -274°$ (c=0.49, acetic acid).

EXAMPLE 50

Triethyloxonium tetrafluoborate (4 g) is added to a solution of (3aR,7aR)-7,7-diphenyl-2-[(2-methoxyphenyl)acetyl]-4-perhydroisoindolone (7.7 g) in anhydrous dichloromethane (13 cc). Stirring of the reaction mixture is continued for 20 hours at ambient temperature; the mixture is then cooled to −15° C. and a 5.4N ethanolic ammonia solution (2.6 cc) is then added. The temperature of the reaction mixture is allowed to rise to ambient temperature and stirring is continued for 5 hours and a half. The reaction mixture is treated with a 10% aqueous solution (20 cc) of potassium carbonate; the precipitate formed is drained and washed with dichloromethane (10 cc). The organic phases are combined, dried over magnesium sulphate and concentrated to dryness under reduced pressure (2.7 kPa). The residue is crystallized from acetonitrile (10 cc); the crystals obtained are drained, washed with acetonitrile (5 cc) and with isopropyl ether (10 cc) and dried. They are then chromatographed on a Péchiney CBT1 neutral alumina gel column (diameter 4.5 cm, height 28 cm), eluting with a mixture (200 cc) of 1,2-dichloroethane and methanol (98/2 by volume) and then with a mixture of 1,2-dichloroethane and methanol (90/10 by volume), collecting 25 cc fractions. Fractions 8 to 31 are combined and concentrated to dryness under reduced pressure (2.7 kPa). The residue is crystallized from acetonitrile (10 cc); the crystals obtained are drained and dried. (3aR,7aR)-2-[1-imino-2-(2-methoxyphenyl)ethyl]-7,7-diphenyl-4-perhydroisoindolone (1.6 g) melting at 190° C. is obtained; $[\alpha]^{20}_D = -254°$ (c=1, methanol).

EXAMPLE 51

N,N'-Carbonyldiimidazole (1.13 g) is added to a solution of 2-methoxyphenylacetic acid (1.16 g) in dry dichloromethane (30 cc), cooled to +5° C. The mixture is stirred for 15 minutes at +5° C. and a solution of (3aRS,7aRS)-7,7-diphenyl-4-perhydroisoindolone hydrochloride (2.28 g) and triethylamine (1.96 cc) in dichloromethane (20 cc) is then added. The reaction mixture is stirred at 20° C. for 16 hours, then washed with water (2×150 cc), dried over magnesium sulphate and filtered and the filtrate is concentrated to dryness under reduced pressure (2.7 kPa). The meringue obtained is crystallized from a mixture of acetonitrile (30 cc) and isopropyl ether (80 cc). The crystals are drained, washed with isopropyl ether and dried. (3aRS,7aRS)-7,7-diphenyl-2-[(2-methoxyphenyl)-acetyl]-4-perhydroisoindolone (2 g) is obtained in the form of white crystals melting at 158° C.

EXAMPLE 52

N,N'-Carbonyldiimidazole (0.52 g) is added to a solution of 2-(2,6-dimethoxyphenyl)acetic acid (0.63 g) in dry dichloromethane (20 cc), cooled to +5° C. The mixture is stirred for 35 minutes at +5° C. The mixture is stirred for 35 minutes at +5° C. and a solution of (3aRS,7aRS)-7,7-diphenyl-4-perhydroisoindolone hydrochloride (1.05 g) and triethylamine (0.44 cc) in dichloromethane (25 cc) is then added. The reaction mixture is stirred at 20° C. for 16 hours, then washed with distilled water (2×50 cc), dried over magnesium sulphate and filtered and the filtrate is concentrated to dryness under reduced pressure (2.7 kPa). The residue is crystallized from a mixture of acetonitrile (16 cc) and isopropyl ether (15 cc). The crystals are drained, washed with isopropyl ether (10 cc) and dried. (3aRS,7aRS)-2-[(2,6-dimethoxyphenyl)acetyl]-7,7-diphenyl-4-perhydroisoindolone (0.89 g) melting at 224° C. is obtained.

2-(2,6-Dimethoxyphenyl)acetic acid can be prepared in the following way:

A mixture of N-[2-(2,6-dimethoxyphenyl)thioacetyl]-morpholine and a 10% aqueous potassium hydroxide solution (40 cc) is refluxed for 12 hours. After return to ambient temperature, the reaction mixture is extracted with ethyl acetate (100 cc); the organic phase is acidified by addition of 4N hydrochloric acid (25 cc). The aqueous phase is extracted with ethyl acetate (2×100 cc). The organic phases are combined and washed with distilled water (3×100 cc), dried over magnesium sulphate and filtered and the filtrate is concentrated to dryness under reduced pressure (2.7 kPa). The residue is recrystallized from a mixture of cyclohexane (20 cc) and ethyl acetate (10 cc). The crystals obtained are drained, washed with isopropyl ether (2×15 cc) and dried. 2-(2,6-Dimethoxyphenyl)acetic acid (0.63 g) melting at 156° C. is obtained.

N-[2-(2,6-Dimethoxyphenyl)thioacetyl]-morpholine can be prepared in the following way:

A mixture of 2,6-dimethoxyacetophenone (39.5 g), morpholine (19 cc) and sulphur (7 g) is refluxed, with stirring, for 24 hours. After return to ambient temperature, the reaction mixture is poured onto ice. The mixture is extracted with ethyl acetate (100 cc); the organic solution is washed with distilled water (3×100 cc), dried over magnesium sulphate and concentrated to dryness under reduced pressure (2.7 kPa). The residue is chromatographed on a silica gel column (0.2–0.063 mm, diameter 4.3 cm, height 48 cm), eluting with a mixture of cyclohexane and ethyl acetate (90/10 by volume) and collecting 100 cc fractions. Fractions 61 to 72 are combined and concentrated to dryness under reduced pressure (2.7 kPa). N-[2-(2,6-Dimethoxyphenyl)-thioacetyl]-morpholine (2.88 g) is obtained which is used in the crude state for the subsequent syntheses.

EXAMPLE 53

N,N'-Carbonyldiimidazole (1.14 g) is added to a solution of 2,5-dimethoxyphenylacetic acid (1.34 g) in dry dichloromethane (30 cc), cooled to +5° C. The mixture is stirred for 30 minutes at +5° C. and a solution of (3aRS,7aRS)-7,7-diphenyl-4-perhydroisoindolone hydrochloride (2.28 g) and triethylamine (1.96 cc) in dichloromethane (20 cc) is then added. The reaction mixture is stirred at 20° C. for 16 hours, then washed with water (2×200 cc), dried over magnesium sulphate and filtered and the filtrate is concentrated to dryness under reduced pressure (2.7 kPa). The meringue obtained is crystallized from a mixture of acetonitrile (20 cc) and isopropyl ether (80 cc). The crystals are drained, washed with isopropyl ether (25 cc) and dried. (3aRS,7aRS)-7,7-diphenyl-2-[(2,5-dimethoxyphenyl)acetyl]-4-perhydroisoindolone (1.5 g) is obtained in the form of white crystals melting at 209° C.

EXAMPLE 54

N,N'-Carbonyldiimidazole (0.77 g) is added to a solution of 2-methylthiophenylacetic acid (0.87 g) in dry dichloromethane (30 cc), cooled to +5° C. The mixture is stirred for 15 minutes at +5° C. and a solution of (3aRS,7aRS)-7,7-diphenyl-4-perhydroisoindolone hydrochloride (1.56 g) and triethylamine (1.34 cc) in dichloromethane (30 cc) is then added. The reaction mixture is stirred at 20° C. for 3.5 hours, then washed with water (3×100 cc), dried over magnesium sulphate and filtered and the filtrate is concentrated to dryness under reduced pressure (2.7 kPa). The residue is chromatographed on a silica gel column (0.04–0.063 mm, diameter 5 cm, height 50 cm), eluting under a nitrogen pressure of 0.5 bar with a mixture of cyclohexane and ethyl acetate (60/40 by volume) and collecting 50 cc fractions. Fractions 1 to 14 are combined and concentrated to dryness under reduced pressure (2.7 kPa). The solid obtained is recrystallized from acetonitrile (5 cc) and the crystals are drained, washed with isopropyl ether and dried. (3aRS,7aRS)-7,7-diphenyl-2-[(2-methylthiophenyl)acetyl]-4-perhydroisoindolone (1.29 g) is obtained in the form of pale yellow crystals melting at 188° C.

2-Methylthiophenylacetic acid is prepared by the method of G. Kompa et St. Weckmann (J. Prak. Chem. [2], 138, 123 (1933)).

EXAMPLE 55

N,N'-Carbonyldiimidazole (1.62 g) is added to a solution of (2-tert-butoxycarbonylaminophenyl)acetic acid (2.51 g) in dry dichloromethane (30 cc), cooled to +5° C. The mixture is stirred for 45 minutes at +5° C. and a solution of (3aRS,7aRS)-7,7-diphenyl-4-perhydroisoindolone hydrochloride (3.27 g) and triethylamine (2.8 cc) in dichloromethane (30 cc) is then added. The reaction mixture is stirred at 20° C. for 16 hours, then washed with water (3×100 cc), dried over magnesium sulphate and filtered and the filtrate is concentrated to dryness under reduced pressure (2.7 kPa). The residue is chromatographed on a silica gel column (0.2–0.063 mm, diameter 4 cm, height 40 cm), eluting under a nitrogen pressure of 0.7 bar with a mixture of cyclohexane and ethyl acetate (60/40 by volume) and collecting 125 cc fractions. Fractions 22 to 34 are combined and concentrated to dryness under reduced pressure (2.7 kPa) to give (3aRS,7aRS)-2-[(2-tert-butoxycarbonylaminophenyl)acetyl]-7,7-diphenyl-4-perhydroisoindolone (1.5 g) in the form of a yellow meringue.

(3aRS,7aRS)-2-[(2-tert-butoxycarbonylaminophenyl)acetyl]-7,7-diphenyl-4-perhydroisoindolone (1.5 g) is treated with a 5.7N solution (15 cc) of hydrochloric acid in dry dioxane at 20° C. for 4 hours. The reaction mixture is concentrated to dryness under reduced pressure (2.7 kPa) and the residue is purified by dissolving in acetonitrile (20 cc) and precipitating from isopropyl ether (30 cc). The solid is drained, washed with isopropyl ether and dried. (3aRS,7aRS)-2-[(2-aminophenyl)acetyl]-7,7-diphenyl-4-perhydroisoindolone hydrochloride (1.1 g) is obtained in the form of a slightly pink solid.

Proton NMR spectrum: At ambient temperature, the mixture of the two rotamers is observed. 2.1 and 2.27 (2Mt, respectively 1H each, —CH$_2$— in 5 or 6); 2.65 to 3.35 (Mt, 4H, —CH$_2$— in 6 or 5 and —CH$_2$— in 1); 3.4 to 3.75 (Mt, 1H of the —CH$_2$— in 3 and —CH— in 3a); 3.55 and 3.84 (2S, —N—CO—CH$_2$—); 3.9 to 4.2 (Mt, —CH— in 7a); 4.15 to 4.4 (Mt, 1H of the —CH$_2$— in 3; 7 to 7.7 (Mt, 14H, aromatic).

Infrared spectrum (KBr), characteristic bands (cm$^{-1}$): 3430, 3085, 3055, 3025, 3000–1900, 2965, 2880, 1715, 1630–1520, 1625, 1595, 1580, 1492, 1455, 1445, 755, 703.

(2-tert-Butoxycarbonylaminophenyl)acetic acid can be obtained in the following way:

A solution of (2-nitrophenyl)acetic acid (18.1 g) in normal sodium hydroxide solution (120 cc) is hydrogenated in an autoclave under a pressure of 5 bar for 2.5 hours at 20° C. in the presence of 3% palladium-on-carbon black (1.5 g). The solution of sodium (2-aminophenyl)acetate thus obtained is cooled to +5° C. and then treated with a solution of di-tert-butyl dicarbonate (26.16 g) in tetrahydrofuran (100 cc) and then with normal sodium hydroxide solution (80 cc). The reaction mixture is stirred at 20° C. for 80 hours, partially concentrated under reduced pressure (2.7 kPa), diluted with water (200 cc) and washed with ethyl ether (3×200 cc). The aqueous phase is acidified to pH 3 by addition of 4N hydrochloric acid and extracted with ethyl acetate (2×200 cc). The combined organic phases are washed with water (2×150 cc), dried over magnesium sulphate and filtered and the filtrate is concentrated to dryness under reduced pressure (2.7 kPa). (2-tert-Butoxycarbonylaminophenyl)acetic acid (25 g) is obtained in the form of a cream-white solid.

EXAMPLE 56

N,N'-Carbonyldiimidazole (1.13 g) is added to a solution of (N-tert-butoxycarbonyl-2-N-methylaminophenyl)acetic acid (1.85 g) in dry dichloromethane (30 cc), cooled to +5° C. The mixture is stirred for 30 minutes at +5° C. and a solution of (3aRS,7aRS)-7,7-diphenyl-4-perhydroisoindolone hydrochloride (2.29 g) and triethylamine (1.9 cc) in dichloromethane (20 cc) is then added. The reaction mixture is stirred at 20° C. for 2 hours, then washed with water (2×200 cc), dried over magnesium sulphate and filtered and the filtrate is concentrated to dryness under reduced pressure (2.7 kPa). The residue is chromatographed on a silica gel column (0.2–0.063 mm, diameter 4 cm, height 50 cm), eluting under a nitrogen pressure of 0.7 bar with a mixture of cyclohexane and ethyl acetate (30/70 by volume) and collecting 125 cc fractions. Fractions 22 to 34 are combined and concentrated to dryness under reduced pressure (2.7 kPa) to give (3aRS,7aRS)-2-[(N-tert-butoxycarbonylamino-2-N-methylamino-phenyl)acetyl]-7,7-diphenyl-4-perhydroisoindolone (2.8 g) in the form of a white meringue.

(3aRS,7aRS)-2-[(N-tert-butoxycarbonyl-2-N-methylamino-phenyl)acetyl]-7,7-diphenyl-4-perhydroisoindolone (2.8 g) is treated with a 5.7N solution (30 cc) of hydrochloric acid in dry dioxane at 20° C. for 4 hours. Isopropyl ether (100 cc) is added and the solid is drained, washed with isopropyl ether and dried. (3aRS,7aRS)-2-[(2-methylaminophenyl)acetyl]-7,7-diphenyl-4-perhydroisoindolone hydrochloride (2.1 g) is obtained in the form of a white solid.

Proton NMR spectrum: At ambient temperature, the mixture of the two rotamers is observed. 2.1 and 2.27 (2Mt, respectively 1H each, —CH$_2$— in 5 or 6); 2.65 to 3.35 (Mt, —CH$_2$— in 6 or 5 and —CH$_2$— in 1); 2.82 and 2.87 (2S, —NCH$_3$); 3.4 to 3.75 (Mt, 1H of the —CH$_2$— in 3 and —CH— in 3a); 3.55 and 3.85 (2S, —N—CO—CH$_2$—); 3.9 to 4.2 (Mt, —CH— in 7a); 4.15 to 4.45 (Mt, 1H of the —CH$_2$— in 6 or 5); 7 to 7.7 (Mt, 14H, aromatic).

Infrared spectrum (KBr), characteristic bands (cm$^{-1}$): 3600–3300, 3100–3000, 3000–2850, 3100–2200, 1712, 1640–1610, 1595, 1495, 1475–1410, 1445, 755, 702.

(N-tert-Butoxycarbonyl-2-N-methylamino-phenyl)acetic acid can be prepared in the following way:

A solution of methyl (N-tert-butoxycarbonyl-2-N-methylamino-phenyl)acetate (3.5 g) in ethanol (50 cc) is treated with normal sodium hydroxide solution (15 cc) at 80° C. for 4 hours. The reaction mixture is concentrated under reduced pressure (2.7 kPa). The residue is taken up in water (100 cc) and the solution, acidified to pH 1 by the action of 4N hydrochloric acid, is extracted with ethyl acetate (2×100 cc). The combined organic phases are dried over magnesium sulphate and filtered and the filtrate is concentrated to dryness under reduced pressure (2.7 kPa) to give (N-tert-butoxycarbonyl-2-N-methylamino-phenyl)acetic acid (2.85 g) in the form of a white solid.

Methyl (N-tert-butoxycarbonyl-2-N-methylaminophenyl)acetate can be prepared in the following way:

A solution of (2-tert-butoxycarbonylaminophenyl)acetic acid (5 g) in dry dimethylformamide (50 cc) is added to a suspension of sodium hydride (1.2 g) (80% dispersion in oil) in dry dimethylformamide (20 cc). The reaction mixture is heated at 80° C. for 2 hours and cooled to 20° C. Methyl iodide (2.51 cc) is added and the mixture is stirred at 20° C. for 16 hours. The mixture is diluted with water (200 cc) and extracted with ethyl acetate (2×200 cc). The combined organic phases are washed with water (100 cc), dried over magnesium sulphate and filtered and the filtrate is concentrated to dryness under reduced pressure (2.7 kPa). The residue is chromatographed on a silica gel column (0.2–0.063 mm, diameter 4 cm, height 48 cm), eluting under a nitrogen pressure of 0.7 bar with a mixture of cyclohexane and ethyl acetate (90/10 by volume) and collecting 125 cc fractions. Fractions 9 to 17 are combined and concentrated to dryness under reduced pressure (2.7 kPa) to give methyl (N-tert-butoxycarbonyl-2-N-methylaminophenyl)acetate (3.5 g) in the form of a yellow oil.

EXAMPLE 57

N,N'-Carbonyldiimidazole (0.81 g) is added to a solution of (N-tert-butoxycarbonyl-2-N-ethylaminophenyl)acetic acid (1.4 g) in dry dichloromethane (30 cc), cooled to +5° C. The mixture is stirred for 30 minutes at +5° C. and a solution of (3aRS,7aRS)-7,7-diphenyl-4-perhydroisoindolone hydrochloride (1.63 g) and triethylamine (1.4 cc) in dichloromethane (20 cc) is then added. The reaction mixture is stirred at 20° C. for 16 hours, then washed with water (2×100 cc), dried over magnesium sulphate and filtered and the filtrate is concentrated to dryness under reduced pressure (2.7 kPa). The residue is chromatographed on a silica gel column (0.2–0.063 mm, diameter 4 cm, height 35 cm), eluting under a nitrogen pressure of 0.7 bar with a mixture of cyclohexane and ethyl acetate (60/40 by volume) and collecting 125 cc fractions. Fractions 19 to 29 are combined and concentrated to dryness under reduced pressure (2.7 kPa) to give (3aRS,7aRS)-2-[(N-tert-butoxycarbonyl-2-N-ethylamino-phenyl)acetyl]-7,7-diphenyl-4-perhydroisoindolone (1.9 g) in the form of a white meringue.

(3aRS,7aRS)-2-[(N-tert-butoxycarbonyl-2-N-ethylamino-phenyl)acetyl]-7,7-diphenyl-4-perhydroisoindolone (1.8 g) is treated with a 5.7N solution (18 cc) of hydrochloric acid in dry dioxane at 20° C. for 4 hours. The reaction mixture is concentrated to dryness under reduced pressure (2.7 kPa) and the solid is stirred with isopropyl ether (100 cc), drained, washed with isopropyl ether and dried. (3aRS,7aRS)-2-[(2-ethylaminophenyl)acetyl]-7,7-diphenyl-4-perhydroisoindolone hydrochloride (1.54 g) is obtained, which is stirred with a mixture of normal sodium hydroxide solution (40 cc) and ethyl acetate (30 cc). The solid is drained, washed with water (2×10 cc) and with ethyl acetate (3×10 cc) and dried. (3aRS,7aRS)-2-[(2-ethylaminophenyl)acetyl]-7,7-diphenyl-4-perhydroisoindolone (0.85 g) is obtained in the form of a white solid.

Proton NMR spectrum: At ambient temperature, the mixture of the two rotamers is observed. 1.16 (T, 3H, —CH$_3$ of ethylamino); 2.05 and 2.23 (2Mt, respectively 1H each, —CH$_2$— in 5 or 6); 2.6 to 3.6 (Mt, —CH$_2$— in 6 or 5, —CH$_2$— in 1, —NCH$_2$— ethyl, —NCOCH$_2$—, 1H of the —CH$_2$— in 3 and —CH— in 3a); 3.9 to 4.2 (Mt, —CH— in 7a); 4.10 to 4.45 (Mt, 1H of the —CH$_2$— in 3); 6.3 to 7.7 (Mt, 14H, aromatic).

Infrared spectrum (KBr), characteristic bands (cm$^{-1}$): 3600–3300, 3465, 3105–3000, 3000–2870, 1715, 1625, 1595, 1525, 1495, 1475, 1445, 1410, 755, 705.

(N-tert-Butoxycarbonyl-2-N-ethylaminophenyl)acetic acid can be prepared in the following way:

A solution of ethyl (N-tert-butoxycarbonyl-2-N-ethylamino-phenyl)acetate (4.7 g) in ethanolamine (50 cc) is treated with normal sodium hydroxide solution (20 cc) for 4 hours under reflux. The reaction mixture is concentrated under reduced pressure (2.7 kPa). The residue is taken up in water (50 cc) and ethyl acetate (50 cc) and the aqueous phase is washed with ethyl acetate (2×100 cc), then acidified to pH 1 by the action of 4N hydrochloric acid and extracted with ethyl ether (2×100 cc). The combined organic phases are dried over magnesium sulphate and filtered and the filtrate is concentrated to dryness under reduced pressure (2.7 kPa) to give (N-tert-butoxycarbonyl-2-N-ethylaminophenyl)acetic acid (4 g) in the form of a yellow oil.

Ethyl (N-tert-butoxycarbonyl-2-N-ethylaminophenyl)acetate can be prepared in the following way:

A solution of (2-tert-butoxycarbonylaminophenyl)acetic acid (5 g) in dry dimethylformamide (50 cc) is added to a suspension of sodium hydride (1.2 g) (80% dispersion in oil) in dry dimethylformamide (20 cc). The reaction mixture is heated at 80° C. for 2 hours and cooled to 20° C. Ethyl iodide (3.25 cc) is added and the mixture is stirred at 20° C. for 16 hours. The mixture is diluted with water (200 cc) and extracted with ethyl acetate (2×200 cc). The combined organic phases are washed with water (100 cc), dried over magnesium sulphate and filtered and the filtrate is concentrated to dryness under reduced pressure (2.7 kPa). The residue is chromatographed on a silica gel column (0.2–0.063 mm), diameter 4 cm, height 40 cm), eluting under a nitrogen pressure of 0.7 bar with a mixture of cyclohexane and ethyl acetate (80/20 by volume) and collecting 125 cc fractions. Fractions 5 to 7 are combined and concentrated to dryness under reduced pressure (2.7 kPa) to give ethyl (N-tert-butoxycarbonyl-2-N-ethylamino-phenyl)acetate (4.7 g) in the form of a yellow oil.

EXAMPLE 58

N,N'-Carbonyldiimidazole (0.5 g) is added to a solution of (N-tert-butoxycarbonyl-2-N-propylamino-phenyl)acetic acid (0.9 g) in dry dichloromethane (25 cc), cooled to +5° C. The mixture is stirred at +5° C. for 30 minutes and a solution of (3aRS,7aRS)-7,7-diphenyl-4-perhydroisoindolone hydrochloride (1 g) and triethylamine (0.87 cc) in dichloromethane (15 cc) is then added. The reaction mixture is stirred at 20° C. for 3 hours, then diluted with water (75 cc) and ethyl acetate (50 cc). The organic phase is washed with water (50 cc) and saturated sodium chloride solution (75 cc), dried over magnesium sulphate and filtered and the filtrate is concentrated to dryness under reduced pressure (2.7 kPa). The residue is chromatographed on a silica gel column (0.2–0.063 mm, diameter 2.2 cm, height 25 cm), eluting with a mixture of cyclohexane and ethyl acetate (50/50 by volume) and collecting 50 cc fractions. Fractions 5 to 10 are combined and concentrated to dryness under reduced pressure (2.7 kPa) to give (3aRS,7aRS)-2-[(N-tert-butoxycarbonyl-2-N-propylamino-phenyl)acetyl]-7,7-diphenyl-4-perhydroisoindolone (1.4 g) in the form of a yellow oil.

(3aRS,7aRS)-2-[(N-tert-butoxycarbonyl-2-N-propylamino-phenyl)acetyl]-7,7-diphenyl-4-perhydroisoindolone (1.4 g) is treated with a 5.7N solution (15 cc) of hydrochloric acid in dry dioxane at 20° C. for 4 hours. The reaction mixture is concentrated to dryness under reduced pressure (2.7 kPa) and the residue is dissolved in a mixture of ethyl acetate (50 cc) and water (50 cc). The crystals formed are drained, washed with water (15 cc), ethyl acetate (25 cc) and isopropyl ether (2×50 cc) and dried. (3aRS,7aRS)-7,7-diphenyl-2-[(2-propylaminophenyl)acetyl]-4-perhydroisoindolone (0.75 g) is obtained in the form of white crystals melting at 238° C.

(N-tert-Butoxycarbonyl-2-N-propylaminophenyl)acetic acid can be prepared in the following way:

A solution of propyl (N-tert-butoxycarbonyl-2-N-propylamino-phenyl)acetate (1.1 g) in ethanol (25 cc) is treated with normal sodium hydroxide solution (3.3 cc) for 3 hours under reflux. The reaction mixture is concentrated under reduced pressure (2.7 kPa). The residue is taken up in water (50 cc) and ethyl acetate (50 cc) and acidified to pH 1 with 4N hydrochloric acid and the aqueous phase is extracted with ethyl acetate (2×50 cc). The combined organic phases are washed with water (50 cc) and saturated sodium chloride solution (50 cc), dried over magnesium sulphate and filtered and the filtrate is concentrated to dryness under reduced pressure (2.7 kPa) to give (N-tert-butoxycarbonyl-2-N-propylamino-phenyl)acetic acid (0.9 g) in the form of a yellow oil.

Propyl (N-tert-butoxycarbonyl-2-N-propylaminophenyl)acetate can be prepared in the following way:

A solution of (2-tert-butoxycarbonylaminophenyl)acetic acid (3 g) in dry dimethylformamide (30 cc) is added to a suspension of sodium hydride (0.72 g) (80% dispersion in oil) in dry dimethylformamide (20 cc). The reaction mixture is heated at 80° C. for 2 hours and cooled to 20° C. Propyl iodide (2.33 cc) is added and the mixture is stirred at 20° C. for 20 hours. The mixture is diluted with water (100 cc) and extracted with ethyl acetate (2×100 cc). The combined organic phases are washed with water (2×100 cc) and with saturated sodium chloride solution (100 cc), dried over magnesium sulphate and filtered and the filtrate is concentrated to dryness under reduced pressure (2.7 kPa). The residue is chromatographed on a silica gel column (0.2–0.063 mm, diameter 2.6 cm, height 27 cm), eluting under a nitrogen pressure of 0.5 bar with a mixture of cyclohexane and ethyl acetate (97/3 by volume) and collecting 35 cc fractions. Fractions 10 to 20 are combined and concentrated to dryness under reduced pressure (2.7 kPa) to give propyl (N-tert-butoxycarbonyl-2-N-propylaminophenyl)acetate (1.1 g) in the form of a yellow oil.

EXAMPLE 59

N,N'-Carbonyldiimidazole (1 g) is added to a solution of 2-dimethylaminophenylacetic acid (1.1 g) in dry dichloromethane (30 cc), cooled to +5° C. The mixture is stirred at +5° C. for 30 minutes and a solution of (3aRS,7aRS)-7,7-diphenyl-4-perhydroisoindolone hydrochloride (2.03 g) and triethylamine (1.68 cc) in dichloromethane (20 cc) is then added. The reaction mixture is stirred at 20° C. for 24 hours, then washed with water (3×200 cc), dried over magnesium sulphate and filtered and the filtrate is concentrated to dryness under reduced pressure (2.7 kPa). The residue is chromatographed on a silica gel column (0.2–0.063 mm, diameter 3 cm, height 25 cm), eluting under a nitrogen pressure of 0.7 bar with a mixture of cyclohexane and ethyl acetate (40/60 by volume) and collecting 125 cc fractions. Fractions 8 to 26 are combined and concentrated to dryness under reduced pressure (2.7 kPa). The residue is crystallized from isopropyl ether (40 cc). The crystals are drained, washed with isopropyl ether and dried. (3aRS,7aRS)-7,7-diphenyl-2-[2-(2-dimethylaminophenyl)acetyl]-4-perhydroisoindolone (0.9 g) is obtained in the form of white crystals melting at 150° C.

2-Dimethylaminophenylacetic acid is prepared by the method of D-U. Lee, K. K. Mayer and W. Wiegrebe (Arch. Pharm. (Weinheim), 321, 303 (1988)).

EXAMPLE 60

N,N'-Carbonyldiimidazole (2.43 g) is added to a solution of 2-dimethylaminophenylacetic acid (2.68 g) in dry dichloromethane (50 cc), cooled to +5° C. The mixture is stirred at +5° C. for 90 minutes and a solution of (3aR,7aR)-7,7-diphenyl-4-perhydroisoindolone hydrochloride (4.9 g) and triethylamine (4.2 cc) in dichloromethane (50 cc) is then added. The reaction mixture is stirred at 20° C. for 16 hours, then washed with water (2×100 cc), dried over magnesium sulphate and filtered and the filtrate is concentrated to dryness under reduced pressure (2.7 kPa). The residue is chromatographed on a silica gel column (0.2–0.063 mm, diameter 5 cm, height 50 cm), eluting under a nitrogen pressure of 0.7 bar with a mixture of cyclohexane and ethyl acetate (40/60 by volume) and collecting 125 cc fractions. Fractions 5 to 20 are combined and concentrated to dryness under reduced pressure (2.7 kPa). The residue is crystallized from a mixture of acetonitrile (40 cc) and isopropyl ether (200 cc). The crystals are drained, washed with isopropyl ether and dried. (3aR,7aR)-7,7-diphenyl-2-[2-(2-dimethylaminophenyl)acetyl]-4-perhydroisoindolone (2.58 g) is obtained in the form of white crystals, melting at 190° C.; $[\alpha]_D^{20} = -242°$ (c=1.18, chloroform)

EXAMPLE 61

N,N'-Carbonyldiimidazole (0.86 g) is added to a solution of 2-diethylaminophenylacetic acid (1.1 g) in dry dichloromethane (30 cc), cooled to +5° C. The mixture is stirred at +5° C. for 30 minutes and a solution of (3aRS,7aRS)-7,7-diphenyl-4-perhydroisoindolone hydrochloride (1.73 g) and triethylamine (1.48 cc) in dichloromethane (40 cc) is then added. The reaction mixture is stirred at 20° C. for 24 hours, then washed with water (2×150 cc), dried over magnesium sulphate and filtered and the filtrate is concentrated to dryness under reduced pressure (2.7 kPa). The residue is chromatographed on a silica gel column (0.2–0.063 mm, diameter 3 cm, height 40 cm), eluting under a nitrogen pressure of 0.7 bar with a mixture of cyclohexane and ethyl acetate (30/80 by volume) and collecting 125 cc fractions. Fractions 12 to 20 are combined and concentrated to dryness under reduced pressure (2.7 kPa). The residue is crystallized from a mixture of acetonitrile (15 cc) and isopropyl ether (50 cc). The crystals are drained, washed with isopropyl ether and dried. (3aRS,7aRS)-7,7-diphenyl-2-[2-(2-diethylaminophenyl)acetyl]-4-perhydroisoindolone (1.6 g) is obtained in the form of white crystals melting at 160° C.

2-Diethylaminonphenylacetic acid is prepared by hydrogenation of a suspension of 2-nitrophenylacetic acid (9 g) in ethanol (40 cc) under a pressure of 7 bar for 4 hours at 25° C. in the presence of acetaldehyde (7 cc) and 10% palladium-on-carbon black (1 g). The reaction mixture is filtered, the filtrate is concentrated to dryness under reduced pressssure (2.7 kPa) and the residue is chromatographed on a silica column (0.2–0.063 mm, diameter 5 cm, height 50 cm), eluting under a nitrogen pressure of 0.7 bar with a mixture of cyclohexane and ethyl acetate (70/30 by volume) and collecting 125 cc fractions. Fractions 38 to 48 are concentrated to dryness under reduced pressure (2.7 kPa) to give 2-diethylaminophenylacetic acid (1.1 g) in the form of a yellow oil.

EXAMPLE 62

N,N'-Carbonyldiimidazole (1.62 g) is added to a solution of (2-dimethylamino-6-fluorophenyl)acetic acid (1.97 g) in dry dichloromethane (50 cc), cooled to +5° C. The mixture is stirred for 90 minutes at +5° C. and a solution of (3aRS,7aRS)-7,7-diphenyl-4-perhydroisoindolone hydrochloride (3.27 g) and triethylamine (2.8 cc) in dichloromethane (50 cc) is then added. The reaction mixture is stirred at 20° C. for 16 hours, then washed with water (2×100 cc), dried over magnesium sulphate and filtered and the filtrate is concentrated to dryness under reduced pressure (2.7 kPa). The residue is chromatographed on a silica gel column (particle size 0.04–0.06 mm, diameter 4 cm, height 25 cm), eluting under a nitrogen pressure of 0.5 bar with a mixture of cyclohexane and ethyl acetate (70/30 by volume) and collecting 50 cc fractions. Fractions 6 to 19 are combined and concentrated to dryness under reduced pressure. The residue is triturated in ethyl ether. The crystals are drained and dried. (3aRS,7aRS)-2-[(2-dimethylamino-6-fluorophenyl)acetyl]-7,7-diphenyl-4-perhydroisoindolone (3.6 g) is obtained in the form of white crystals melting at 210° C.

(2-Dimethylamino-6-fluorophenyl)acetic acid is prepared in the following way:

10% palladium-on-charcoal (1.0 g) is added to a solution of (6-fluoro-2-nitrophenyl)acetic acid (10 g) and 37% aqueous formaldehyde solution (25 cc) in ethanol (45 cc), in a 250 cm³ autoclave, and the autoclave is then placed under a hydrogen pressure of 30 bar and the mixture is stirred at ambient temperature for 45 minutes. The reaction mixture is then filtered and the filtrate is concentrated to dryness under reduced pressure (2.7 kPa). The residue is chromatographed on a Merck silica gel column (particle size 0.06–0.04 mm, diameter 4.0 cm, height 40 cm), eluting with a mixture of cyclohexane and ethyl acetate (75/25 by volume) and collecting 60 cc fractions. Fractions 11 to 25 are combined and concentrated to dryness under reduced pressure (2.7 kPa). (2-Dimethylamino-6-fluorophenyl)acetic acid (7.0 g) is obtained in the form of white crystals melting at 94° C.

(6-Fluoro-2-nitrophenyl)acetic acid is obtained by the method described in CS Patent 194005.

EXAMPLE 63

N,N'-Carbonyldiimidazole (1.64 g) is added to a solution of (2-dimethylamino-4-fluorophenyl)acetic acid (2 g) in dry dichloromethane (50 cc), cooled to +5° C. The mixture is stirred for 90 minutes at +5° C. and a solution of (3aRS,7aRS)-7,7-diphenyl-4-perhydroisoindolone hydrochloride (3.3 g) and triethylamine (2.8 g) in dichloromethane (50 cc) is then added. The reaction mixture is stirred at 20° C. for 16 hours, then washed with water (2×100 cc), dried over magnesium sulphate and filtered and the filtrate is concentrated to dryness under reduced pressure (2.7 kPa). The residue is chromatographed on a silica gel column (particle size 0.04–0.06 mm, diameter 4 cm, height 25 cm), eluting under a nitrogen pressure of 0.4 bar with a mixture of cyclohexane and ethyl acetate (50/50 by volume) and collecting 50 cc fractions. Fractions 5 to 12 are combined and concentrated to dryness under reduced pressure. The residue is triturated in ethyl ether. The crystals are drained and dried. (3aRS,7aRS)-2-[(2-dimethylamino-4-fluorophenyl)acetyl]-7,7-diphenyl-4-perhydroisoindolone (3.1 g) is obtained in the form of white crystals melting at 164° C.

(2-Dimethylamino-4-fluorophenyl)acetic acid is prepared in the following way: 10% palladium-on-charcoal (0.6 g) is added to a solution of (4-fluoro-2-nitrophenyl)acetic acid (5.5 g) and 37% aqueous formaldehyde solution (15 cc) in ethanol (130 cc), in a 250 cm³ autoclave, and the autoclave is then placed under a hydrogen pressure of 47 bar and the mixture is stirred at ambient temperature for 48 hours. The reaction mixture is then filtered and the filtrate is concentrated to dryness under reduced pressure (2.7 kPa). The residue is chromatographed on a Merck silica gel column (particle size 0.06–0.04 mm, diameter 4.2 cm, height 50 cm), eluting with a mixture of cyclohexane and ethyl acetate (80/20 by volume) and collecting 50 cc fractions. Fractions 9 to 23 are combined and concentrated to dryness under reduced pressure (2.7 kPa). (2-Dimethylamino-4-fluorophenyl)acetic acid (3.9 g) is obtained in the form of a colorless oil.

(4-Fluoro-2-nitrophenyl)acetic acid is obtained by the method described in CS Patent 194005.

EXAMPLE 64

N,N'-Carbonyldiimidazole (1.13 g) is added to a solution of 2-[2-(1-pyrrolydinyl)phenyl]acetic acid (1.42 g) in dry dichloromethane (30 cc), cooled to +5° C. The mixture is stirred for 40 minutes at +5° C. and a solution of (3aRS,7aRS)-7,7-diphenyl-4-perhydroisoindolone hydrochloride (2.3 g) and triethylamine (0.98 cc) in dichloromethane (20 cc) is then added. The reaction mixture is stirred for 1 hour at +5° C. and then for 1 hour at 20° C. It is washed with distilled water (2×20 cc), dried over magnesium sulphate and filtered and the filtrate is concentrated to dryness under reduced pressure (2.7 kPa). The residue is chromatographed on a silica gel column (0.2–0.063 mm, diameter 2 cm, height 25 cm), eluting with a mixture of ethyl acetate and cyclohexane (70/30 by volume) and collecting 100 cc fractions. Fractions 3 to 8 are combined and concentrated to dryness under reduced pressure (2.7 kPa). The residue is recrystallized from a mixture of acetonitrile (5 cc) and isopropyl ether (5 cc). The crystals are drained, washed with ethylene oxide (10 cc) and dried. (3aRS,7aRS)-7,7-diphenyl-2-[2-[2-(1-pyrrolidinyl)phenyl]acetyl]-4-perhydroisoindolone (2.2 g) melting at 178° C. is obtained.

A mixture of 2-(2-bromophenyl)acetic acid (10.7 g), pyrrolidine (20 cc) and copper acetate (1.66 g) is heated for 2 hours, with stirring, at 90° C.; after returning to ambient temperature, the reaction mixture is concentrated to dryness under reduced pressure (2.7 kPa). The residue is chromatographed on a silica gel column (0.2–0.063 mm, diameter 5 cm, height 55 cm), eluting with 1,2-dichloroethane (1,000 cc) and then with mixtures of 1,2-dichloroethane and methanol [(proportions by volume): 1,000 cc (98/2), 2,000 cc (97/3), 1,000 cc (96/4) and 1,000 cc (95/5)] and collecting 250 cc fractions. Fractions 21 to 29 are combined and concentrated to dryness under reduced pressure (2.7 kPa). 2-[2-(1-Pyrrolidinyl)phenyl]acetic acid (2 g) is obtained in the form of an orange oil.

EXAMPLE 65

N,N'-Carbonyldiimidazole (0.35 g) is added to a solution of 2-[2-(4-morpholinyl)phenyl]acetic acid (0.48 g) in dry dichloromethane (25 cc), cooled to +5° C. The mixture is stirred for 75 minutes at +5° C. and a solution of (3aRS,7aRS)-7,7-diphenyl-4-perhydroisoindolone hydrochloride (0.71 g) and triethylamine (0.6 cc) in dichloromethane (20 cc) is then added. The reaction mixture is stirred for 1 hour at +5° C. and then for 8 hours at 20° C. It is washed with distilled water (3×100 cc) and with saturated sodium chloride solution (100 cc), dried over magnesium sulphate and filtered and the filtrate is concentrated to dryness under reduced pressure (2.7 kPa). The residue is chromatographed on a silica gel column (0.04–0.063 mm, diameter 2.2 cm, height 12 cm), eluting with a mixture of ethyl acetate and cyclohexane (70/30 by volume) under a nitrogen pressure of 0.7 bar and collecting 50 cc fractions. Fractions 4 and 5 are combined and concentrated to dryness under reduced pressure (2.7 kPa). The residue is recrystallized from ethylene oxide (2 cc). The crystals are drained, washed with isopropyl ether (1 cc) and dried. (3aRS,7aRS)-7,7-diphenyl-2-[2-[2-(4-morpholinyl)-phenyl]acetyl]-4-perhydroisoindolone (0.27 g) melting at 167° C. is obtained.

2-[2-(4-Morpholinyl)phenyl]acetic acid can be prepared in the following way:

A solution of N-[[2-(4-morpholinyl)-phenyl]thioacetyl]morpholine (2.78 g) in a mixture of acetic acid (25 cc) and 37% hydrochloric acid (25 cc) is refluxed for 8 hours and then concentrated to dryness under reduced pressure (2.7 kPa). The residue is taken up in ethyl acetate (20 cc) and normal sodium hydroxide solution (20 cc). The aqueous phase is acidified to pH 5 with acetic acid and then extracted with ethyl acetate (20 cc). This organic phase is washed with water (2×4 cc), dried over magnesium sulphate and concentrated to dryness under reduced pressure (2.7 kPa). 2-[2-(4-Morpholinyl)phenyl]acetic acid (0.48 g) melting at 128° C. is obtained.

N-[[2-(4-Morpholinyl)phenyl]thioacetyl]morpholine can be prepared in the following way:

A mixture of 2-(4-morpholinyl)acetophenone (4.6 g), morpholine (3.9 cc) and sulphur (1.79 g) is refluxed, with stirring, for 5 hours and the hot reaction mixture is then diluted with boiling ethanol (17 cc). After cooling, the solid is drained and chromatographed on a silica gel column (0.04–0.063 mm, diameter 3.9 cm, height 30 cm), eluting under a nitrogen pressure of 0.6 bar with a mixture of cyclohexane and ethyl acetate (60/40 by volume) and collecting 100 cc fractions. Fractions 7 to 28 are combined and concentrated to dryness under reduced pressure (2.7 kPa) to give N-[[2-(4-morpholinyl)-phenyl]thioacetyl]morpholine (3.82 g) melting at 140° C.

2-(4-Morpholino)acetophenone can be prepared in the following way:

A mixture of 2-fluoroacetophenone (19.9 g), morpholine (21 cc) and potassium carbonate (27.6 g) in dimethyl sulphoxide (32 cc) is heated at 110° C. for 30 hours. The reaction mixture is diluted with water (100 cc) and extracted with ethyl acetate (4×100 cc); the organic solution is washed with distilled water (100 cc), dried over magnesium sulphate and concentrated to dryness under reduced pressure (2.7 kPa). The residue is chromatographed on a silica gel column (0.04–0.063 mm, diameter 9 cm, height 40 cm), eluting with a mixture of cyclohexane and ethyl acetate (80/20 by volume) and collecting 250 cc fractions. Fraction 24 to 44 are combined and concentrated to dryness under reduced pressure (2.7 kPa). 2-(4-Morpholinyl)acetophenone (4.72 g) is obtained which is used as such for the subsequent syntheses.

EXAMPLE 66

N,N'-Carbonyldiimidazole (1.13 g) is added to a solution of 2-(1-naphthyl)acetic acid (1.3 g) in dry dichloromethane (30 cc), cooled to +5° C. The mixture is stirred for 25 minutes at +5° C. and a solution of (3aRS,7aRS)-7,7-diphenyl-4-perhydroisoindolone hydrochloride (2.3 g) and triethylamine (0.98 cc) in dichloromethane (40 cc) is then added. The reaction mixture is stirred at 20° C. for 4 hours, then washed with distilled water (2×50 cc), dried over magnesium sulphate and filtered and the filtrate is concentrated to dryness under reduced pressure (2.7 kPa). The residue is chromatographed on a silica gel column (0.2–0.063 mm), diameter 1.8 cm, height 19 cm), eluting with dichloromethane and collecting 30 cc fractions. Fractions 3 to 8 are combined and concentrated to dryness under reduced pressure (2.7 kPa). The residue is crystallized from acetonitrile (14 cc). The crystals are drained, washed with isopropyl ether (10 cc) and dried. (3aRS,7aRS)-2-(1-naphthylacetyl)-7,7-diphenyl-4-4-perhydroisoindolone (1.4 g) melting at 207° C. is obtained.

EXAMPLE 67

N,N'-Carbonyldiimidazole (0.81 g) is added to a solution of 2-(2-thienyl)acetic acid (0.71 g) in dry dichloromethane (20 cc), cooled to +5° C. The mixture is stirred for 1 hour at +5° C. and a solution of 7,7-diphenyl-4-perhydroisoindolone hydrochloride (1.6 g) and triethylamine (0.7 cc) in dichloromethane (20 cc) is then added. The reaction mixture is stirred for 2 hours at +5° C. and for 16 hours at 20° C. and is then washed with distilled water (3×50 cc), dried over magnesium sulphate and filtered and the filtrate is concentrated to dryness under reduced pressure (2.7 kPa). The residue is recrystallized from acetonitrile (10 cc). The crystals are drained, washed with isopropyl ether (10 cc) and dried. (3aRS,7aRS)-7,7-diphenyl-2-[(2-thienyl)acetyl]-4-perhydroisoindolone (1.5 g) melting at 206° C. is obtained.

EXAMPLE 68

N,N'-Carbonyldiimidazole (1.13 g) is added to a solution of 2-(3-thienyl)acetic acid (0.99 g) in dry dichloromethane (30 cc), cooled to +5° C. The mixture is stirred for 15 minutes at +5° C. and a solution of (3aRS,7aRS)-7,7-diphenyl-4-perhydroisoindolone hydrochloride (2.24 g) and triethylamine (1.96 cc) in dichloromethane (20 cc) is then added. The reaction mixture is stirred for 16 hours at 20° C., then washed with distilled water (3×50 cc), dried over magnesium sulphate and filtered and the filtrate is concentrated to dryness under reduced pressure (2.7 kPa). The residue is recrystallized from a mixture of acetonitrile (30 cc) and isopropyl ether (40 cc). The crystals are drained, washed with isopropyl ether and dried. (3aRS,7aRS)-7,7-diphenyl-2-[2-(3-thienyl)acetyl]-4-perhydroisoindolone (2.2 g) melting at 224° C. is obtained.

EXAMPLE 69

N,N'-Carbonyldiimidazole (1.13 g) is added to a solution of 2-(1,3-dithiin-5-yl)acetic acid (1.23 g) in dry dichloromethane (30 cc), cooled to +5° C. The mixture is stirred for 20 minutes at +5° C. and a solution of (3aRS,7aRS)-7,7-diphenyl-4-perhydroisoindolone hydrochloride (2.3 g) and triethylamine (0.98 cc) in dichloromethane (40 cc) is then added. The reaction mixture is stirred for 16 hours at 20° C. The reaction mixture is washed with distilled water (3×50 cc), dried over magnesium sulphate and filtered and the filtrate is concentrated to dryness under reduced pressure (2.7 kPa). The residue is crystallized from acetonitrile (80 cc). The crystals are drained, washed with isopropyl ether (10 cc) and dried. (3aRS,7aRS)-7,7-diphenyl-2-[2-(1,3-dithiin-5-yl)acetyl]-4-perhydroisoindolone (1.94 g) melting at 211° C. is obtained.

EXAMPLE 70

Triethylamine (1.4 cc) is added to a suspension of 2-(2-pyridyl)acetic acid hydrochloride (1.73 g) in dry dichloromethane (30 cc). The solution is cooled to +5° C. and then treated with N,N'-carbonyldiimidazole (1.62 g). The mixture is stirred for 15 minutes at +5° C. and a solution of (3aRS,7aRS)-7,7-diphenyl-4-perhydroisoindolone hydrochloride (3.27 g) and triethylamine (2.8 cc) in dichloromethane (20 cc) is then added. The reaction mixture is stirred at 20° C. for 2 hours and then concentrated to dryness under reduced pressure (2.7 kPa). The residue is taken up in a mixture of ethyl acetate (100 cc) and water (75 cc). The organic phase is washed with water (50 cc), dried over magnesium sulphate and filtered and the filtrate is concentrated to dryness under reduced pressure (2.7 kPa). The residue is recrystallized from a mixture of acetonitrile (30 cc) and isopropyl ether (30 cc). (3aRS,7aRS)-7,7-diphenyl-2-[2-(2-pyridyl)acetyl]-4-perhydroisoindolone (1.6 g) is obtained in the form of white crystals melting at 195° C.

EXAMPLE 71

N,N'-Carbonyldiimidazole (0.81 g) is added to a solution of 2-(3-pyridyl)acetic acid (0.685 g) in dry dichloromethane (15 cc), cooled to +5° C. The mixture is stirred for 30 minutes at +5° C. and a solution of (3aRS,7aRS)-7,7-diphenyl-4-perhydroisoindolone hydrochloride (1.6 g) and triethylamine (0.7 cc) in dichloromethane (10 cc) is then added. The reaction mixture is stirred at 20° C. for 16 hours and then concentrated to dryness under reduced pressure (2.7 kPa). The residue is taken up in a mixture of ethyl acetate (100 cc) and water (75 cc). The organic phase is washed with saturated sodium chloride solution (50 cc), dried over magnesium sulphate and filtered and the filtrate is concentrated to dryness under reduced pressure (2.7 kPa). The residue is chromatographed on a basic alumina column (diameter 2 cm, height 15 cm), eluting with ethyl acetate and collecting 50 cc fractions. Fractions 4 to 24 are concentrated to dryness under reduced pressure (2.7 kPa). The crystals obtained are recrystallized from acetonitrile (cc) to give (3aRS,7aRS)-7,7-diphenyl-2-[2-(3-pyridyl)acetyl]-4-perhydroisoindolone (0.9 g) in the form of white crystals melting at 208° C.

EXAMPLE 72

N,N'-Carbonyldiimidazole (4.05 g) is added to a solution of 2-(3-indolyl)acetic acid (4.37 g) in dry dichloromethane (100 cc), cooled to +5° C. The mixture is stirred for 1 hour at +5° C. and (3aRS,7aRS)-7,7-diphenyl-4-perhydroisoindolone (7.3 g) is then added. The reaction mixture is stirred at 20° C. for 20 hours, then washed with distilled water (3×50 cc), dried over magnesium sulphate and filtered and the filtrate is concentrated to dryness under reduced pressure (2.7 kPa). The residue is chromatographed on a silica gel column (0.2–0.063 mm, diameter 7 cm, height 40 cm), eluting with a mixture of ethyl acetate and cyclohexane (70/30 by volume) and collecting 100 cc fractions. Fractions 6 to 11 are concentrated to dryness under reduced pressure (2.7 kPa). The residue is recrystallized from acetonitrile (50 cc). The crystals obtained are drained, washed with isopropyl ether (10 cc) and dried. (3aRS,7aRS)-7,7-diphenyl-2-[2-(3-indolyl)acetyl]-4-perhydroisoindolone (5 g) melting at 250° C. is obtained.

4N aqueous sodium hydroxide solution (100 cc) is added to a solution of (3aRS,7aRS)-7,7-diphenyl-4-perhydroisoindolone hydrochloride (16.6 g) in dichloromethane (250 cc), with stirring; the organic phase is dried over magnesium sulphate and filtered and the filtrate is concentrated to dryness under reduced pressure (4 kPa). (3aRS,7aRS)-7,7-diphenyl-4-perhydroisoindolone (13 g) is obtained in the form of a white meringue.

Proton NMR spectrum: 2.15 and 2.4 (2 Mt, respectively 1H each, —CH$_2$— in 5 or 6); 2.75 (Mt, 4H, —CH$_2$— in 1 and —CH$_2$— in 6 or 5); 3.3 to 3.6 (Mt, 2H, 1H of the —CH$_2$— in 3 and —CH— in 3a); 3.95 to 4.2

(Mt, 2H, 1H of the —CH$_2$— in 3 and —CH— in 7a); 7 to 7.5 (Mt, 10H, aromatic).

Infrared spectrum (CHBr$_3$), characteristic bands (cm$^{-1}$): 3350, 3100-3000, 3000-2800, 1705, 1600, 1580, 1495, 1460, 1445, 755.

EXAMPLE 73

A solution of (3aR,7aR)-7,7-diphenyl-4-perhydroisoindolone hydrochloride (2.12 g), triethylamine (0.9 cc) and pyridine (0.5 cc) in dichloromethane (30 cc) is added, at 0° C., to a solution of (S)-α-fluorophenylacetyl chloride [prepared from acid (1 g) by the method described by S. Hamman et al., J. Fluorine Chem., 37, 85 (1987)] in dichloromethane (20 cc). The reaction mixture is stirred for 2 hours allowing the temperature to return to 20° C. and is then concentrated to dryness under reduced pressure (2.7 kPa). The residue is taken up in ethyl acetate (100 cc). The solution is washed with water (2×100 cc) and then with saturated sodium bicarbonate solution (50 cc) and with saturated sodium chloride solution (50 cc), dried over magnesium sulphate and filtered and the filtrate is concentrated to dryness under reduced pressure (2.7 kPa). The residue is chromatographed on a silica gel column (particle size 0.2-0.063 mm, diameter 3 cm, height 40 cm), eluting under a nitrogen pressure of 0.7 bar with ethyl acetate and collecting 100 cc fractions to give (3aR,7aR)-2-[(S)-α-fluorophenylacetyl]-7,7-diphenyl-4-perhydroisoindolone (1 g) in the form of a white meringue.

Proton NMR spectrum (DMSO-d$_6$): At ordinary temperature the mixture of the two rotamers is observed. 2 to 2.4 (m, 2H, —CH$_2$— in 5); 2.45 to 3 (m, 4H, —CH$_2$— in 6 and —CH$_2$— in 1); 3.11 to 3.28 (2m, 1H, 1H in 3); 3.38 (m, 1H, 1H in 3a); 3.94 and 4.05 (2m, 1H, H in 7a); 4.2 and 4.38 (2m, J=11, 1H, 1H in 3); 5.90 and 6.28 (2d, J=47, 1H, —CHF—); 7 to 7.7 (m, 15H, aromatic).

Infrared spectrum (characteristic bands in cm$^{-1}$): 3100-3000, 3000-2875, 1715, 1655, 1600, 1580, 1495, 1450, 750, 700.

EXAMPLE 74

N,N'-Carbonyldiimidazole (0.66 g) is added to a solution of (S)-2-phenylpropionic acid (0.62 g) in dry dichloromethane (30 cc), cooled to +5° C. The mixture is stirred for 40 minutes at +5° C. and a solution of (3aR,7aR)-7,7-diphenyl-4-perhydroisoindolone hydrochloride (1.35 g) and triethylamine (0.57 cc) in dichloromethane (40 cc) is then added. The reaction mixture is stirred at 20° C. for 16 hours, then washed with distilled water (2×50 cc), dried over magnesium sulphate and filtered and the filtrate is concentrated to dryness under reduced pressure (2.7 kPa). The residue is chromatographed on a silica gel column (0.2-0.063 mm, diameter 1.8 cm, height 15 cm), eluting with ethyl acetate and collecting 15 cc fractions. The first fraction is concentrated to dryness under reduced pressure (2.7 kPa). (3aR,7aR)-7,7-diphenyl-2-[(S)-2-phenylpropionyl]-4-perhydroisoindolone (1 g) is obtained in the form of a white meringue. $[\alpha]_D^{20} = -231°$ (c=1, methanol).

Proton NMR spectrum: At ambient temperature, the mixture of the two rotamers is observed. 1.16 and 1.26 (2D, 3H in total, —CH$_3$); 1.95 to 2.3 (Mt, 2H, —CH$_2$— in 5 or 6); 2.65 to 2.9 (Mt, 4H, —CH$_2$— in 6 or 5 and —CH$_2$— in 1); 3.05 to 3.35 (Mt, 2H, 1H of the —CH$_2$— in 3 and —CH— in 3a); 3.4 and 3.8 to 4 (Mt, —N—CO—CH— and —CH— in 7a); 4.2 to 4.4 (Mt, 1H, 1H of the —CH$_2$— in 3); 6.9 to 7.6 (Mt, 15H, aromatic).

Infrared spectrum (KBr), characteristic bands (cm$^{-1}$): 3600-3300, 3100-3000, 3000-2870, 1715, 1640, 1600, 1580, 1495, 1455, 1445, 1420, 1370, 755, 700.

EXAMPLE 75

N,N'-Carbonyldiimidazole (0.66 g) is added to a solution of (R)-2-phenylpropionic acid (0.62 g) in dry dichloromethane (30 cc), cooled to +5° C. The mixture is stirred for 30 minutes at +5° C. and a solution of (3aR,7aR)-7,7-diphenyl-4-perhydroisoindolone hydrochloride (1.35 g) and triethylamine (0.57 cc) in dichloromethane (40 cc) is then added. The reaction mixture is stirred at 20° C. for 16 hours and then concentrated to dryness under reduced pressure (2.7 kPa). The residue is dissolved in ethyl acetate (100 cc) and the solution is washed with water (2×50 cc), dried over magnesium sulphate and filtered and the filtrate is concentrated to dryness under reduced pressure (4 kPa). The residue is chromatographed on a silica gel column (0.2-0.04 mm, diameter 2.8 cm, height 15 cm), eluting under a nitrogen pressure of 0.5 bar with a mixture of cyclohexane and ethyl acetate (60/40 by volume) and collecting 50 cc fractions. Fractions 4 to 8 are concentrated to dryness under reduced pressure (4 kPa) to give (3aR,7aR)-7,7-diphenyl-2-[(R)-2-phenylpropionyl]-4-perhydroisoindolone (1.4 g) in the form of a white meringue, the infrared spectrum of which is identical to that of the product from Example 68; $[\alpha]_D^{20} = -278°$ (c=1, methanol).

Proton NMR spectrum: 1.2 and 1.28 (2D, 3H in total, —CH$_3$); 1.9 to 2.3 (Mt, 2H, —CH$_2$— in 5 or 6); 2.50 to 3.15 (Mt, 4H, —CH$_2$— in 6 or 5 and —CH$_2$— in 1); 3.15 to 4.05 (Mt, —CH— in 3a, 1H of the —CH$_2$— in 3, —N—CO—CH—, —CH— in 7a); 4 to 4.21 (Mt, 1H of the —CH$_2$— in 3); 6.85 to 7.7 (Mt, 15H, aromatic).

EXAMPLE 76

1-Hydroxybenzotriazole (0.59 g) is added to a solution of (S)-2-[2-methoxyphenyl]propionic acid (0.75 g) of 84% optical purity prepared by the method of T. Matsumoto et al: Bull. Chem. Soc. Jpn., 58, 340 (1985), in dry dimethylformamide (15 cc) and the solution is then cooled to 0° C. N,N'-Dicyclohexylcarbodiimide (0.91 g) is added, the mixture is stirred for 1 hour at this temperature and a solution of (3aR,7aR)-7,7-diphenyl-4-perhydroisoindolone hydrochloride (1.44 g) and N,N-diisopropylethylamine (0.76 cc) in dimethylformamide (10 cc) is then added. The reaction mixture is stirred at 20° C. for 16 hours, diluted with ethyl acetate (100 cc) and concentrated to dryness under reduced pressure (2.7 kPa) after filtering off the precipitate. The residue is chromatographed on a silica gel column (0.2-0.063 mm, diameter 3 cm, height 40 cm), eluting under a nitrogen pressure of 0.7 bar with a mixture of cyclohexane and ethyl acetate (50/50 by volume) and collecting 125 cc fractions. Fractions 4 to 7 are combined and concentrated to dryness under reduced pressure (2.7 kPa). The residue is purified by dissolving in boiling isopropyl ether (60 cc) to which hexane (30 cc) had been added. The cooled solution is filtered and the filtrate is concentrated to dryness under reduced pressure (2.7 kPa) to give (3aR,7aR)-7,7-diphenyl-2-[(S)-2-(2-methoxyphenyl)propionyl]-4-perhydroisoindolone (1.2 g) in the form of a white meringue containing 10% of (3aR,7aR)-7,7-diphenyl-2-[(R)-2-(2-methoxyphenyl)propionyl]-4-perhydroisoindolone; $[\alpha]_D^{20} = -181°$ (c=0.81, chloroform).

Proton NMR spectrum: At ambient temperature the mixture of the two rotamers of each of the two diastereoisomers is observed, the two diastereoisomers being in the proportions 90/10. 1.10 and 1.20 (2 Mt, 3H in total, —CH$_3$); 1.9 to 2.4 (Mt, 2H, —CH$_2$— in 5 or 6); 2.55 to 2.95 (Mt, —CH$_2$— in 1 and —CH$_2$— in 6 or 5); 2.95 to 3.4 (Mt, 1H of the —CH$_2$— in 3 and —CH— in 3a); 3.20–3.32–3.50 and 3.83 (4S, —OCH$_3$); 3.65 to 4.3 (Mt, —CH— in 7a, —N—CO—CH—, 1H of the —CH$_2$— in 3); 6.7 to 7.65 (Mt, 14H, aromatic).

Infrared spectrum (KBr), characteristic bands (cm$^{-1}$): 3430, 3100–3000, 3000–2800, 1715, 1640, 1595, 1585, 1490, 1460, 1445, 1420, 1365, 1240, 1030, 755, 703.

EXAMPLE 77

N,N'-Carbonyldiimidazole (0.85 g) is added to a solution of (RS)-2-[2-dimethylaminophenyl]propionic acid (1 g) in dichloromethane (30 cc) cooled to 5° C. and the mixture is then stirred for 30 minutes at this temperature. A solution of (3aR,7aR)-7,7-diphenyl-4-perhydroisoindolone hydrochloride (1.7 g) and triethylamine (1.4 cc) in dichloromethane (30 cc) is added. The reaction mixture is stirred at 20° C. for 16 hours, washed with water (2×100 cc), dried over magnesium sulphate and concentrated to dryness under reduced pressure (2.7 kPa). The residue is chromatographed on a silica gel column (0.2–0.063 mm, diameter 3 cm, height 50 cm), eluting under a nitrogen pressure of 0.5 bar with ethyl acetate and collecting 125 cc fractions. Fractions 4 to 6 are combined and concentrated to dryness under reduced pressure (2.7 kPa) to give (3aR,7aR)-2-[(RS)-2-(2-dimethylaminophenyl)propionyl]-7,7-diphenyl-4-perhydroisoindolone (1.4 g) in the form of a white meringue.

Proton NMR spectrum: At ordinary temperature, the mixture of the two rotamers of each of the two diastereoisomers is observed. 1.15 to 1.35 (Mt, 3H, —CH$_3$); 1.9 to 2.4 (Mt, —CH$_2$— in 5 or 6); 2.1–2.19–2.62–2.64 (4S, —N(CH$_3$)$_2$); 2.55 to 3.4 (Mt, —CH$_2$— in 6 or 5, —CH$_2$— in 1, —CH— in 3a and 1H of the —CH$_2$— in 3); 3.5 to 4.5 (Mt, —N—CO—CH—, 1H of the —CH$_2$— in 3 and —CH in 7a); 7 to 7.7 (Mt, 15H, aromatic).

Infrared spectrum (KBr), characteristic bands (cm$^{-1}$): 3600–3300, 3100–3000, 3000–2780, 1715, 1640, 1595, 1580, 1490, 1460, 1445, 1410, 750, 702.

A solution of 2-[2-dimethylaminophenyl]acetic acid (1.8 g) in dry tetrahydrofuran (10 cc) is added at 10° C. to a solution of lithium diisopropylamide (prepared by the action of a 1.6M solution (2.6 cc) of butyllithium in hexane on a solution of diisopropylamine (2.8 g) in dry tetrahydrofuran (30 cc) at 10° C.). The reaction mixture is stirred for 30 minutes at 20° C. and then for 30 minutes at 35° C. After cooling to 20° C., methyl iodide (0.63 cc) is added and the mixture is heated for 1 hour at 35° C. The mixture is cooled and diluted with water (20 cc) and ethyl acetate (100 cc). The aqueous phase is washed with ethyl acetate (100 cc), acidified to pH 5 with hydrochloric acid and extracted with ethyl acetate (2×100 cc). The organic phases are washed with water, dried over magnesium sulphate and concentrated to dryness under reduced pressure (2.7 kPa) to give (RS)-2-[2-dimethylaminophenyl]propionic acid in the form of a yellow oil.

EXAMPLE 78

N,N'-Carbonyldiimidazole (0.49 g) is added to a solution of (S)-2-phenylbutyric acid (0.5 g) in dry dichloromethane (15 cc), cooled to +5° C. The mixture is stirred for 30 minutes at +5° C. and a solution of (3aR,7aR)-7,7-diphenyl-4-perhydroisoindolone hydrochloride (0.98 g) and triethylamine (0.42 cc) in dichloromethane (20 cc) is then added. The reaction mixture is stirred at 20° C. for 16 hours, then washed with distilled water (2×50 cc), dried over magnesium sulphate and filtered and the filtrate is concentrated to dryness under reduced pressure (2.7 kPa). The residue is chromatographed on a silica gel column (0.2–0.063 mm, diameter 1.6 cm, height 9.7 cm), eluting with a mixture of ethyl acetate and cyclohexane (80/20 by volume) and collecting 30 cc fractions. The first fraction is concentrated to dryness under reduced pressure (2.7 kPa). The residue is re-chromatographed on a silica gel column (0.2–0.063 mm, diameter 1.3 cm, height 14.5 cm), eluting with a mixture of cyclohexane and ethyl acetate (70/30 by volume) and collecting 50 cc fractions. Fractions 1 to 3 are combined and concentrated to dryness under reduced pressure (2.7 kPa). (3aR,7aR)-7,7-diphenyl-2-[(S)-2-phenylbutyryl]-4-perhydroisoindolone (0.54 g) is obtained in the form of a white meringue. $[\alpha]_D^{20} = -216°$ (c=1, methanol).

Proton NMR spectrum: At ambient temperature, the mixture of the two rotamers is observed. 0.65 and 0.77 (2T, 3H in total, —CH$_3$ ethyl); 1.4 to 2 (Mt, —CH$_2$— of ethyl); 1.9 to 2.3 (Mt, 2H, —CH$_2$— in 5 or 6); 2.8 (Mt, 4H, —CH$_2$— in 6 or 5 and —CH$_2$— in 1); 3.05 to 3.35 and 3.48 (Mt, —CH— in 3a, —N—CO—CH— and 1H of the —CH$_2$— in 3); 3.75 to 4.1, (Mt, 1H, —CH— in 7a); 4.2 to 4.45 (Mt, 1H, 1H of the —CH$_2$— in 3); 6.9 to 7.65 (Mt, 15H, aromatic).

Infrared spectrum (KBr), characteristic bands (cm$^{-1}$): 3600–3300, 3100–3000, 3000–2830, 1715, 1640, 1600, 1580, 1492, 1450, 1445, 1420, 1375, 755 and 700.

EXAMPLE 79

N,N'-Carbonyldiimidazole (0.5 g) is added to a solution of (S)-3-tert-butoxycarbonylamino-2-phenylpropionic acid (0.79 g) in dry dichloromethane (20 cc), cooled to +5° C. The mixture is stirred for 1 hour 15 minutes at +5° C. and a solution of (3aR,7aR)-7,7-diphenyl-4-perhydroisoindolone hydrochloride (1 g) and triethylamine (0.4 cc) in dichloromethane (25 cc) is then added. The reaction mixture is stirred for 15 minutes at +5° C. and then for 16 hours at 20° C. The reaction mixture is washed with distilled water (3×100 cc), dried over magnesium sulphate and filtered and the filtrate is concentrated to dryness under reduced pressure (2.7 kPa). The residue is chromatographed on a silica gel column (0.2–0.06 mm, diameter 3 cm, height 30 cm), eluting with a mixture of cyclohexane and ethyl acetate (50/50 by volume) and collecting 50 cc fractions. Fractions 2 to 7 are combined and concentrated to dryness under reduced pressure (2.7 kPa). (3aR,7aR)-2-[(S)-2-tert-butoxycarbonylaminomethyl-2-phenylacetyl]-7,7-diphenyl-4-perhydroisoindolone (1.2 g) is obtained in the form of a white meringue.

(3aR,7aR)-2-[(S)-2-tert-butoxycarbonylaminomethyl-2-phenylacetyl]-7,7-diphenyl-4-perhydroisoindolone (1 g) is treated with a 5.7N solution (10 cc) of hydrochloric acid in dry dioxane for 2 hours at +5° C. and then for 3 hours at 20° C. The reaction mixture is concentrated to dryness under reduced pressure (2.7 kPa); the residue is crystallized from acetonitrile (5 cc). The crystals obtained are drained, washed with acetonitrile (0.5 cc) and dried. (3aR,7aR)-2-[(S)-(2-aminomethyl-2-phenyl)acetyl]-7,7-diphenyl-4-perhydroisoindolone hydrochloride (0.76 g) melting at 220° C. is obtained; $[\alpha]_D^{20} = -199°$ (c=0.2, methanol).

Sodium carbonate (10.3 g) is added, with stirring, to a suspension of (S)-3-amino-2-phenylpropionic acid (8 g) in a mixture of water (55 cc) and dioxane (100 cc) and a solution of di-tert-butyl dicarbonate (12.6 g) in dioxane (16 cc) is then poured in. The reaction mixture is stirred for 20 hours at ambient temperature and filtered and the filtrate is concentrated to dryness under reduced pressure (2.7 kPa). The residue is taken up in distilled water (100 cc) and ethyl acetate (100 cc); the mixture is cooled to +5° C. and then acidified to pH=1 by addition of 4N hydrochloric acid (35 cc). The organic phase is washed with distilled water (3×100 cc), dried over magnesium sulphate and then concentrated to dryness under reduced pressure (2.7 kPa). (S)-3-tert-butoxycarbonylamino-2-phenylpropionic acid (11.3 g) melting at 138° C. is obtained; $[\alpha]_D^{20} = +94°$ (c=0.25, methanol).

(S)-3-Amino-2-phenylpropionic acid can be prepared by a method described by J. A. Carbarino in J. Chem. Soc. Perkin 1, 906 (1981).

EXAMPLE 80

Hydroxybenzotriazole monohydrate (1 g) is added to a solution of (S)-α-methoxyphenylacetic acid (1.23 g) in dry dimethylformamide (20 cc), cooled to +5° C.; stirring is continued for 15 minutes and N,N'-dicyclohexylcarbodiimide (1.53 g) is then added. The mixture is stirred for 1 hour at +5° C. and a solution of (3aR,7aR)-7,7-diphenyl-4-perhydroisoindolone hydrochloride (2.43 g) and diisopropylethylamine (1.28 cc) in dry dimethylformamide (10 cc) is then added. The reaction mixture is stirred at +5° C. for 2 hours and then at ambient temperature for 2 hours. The reaction mixture, taken up in ethyl acetate (100 cc), is filtered; the filtrate is washed with distilled water (2×100 cc), dried over magnesium sulphate and filtered and the filtrate is concentrated to dryness under reduced pressure (2.7 kPa). The residue is chromatographed on a silica gel column (diameter 2.2 cm, height 27 cm), eluting with a mixture of cyclohexane and ethyl acetate (80/20 by volume) and collecting 20 cc fractions. Fractions 68 to 177 are combined and concentrated to dryness under reduced pressure (2.7 kPa). The residue is crystallized from isopropyl ether (15 cc); the crystals obtained are drained and then dried. (3aR,7aR)-7,7-diphenyl-2-[(S)-2-methoxy-2-phenylacetyl]-4-perhydroisoindolone (1.3 g) is obtained in the form of white crystals melting at 130° C.; $[\alpha]_D^{20} = -230°$ (c=1, methanol).

EXAMPLE 81

N,N'-Carbonyldiimidazole (1.3 g) is added to a solution of (S)-(+)-O-acetylmandelic acid (1.55 g) in dry dichloromethane (60 cc), cooled to +5° C. The mixture is stirred for 90 minutes at +5° C. and a solution of (3aR,7aR)-7,7-diphenyl-4-perhydroisoindolone hydrochloride (2.6 g) and triethylamine (1.12 cc) in dichloromethane (80 cc) is then added. The reaction mixture is stirred at 20° C. for 16 hours and concentrated to dryness under reduced pressure (2.7 kPa). The residue is taken up in a mixture of ethyl acetate (150 cc) and water (100 cc) and the organic phase is washed with water (50 cc) and then with saturated sodium chloride solution (50 cc), dried over magnesium sulphate and filtered and the filtrate is concentrated to dryness under reduced pressure (2.7 kPa). The residue is chromatographed on a silica gel column (0.4–0.063 mm, diameter 4 cm, height 23 cm), eluting under a nitrogen pressure of 0.5 bar with a mixture of cyclohexane and ethyl acetate (50/50 by volume) and collecting 60 cc fractions. Fractions 13 to 19 are combined and concentrated to dryness under reduced pressure (2.7 kPa) to give (3aR,7aR)-2-[(S)-2-acetoxy-2-phenylacetyl]-7,7-diphenyl-4-perhydroisoindolone (2.9 g) in the form of a white meringue; $[\alpha]_D^{20} = -186.4°$ (c=1.0, methanol).

Proton NMR spectrum: At ambient temperature the mixture of the two rotamers is observed. 2 and 2.05 (2S, —OCOCH₃); 1.9 to 2.3 (Mt, —CH₂— in 5 or 6); 2.6 to 3 (Mt, 4H, —CH₂— in 6 or 5 and —CH₂— in 1); 3.05 to 3.4 (Mt, 2H, 1H of the —CH₂— in 3 and —CH₂— in 3a); 3.75 to 4.1 (Mt, 1H, —CH— in 7a); 4.15 to 4.5 (Mt, 1H, 1H of the —CH₂— in 6 or 5); 5.65 and 6.14 (2S, 1H in total, —N—CO—CH—); 7.05 to 7.6 (Mt, 15H, aromatic).

Infrared spectrum (KBr), characteristic bands (cm⁻¹): 3090–3065, 2980–2880, 1735, 1720, 1660, 1600, 1585, 1495, 1460, 1445, 1435, 1375, 1240, 700.

EXAMPLE 82

A solution of (3aR,7aR)-2-[(S)-2-acetoxy-2-phenylacetyl]-7,7-diphenyl-4-perhydroisoindolone (2 g) in a mixture of water (20 cc) and ethanol (25 cc) is treated with normal sodium hydroxide solution (5 cc) and the mixture is refluxed for 1 hour, then diluted with water (100 cc) and ethyl acetate (50 cc) and neutralized by the addition of normal hydrochloric acid (5 cc). The organic phase is washed with water (50 cc) and with a saturated sodium chloride solution (50 cc), dried over magnesium sulphate and concentrated to dryness under reduced pressure (2.7 kPa) to give (3aR,7aR)-2-[(S)-2-hydroxy-2-phenylacetyl]-7,7-diphenyl-4-perhydroisoindolone (1.3 g) in the form of a white meringue.

Proton NMR spectrum: At ambient temperature the mixture of the two rotamers is observed. 1.95 to 2.45 (Mt, 2H, —CH₂— in 5 or 6); 2.6 to 3 (Mt, 4H, —CH₂— in 6 or 5 and —CH₂— in 1); 3.8 to 4 (Mt, 1H, —CH— in 7a); 4.10 to 4.35 (Mt, 1H, 1H of the —CH₂— in 3); 4.90 and 5.25 (2D, J=6, non-exchangeable, 1H in total, —N—CO—CH—O—); 5.47 and 5.6 (2D, J=6, exchangeable, 1H in total, —OH); 7 to 7.7 (Mt, 15H, aromatic).

Infrared spectrum (KBr), characteristic bands (cm⁻¹); 3410, 3100–3000, 3000–2870, 1715, 1640, 1600, 1580, 1492, 1460, 1445, 1380, 1065, 755 and 700.

(3aR,7aR)-2-[(S)-2-acetoxy-2-phenylacetyl]-7,7-diphenyl-4-perhydroisoindolone can be prepared as described above in Example 81.

EXAMPLE 83

N,N'-Carbonyldiimidazole (24.3 g) is added to a solution of monobenzyl phenylmalonate (40.5 g) in dry dichloromethane (810 cc), cooled to +5° C. The mixture is stirred for 25 minutes at +5° C. and a solution of (3aRS,7aRS)-7,7-diphenyl-4-perhydroisoindolone hydrochloride (49.1 g) and triethylamine (21 cc) in dichloromethane (1,000 cc) is then added. The reaction mixture is stirred at 20° C. for 16 hours, then washed with distilled water (3×1,000 cc), dried over magnesium sulphate and filtered and the filtrate is concentrated to dryness under reduced pressure (2.7 kPa). The residue is chromatographed on a silica gel column (0.2–0.063 mm, diameter 5.8 cm, height 63 cm), eluting with a mixture of ethyl acetate and cyclohexane (90/10 by volume) and collecting 200 cc fractions. Fractions 14 to 17 are combined and concentrated to dryness under reduced pressure (2.7 kPa). The residue is crystallized from isopropyl ether (400 cc); the crystals obtained are drained, washed with isopropyl ether (40 cc) and dried. The crystals obtained (5 g of the 35.6 g) are chromatographed on a silica gel column (0.2–0.063 mm, diameter 4.6 cm, height 30 cm), eluting with a mixture of cyclohexane and ethyl acetate (60/40 by volume) and collecting 100 cc fractions. Fractions 4 to 10 are combined and concentrated to dryness under reduced pressure (2.7 kPa); the residue is recrystallized from acetonitrile (5 cc). The crystals obtained are drained, washed with isopropyl ether (5 cc) and dried. (3aRS,7aRS)-2-(2-benzyloxycarbonyl-2-phenylacetyl)-7,7-diphenyl-4-perhydroisoindolone (1.6 g) melting at 210° C. is obtained.

EXAMPLE 84

5% palladium-on-charcoal (1 g) is added, with stirring, to a suspension of (3aRS,7aRS)-2-(2-benzyloxycarbonyl-2-phenylacetyl)-7,7-diphenyl-4-perhydroisoindolone (5 g) in methanol (50 cc). The reaction mixture is hydrogenated under atmospheric pressure and at ambient temperature for 3.5 hours and then filtered and the filtrate is concentrated to dryness under reduced pressure (2.7 kPa); the residue is treated with a 1N aqueous sodium hydroxide solution (5 cc) cooled to +5° C. and then with distilled water (40 cc) and ethyl acetate (40 cc). The aqueous solution is extracted with ethyl acetate (40 cc); the organic solutions are combined, cooled to +5° C. and acidified by addition of 4N hydrochloric acid (4 cc); the precipitate obtained is dissolved in ethyl acetate (50 cc) and the organic solution is washed with distilled water (3×40 cc), dried over magnesium sulphate and filtered and the filtrate is concentrated to dryness under reduced pressure (2.7 kPa). The residue, taken up in isopropyl ether (5 cc), is drained and dried. (3aRS,7aRS)-2-[(2-carboxy-2-phenyl)acetyl]-7,7-diphenyl-4-perhydroisoindolone (2 g) melting at 60° C. with decomposition is obtained.

(3aRS,7aRS)-2-(2-benzyloxycarbonyl-2-phenylacetyl)-7,7-diphenyl-4-perhydroisoindolone can be prepared as described above in Example 83.

EXAMPLE 85

Following the procedure described above in Example 83 but using methyl phenylmalonate as the starting material, (3aRS,7aRS)-2-[(2-methoxycarbonyl-2-phenyl)acetyl]-7,7-diphenyl-4-perhydroisoindolone (0.53 g) is obtained in the form of a white meringue.

Proton NMR spectrum: At ambient temperature the mixture of the two rotamers of each of the the two diastereoisomers is observed. 1.85 to 2.3 (Mt, 2H, —CH$_2$— in 5 or 6); 2.6 to 3.2 (Mt, 4H, —CH$_2$— in 6 or 5 and —CH$_2$— in 1); 3 to 3.5 (Mt, 2H, 1H of the —CH$_2$— in 3 and —CH— in 3a); 3.48-3.58-3.6 and 3.62 (4S, 3H in total, —COOCH$_3$); 3.65 to 4.42 (Mt, —CH— in 7a and 1H of the —CH$_2$— in 3); 4.6-4.63-5 and 5.08 (4S, 1H in total, —N—COCH—COO—); 6.9 to 7.65 (Mt, 15H, aromatic).

Infrared spectrum (KBr), characteristic bands (cm$^{-1}$): 3600–3300, 3100–3000, 3000–2800, 1745, 1715, 1650, 1600, 1580, 1495, 1475, 1445, 1400, 1195, 755, 700.

EXAMPLE 86

1-Hydroxybenzotriazole (0.825 g) and then N,N'-dicyclohexylcarbodiimide (1.25 g) are added to a solution of (L)-N-α-tert-butoxycarbonylphenylglycine (1.53 g) in dry dimethylformamide (25 cc), cooled to +5° C.; after stirring for 1 hour at the same temperature, a solution of (3aR,7aR)-7,7-diphenyl-4-perhydroisoindolone hydrochloride (2 g) and N,N-diisopropylethylamine (1.05 cc) in dimethylformamide (10 cc) is added. The reaction mixture is stirred for 2 hours at +5° C. and for 1.5 hours at 20° C. and is then diluted with ethyl acetate (250 cc) and, after filtering off the precipitate, the filtrate is washed with water (2×100 cc) and with saturated sodium chloride solution (100 cc) and dried over magnesium sulphate. After concentrating to dryness under reduced pressure (2.7 kPa), the residue is chromatographed on a silica gel column (0.2–0.063 mm, diameter 3.8 cm, height 31 cm), eluting under a nitrogen pressure of 0.5 bar with a mixture of cyclohexane and ethyl acetate (75/25 by volume) and collecting 25 cc fractions. Fractions 9 to 20 are combined and concentrated to dryness under reduced pressure (2.7 kPa) to give (3aR,7aR)-2-[(S)-2-tert-butoxycarbonylamino-2-phenylacetyl]-7,7-diphenyl-4-perhydroisoindolone (5.3 g) in the form of a white meringue.

(3aR,7aR)-2-[(S)-2-tert-butoxycarbonylamino-2-phenylacetyl]-7,7-diphenyl-4-perhydroisoindolone (5 g) is treated with a 5.7N solution (50 cc) of hydrochloric acid in dry dioxane for 30 minutes at +5° C. and then for 1 hour at 20° C. The reaction mixture is concentrated to dryness under reduced pressure (2.7 kPa) and the residue is dissolved in water (50 cc) and the solution obtained is washed with ethyl acetate (2×60 cc) and with ethyl ether (60 cc) and then filtered and the filtrate is lyophilized. The solid is taken up in water (25 cc) and the suspension is again concentrated to dryness under reduced pressure (2.7 kPa). The solid is triturated with acetone (10 cc), drained, washed with acetone (2×2.5 cc) and dried. (3aR,7aR)-7,7-diphenyl-2-[(L)-α-phenylglycyl]-4-perhydroisoindolone hydrochloride (2.53 g) is obtained in the form of a partially hydrated white solid; $[\alpha]_D^{20} = -234°$ (c=0.3, water).

Proton NMR spectrum: At ambient temperature the mixture of the two rotamers is observed. 1.75 to 2.35 (Mt, 2H, —CH$_2$— in 5 or 6); 2.6 to 3 (Mt, 4H, —CH$_2$— in 6 or 5 and —CH$_2$— in 1); 3.25 to 3.45 (Mt, partially masked, 1H of the —CH$_2$— in 3 and —CH— in 3a); 3.85 to 4.15 (Mt, 1H, —CH— in 7a); 4.25 to 4.45 (Mt, 1H, 1H of the —CH$_2$— in 3); 5.02 and 5.4 (2S, 1H in total, —N—CO—CH—N—); 6.95 to 7.65 (Mt, 14H, aromatic); 8.65 (Mf, 3H, —NH$_3$+Cl—).

Infrared spectrum (KBr), characteristic bands (cm$^{-1}$): 3600–3300, 3100–3000, 3000–2850, 3150–2500, 1715, 1655, 1595, 1580, 1495, 1475, 1445, 1440, 755, 700.

EXAMPLE 87

Carrying out the procedure in the same way as in Example 86 but using (L)-N-acetyl-α-phenylglycine as the starting material, (3aR,7aR)-2-[(S)-2-acetylamino-2-phenylacetyl]-7,7-diphenyl-4-perhydroisoindolone (0.37 g) melting at 190° C. is obtained; $[\alpha]_D^{20} = -159°$ (c=1, methanol).

EXAMPLE 88

N,N'-Carbonyldiimidazole (3.6 g) is added to a solution of (cyclohexa-1,4-dien-1-yl)acetic acid (2.35 g) in dry dichloromethane (50 cc), cooled to +5° C. The mixture is stirred for 30 minutes at +5° C. and a solution of 7,7-diphenyl-4-perhydroisoindolone hydrochloride (6.55 g) and triethylamine (5.6 cc) in dichloromethane (30 cc) is then added. The reaction mixture is stirred for 1 hour at +5° C. and then for 16 hours at 20° C. and is washed with normal hydrochloric acid (150 cc) and an aqueous saturated sodium chloride solution (150 cc).

The organic phase is dried over magnesium sulphate and filtered and the filtrate is concentrated to dryness under reduced pressure (2.7 kPa). The residue is chromatographed on a silica gel column (particle size 0.2–0.063 mm, diameter 6 cm, height 30 cm), eluting under a nitrogen pressure of 0.5 bar with a mixture (3 liters) of cyclohexane and ethyl acetate (50/50) and then with ethyl acetate (2 liters) and collecting 100 cc fractions. Fractions 10 to 48 are combined and concentrated to dryness under reduced pressure (2.7 kPa). The residue is recrystallized from acetonitrile (15 cc). The crystals are drained, washed with acetonitrile (5 cc) and isopropyl ether (25 cc) and dried. (3aRS,7aRS)-2-(cyclohexa-1,4-dien-1-yl)-acetyl-7,7-diphenyl-4-perhydroisoindolone (5.7 g) is obtained. m.p.=186° C.

EXAMPLE 89

A solution of (3aRS,7aRS)-2-(cyclohexa-1,4-dien-1-yl)acetyl-7,7-diphenyl-4-perhydroisoindolone (3.7 g) in dry dichloromethane (20 cc) is treated with triethyloxonium tetrafluoborate (1.9 g) and the mixture is stirred for 22 hours at 20° C. The crystals formed are drained, washed with dichloromethane (10 cc) and dried to give (3aRS,7aRS)-2-[1-ethoxy-2-(cyclohexa-1,4-dien-1-yl)ethylidene]-4-oxo-7,7-diphenyl-4-perhydroisoindolone tetrafluoborate (2 g) in the form of a white powder which is used in the crude state for the following stage.

A 5.4N solution (0.7 cc) of ammonia in ethanol is added to a stirred suspension of (3aRS,7aRS)-2-[1-ethoxy-2-(cyclohexa-1,4-dien-1-yl)-ethylidene]-4-oxo-7,7-diphenyl-perhydroisoindolium tetrafluoborate (2 g) in anhydrous dichloromethane (30 cc), which is cooled to −15° C. After the temperature has returned to ambient temperature, the reaction mixture is stirred for 20 hours and then washed with a 20% aqueous potassium carbonate solution (2×35 cc). The organic phase is dried over magnesium sulphate and concentrated to dryness under reduced pressure (2.7 kPa). The residue is crystallized from acetonitrile (5 cc). The crystals obtained are drained, washed with acetonitrile and dried. (3aRS,7aRS)-2-[-2-(cyclohexa-1,4-dien-1-yl)-1-iminoethyl]-7,7-diphenyl-4-perhydroisoindolone (0.6 g) is obtained in the form of white crystals. m.p.=190° C.

EXAMPLE 90

Phenylacetyl chloride (0.82 cc) is added to a solution of 7,7-diphenyl-2,3,3a,4,7,7a-hexahydro-4-1H-isoindolone hydrochloride (2 g) and triethylamine (1.7 cc) in dry dichloromethane (20 cc), cooled to +5° C. The reaction mixture is stirred for 1 hour at +5° C. and for 1 hour at ambient temperature; it is washed with distilled water (2×20 cc), dried over magnesium sulphate and filtered and the filtrate is concentrated to dryness under reduced pressure (2.7 kPa). The residue is crystallized from acetonitrile (15 cc). The crystlas are drained, washed with isopropyl ether (10 cc) and dried and are then recrystallized from acetonitrile (20 cc). The crystals obtained are drained and dried. (3aRS,7aRS)-7,7-diphenyl-2-phenylacetyl-2,3,3a,7,7a-hexahydro-4-1H-isoindolone (2.7 g) melting at 188° C. is obtained.

7,7-Diphenyl-2,3,3a,4,7,7a-hexahydro-4-1H-isoindolone hydrochloride can be prepared in the following way:

A mixture of 2-benzyl-7,7-diphenyl-2,3,3a,4,7,7a-hexahydro-4-1H-isoindolone (3.4 g) and vinyl chloroformate (0.92 cc) in 1,2-dichloroethane (80 cc) is refluxed for 1 hour; the reaction mixture is concentrated to dryness under reduced pressure (2.7 kPa). The residue is crystallized from ethyl ether (20 cc). 7,7-Diphenyl-2-vinyloxycarbonyl-2,3,3a,4,7,7a-hexahydro-4-1H-isoindolone (2.6 g) melting at 162° C. is obtained.

7,7-Diphenyl-2-vinyloxycarbonyl-2,3,3a,4,7,7a-hexahydro-4-1H-isoindolone (2.6 g) is stirred in a 3N solution (30 cc) of hydrochloric acid in dioxane at ambient temperature for 30 minutes; the mixture is concentrated to dryness under reduced pressure (2.7 kPa). The residue is taken up in ethanol (50 cc) and refluxed for 30 minutes; the mixture is concentrated to dryness under reduced pressure (2.7 kPa). The residue is crystallized from ethyl ether (20 cc); the crystals obtained are drained and dried. 7,7-Diphenyl-2,3,3a,4,7,7a-hexahydro-4-1H-isoindolone (2 g) melting at a temperature higher than 260° C. is obtained.

(3aRS,7aRS)-2-Benzyl-7,7-diphenyl-2,3,3a,4,7,7a-hexahydro-4-1H-isoindolone can be obtained in the following way:

Trifluoroacetic acid (2 drops) is added to a solution of 4,4-diphenyl-cyclohexa-2,5-dien-1-one (7.7 g) and N-butoxymethyl-N-trimethylsilylmethylbenzylamine (11 cc) in dry dichloromethane (80 cc) and the reaction mixture is refluxed for 1 hour and a half. Additional N-butoxymethyl-N-trimethylsilylmethylbenzylamine (5 cc) and trifluoroacetic acid (2 drops) are added and the reaction mixture is heated for 1 hour and a half. The reaction mixture is treated with potassium carbonate (3 g) and filtered and the filtrate is concentrated to dryness under reduced pressure (2.7 kPa). The residue is crystallized from isopropyl ether (15 cc). The crystals obtained are drained, washed with isopropyl ether (2×5 cc) and dried; (3aRS,7aRS)-2-benzyl-7,7-diphenyl-2,3,3a,4,7,7a-hexahydro-4-1H-isoindolone (4.4 g) melting at 132° C. is obtained.

4,4-Diphenyl-cyclohexa-2,5-dien-1-one can be prepared by the method of H. E. Zimmermann and D. I. Schuster J. Am. Chem. Soc., 84, 527 (1962).

EXAMPLE 91

A suspension of 7,7-bis-(3-fluorophenyl)-4-perhydroisoindole hydrochloride (1.5 g) in dichloromethane (30 cc) cooled to +4° C. is treated with triethylamine (1.15 cc) and then with phenylacetyl chloride (0.63 g). The reaction mixture is stirred for 5 hours at 25° C. and then washed with water (3×100 cc). The organic phase is dried over magnesium sulphate and filtered and the filtrate is concentrated to dryness under reduced pressure (2.7 kPa). The residue is chromatographed on a silica gel column (particle size 0.04–0.063 mm, diameter 2.3 cm, height 25 cm), eluting under a nitrogen pressure of 0.5 bar with a mixture of cyclohexane and ethyl acetate (55/45) to give a meringue (1.21 g) which is crystallized by addition of isopropyl ether (10 cc). The crystals are drained, washed with isopropyl ether and dried. (3aRS,7aRS)-7,7-bis-(3-fluorophenyl)-2-(phenylacetyl)-4-perhydroisoindolone (0.76 g) is obtained. m.p.=108° C.

7,7-bis-(3-fluorophenyl)-4-perhydroisoindolone hydrochloride can be obtained in the following way:

A solution of (3aRS,7aRS)-2-benzyl-7,7-bis-(3-fluorophenyl)-4-perhydroisoindolone (92.2 g) in 1,2-dichloroethane (860 cc) is treated with vinyl chloroformate (26.3 cc) and the mixture is refluxed for 3 hours and then concentrated under reduced pressure (2.7 kPa). The residue is chromatographed (in two passes) on silica gel (particle size 0.04–0.063 mm, columns 8 cm in diameter and 35 cm high), eluting under a nitrogen pressure of 0.5 bar with a mixture of cyclohexane and ethyl acetate (75/25). The meringue obtained is crystallized from isopropyl ether to give (3aRS,7aRS)-7,7-bis-(3-fluorophenyl)-2-vinyloxycarbonyl-4-perhydroisoindolone (50.3 g). m.p.=152° C.

(3aRS,7aRS)-7,7-bis-(3-fluorophenyl)-2-vinyloxycarbonyl-4-perhydroisoindolone (64.5 g) is treated with a 6N solution (330 cc) of hydrochloric acid in dioxane for 30 minutes at 25° C. The solution is concentrated to dryness under reduced pressure (2.7 kPa) and the residue is taken up in ethanol (500 cc). The solution is heated at 60° C. for 6 hours and stirred for 16 hours at 25° C. and then concentrated to half its volume under reduced pressure (2.7 kPa) and the crystals formed are drained and washed with isopropyl ether and then dried. 7,7-Bis(3-Fluorophenyl)-4-perhydroisoindolone hydrochloride (48.7 g) is obtained. m.p.=264° C.

(3aRS,7aRS)-2-Benzyl-7,7-bis-(3-fluorophenyl)-4-perhydroisoindolone can be obtained in the following way:

Trifluoroacetic acid (3 cc) is added to a solution of 4,4-bis-(3-fluorophenyl)cyclohexenone (90.3 g) and N-butoxymethyl-N-trimethylsilylmethylbenzylamine (123 cc) in dry dichloromethane (1,000 cc). The reaction mixture is brought to reflux and then stirred for 2 hours allowing the temperature to return to 25° C. and is then stirred for a further 15 minutes after addition of potassium carbonate (60 g). After filtering and concentrating the filtrate to dryness under reduced pressure (2.7 kPa), the crystallized residue is scraped with isopropyl ether, drained, washed and recrystallized from cyclohexane (300 cc). The crystals are drained, washed with cyclohexane (2×15 cc) and dried to give (3aRS,7aRS)-2-benzyl-7,7-bis-(3-fluorophenyl)-4-perhydroisoindolone (92 g) in the form of white crystals. m.p.=124° C.

4,4-bis-(3-Fluorophenyl)cyclohexenone can be obtained in the following way:

Butenone (50.4 cc) is added to a solution of bis-(3-fluorophenyl)acetaldehyde (144.5 g) in ethyl ether (500 cc) and then, after cooling to 0° C., a solution of potassium hydroxide (13.9 g) in ethanol (89 cc) is added dropwise. The reaction mixture is stirred for 2 h at 0° C. and then for 16 hours at 25° C. and diluted with ethyl acetate (300 cc) and water (500 cc). The aqueous phase is washed with ethyl acetate (300 cc). The combined organic phases are washed with saturated sodium chloride solution (500 cc), dried over magnesium sulphate and concentrated under reduced pressure (2.7 kPa). The residue is chromatographed (in two passes) on silica gel (particle size 0.04-0.063 mm, columns 8.5 cm in diameter and 34 cm high), eluting under a nitrogen pressure of 0.5 bar with a mixture of cyclohexane and ethyl acetate (90/10). 4,4-bis-(3-Fluorophenyl)-cyclohexenone (90.3 g) is obtained in the form of white crystals. m.p.=95° C.

bis-(3-Fluorophenyl)acetaldehyde can be obtained in the following way:

A solution of 1,1-bis-(3-fluorophenyl)-2-methoxyethanol (156.7 g) (obtained by reaction of (3-fluorophenyl)magnesium bromide on methyl 2-methoxyacetate in THF) in formic acid (160 cc) is refluxed for 16 hours, cooled and poured into a mixture of saturated sodium carbonate solution (800 cc) and ethyl acetate (500 cc). The organic phase is washed with water (2×500 cc) and with saturated sodium chloride solution (500 cc) and then dried and concentrated to dryness under reduced pressure (2.7 kPa) to give bis-(3-fluorophenyl)acetaldehyde (144.5 g) in the form of a yellow oil.

EXAMPLE 92

A solution of (2-methoxyphenyl)acetic acid (0.46 g) in dry dichloromethane (15 cc) is cooled to 0° C. and then treated with N,N'-carbonyldiimidazole (0.45 g) and stirred for 1 hour at 0° C. A solution of 7,7-bis-(3-fluorophenyl)-4-perhydroisoindolone hydrochloride (1 g) and triethylamine (0.76 cc) in dichloromethane (20 cc) is added dropwise. The reaction mixture is stirred for 3 hours at 25° C. and then washed with water (2×50 cc) and with saturated sodium chloride solution (50 cc). The organic phase is dried over magnesium sulphate and filtered and the filtrate is concentrated to dryness under reduced pressure (2.7 kPa). The residue is chromatographed on a silica gel column (particle size 0.04-0.063 mm, diameter 2.2 cm, height 23 cm), eluting under a nitrogen pressure of 0.5 bar with a mixture of cyclohexane and ethyl acetate (70/30) and collecting 15 cc fractions. Fractions 4 to 9 are combined and concentrated to dryness under reduced pressure (2.7 kPa) and the product obtained is recrystallized from acetonitrile. The crystals are drained, washed with isopropyl ether and dried. (3aRS,7aRS)-7,7-bis-(3-fluorophenyl)-2-(phenylacetyl)-4-perhydroisoindolone (0.76 g) is obtained. m.p.=194° C.

EXAMPLE 93

N,N'-carbonyldiimidazole (0.59 g) is added to a solution of (2-dimethylaminophenyl)acetic acid (0.65 g) in dry dichloromethane (20 cc) cooled to +4° C. The mixture is stirred for 90 minutes at 25° C. and a solution of 7,7-bis-(3-fluorophenyl)-4-perhydroisoindolone hydrochloride (1.3 g) and triethylamine (1.02 cc) in dry dichloromethane (25 cc) is then added dropwise. The reaction mixture is stirred for 16 hours at 25° C. and washed with water (2×250 cc) and with saturated sodium chloride solution (250 cc). The organic phase is dried over magnesium sulphate and concentrated to dryness under reduced pressure (2.7 kPa). The residue is chromatographed on a silica gel column (particle size 0.04-0.063 mm, diameter 2.3 cm, height 23 cm), eluting under a nitrogen pressure of 0.5 bar with a mixture of cyclohexane and ethyl acetate (55/45) and collecting 15 cc fractions. Fractions 6 to 18 are combined and concentrated to dryness under reduced pressure (2.7 kPa). The residue is solidified using isopropyl ether to give (3aRS,7aRS)-7,7-bis-(3-fluorophenyl)-2-(2-dimethylaminophenyl)acetyl-4-perhydroisoindolone (0.6 g), from which the hydrochloride is prepared by dissolving in ethyl acetate (1 cc) and adding a 3N solution of hydrochloric acid in isopropyl ether. The precipitate is drained, washed with isopropyl ether and dried. (3aRS,7aRS)-7,7-bis-(3-fluorophenyl)-2-(2-dimethylaminophenyl)acetyl-4-perhydroisoindolone hydrochloride (0.48 g) is obtained in the form of a white solid.

Proton NMR spectrum (DMSO-$d_6$/AcOD 90/10). At ordinary temperature the mixture of the two rotamers is observed. 2 to 2.32 (m, 2H, —$CH_2$— in 5); 2.37 and 2.6 (2s, 3H each, —$N(CH_3)_2$); 2.65 to 3 (m, 4H, —$CH_2$— in 6 and —$CH_2$— in 1); 3.15 to 3.3 (m, 1H, H in 3a); 3.35 and 3.47 (2m, 1H, 1H in 3); 3.35 and 3.5 (2d, J=15, Ar$CH_2$CO of a rotamer); 3.67 (s, Ar$CH_2$CO of the other rotamer); 4 (m, 1H, H in 7a); 4.2 and 4.25 (2m, J=11, 1H, 1H in 3); 6.9 to 7.6 (m, 12H, aromatic)

Infrared spectrum (characteristic bands in $cm^{-1}$): 3500-3150, 3100-3000, 3000-2850, 1712, 1650, 1615, 1595, 1580, 1495, 1445, 1535, 755, 700.

EXAMPLE 94

N,N-Carbonyldiimidazole (0.44 g) is added to a solution of (2-dimethylaminophenyl)acetic acid (0.49 g) in dry dichloromethane (20 cc) cooled to +4° C. The mixture is stirred for 1 hour at 25° C. and a solution of 7.7-bis-(2-fluorophenyl)-4-perhydroisoindolone hydrochloride (1 g) and triethylamine (0.76 cc) in dry dichloromethane (25 cc) is then added dropwise. The reaction mixture is stirred for 20 hours at 25° C. and washed with water (2×100 cc) and with saturated sodium chloride solution (100 cc). The organic phase is dried over magnesium sulphate and concentrated to dryness under reduced pressure (2.7 kPa). The residue is chromatographed on a silica gel column (particle size 0.04–0.063 mm, diameter 2 cm, height 23 cm), eluting under a nitrogen pressure of 0.5 bar with a mixture of cyclohexane and ethyl acetate (50/50) and collecting 10 cc fractions. Fractions 14 to 36 are combined and concentrated to dryness under reduced pressure (2.7 kPa) to give (3aRS,7aRS)-7,7-bis-(2-fluorophenyl)-2-(2-(dimethylaminophenyl)acetyl-4-perhydroisoindolone (1 g), from which the hydrochloride is prepared by dissolving in ethyl acetate (2 cc) and adding a 3N solution of hydrochloric acid in isopropyl ether. The precipitate is drained, washed with isopropyl ether and dried. (3aRS,7aRS)-7,7-bis-(2-fluorophenyl)-2-(2-dimethylaminophenyl)acetyl-4-perhydroisoindolone hydrochloride (0.87 g) is obtained in the form of a white solid.

Proton NMR spectrum (DMSO-$d_6$/AcOD 90/10): At ambient temperature the mixture of the two rotamers is observed: 2.1 to 2.35 (m, 2H, —$CH_2$— in 5); 2.8 to 3.4 (m, 10H, —$CH_2$— in 1 and in 6, N($CH_3$)$_2$); 3.7 and 3.5 (2 dd wide, 1H, H in 3a); 3.8 (dd wide, 1H, 1H in 3); 4.05 (s wide, 2H, —$CH_2$CO); 4.1 (m, wide, 1H, H in 7a); 4.2 and 4.45 (d, 1H, 1H in 3); 7 to 8 (m, 12H aromatic).

(3aRS,7aRS)-7,7-bis-(2-Fluorophenyl)-4-perhydroisoindolone hydrochloride can be prepared in the following way: A solution of (3aRS,7aRS)-2-benzyl-7,7-bis-(2-fluorophenyl)-4-perhydroisoindolone (2.34 g) in methanol (100 cc) to which N hydrochloric acid (6.2 cc) has been added is hydrogenated under atmospheric pressure in the presence of 10% palladium-on-charcoal (0.4 g) for 5 hours at 25° C. The reaction mixture is filtered and the filtrate is concentrated under reduced pressure (2.7 kPa) to give (3aRS,7aRS)-7,7-bis-(2-fluorophenyl)-4-perhydroisoindolone hydrochloride (2 g) in the form of white solid.

Proton NMR spectrum (DMSO-$d_6$): 2 to 2.4 (m, 2H, —$CH_2$— in 5); 2.7 to 3 (m, 4H, —$CH_2$— in 1 and in 6); 3.5 (dd wide, 1H, 1H in 3); 3.7 (dd wide, 1H, H in 3a); 3.9 (d wide, 1H, 1H in 3); 4.2 (m, 1H, H in 7a); 7.1 to 8 (m, 8H aromatic).

(3aRS,7aRS)-2-Benzyl-7,7-bis-(2-fluorophenyl)-4-perhydroisoindolone can be obtained in the following way:

Trifluoroacetic acid (3 drops) is added to a solution of 4,4-bis-(2-fluorophenyl)-cyclohexenone (4.3 g) and N-butoxymethyl-N-trimethylsilylmethylbenzylamine (5.8 cc) in dry dichloromethane (30 cc). The reaction mixture is brought to reflux and then stirred for 16 hours after having allowed the temperature to return to 25° C. N-Butoxymethyl-N-trimethylsilymethylbenzylamine (2.5 cc) and trifluoroacetic acid (3 drops) are added and the mixture is stirred for 3 hours under reflux. The reaction mixture is treated with potassium carbonate (3 g) and stirred for 15 minutes. After filtering and concentrating the filtrate to dryness under reduced pressure (2.7 kPa), the residue is chromatographed on a silica gel column (particle size 0.04–0.063 mm, diameter 4 cm, height 32 cm), eluting under a nitrogen pressure of 0.5 bar with a mixture of cyclohexane and ethyl acetate (85/15) and collecting 20 cc fractions. Fractions 13 to 22 are combined and concentrated to dryness under reduced pressure (2.7 kPa) to give (3aRS,7aRS)-2-benzyl-7,7-bis-(2-fluorophenyl)-4-perhydroisoindolone (2.28 g). m.p.=138° C.

4,4-bis-(2-Fluorophenyl)-cyclohexenone can be obtained in the following way:

Potassium carbonate (26.9 g) is added to a solution of bis-(2-fluorophenyl)acetaldehyde (30.8 g) in 1,2-dimethoxyethane (135 cc) and, after cooling to −50° C., butenone (19.9 cc) is then added dropwise. The reaction mixture is stirred for 12 h at −50° C. and then for 6 hours at 25° C. and diluted with ethyl acetate (250 cc) and water (200 cc). The organic phase is washed with water (3×200 cc) and then with saturated sodium chloride solution (200 cc), dried over magnesium sulphate and concentrated under reduced pressure (2.7 kPa). The residue is chromatographed on a silica gel column (particle size 0.04–0.063 mm, diameter 5.5 cm, height 50 cm), eluting under a nitrogen pressure of 0.5 bar with a mixture of cyclohexane and ethyl acetate (90/10). 2,2-bis-(2-Fluorophenyl)-5-oxohexanal (9 g) is obtained in the form of a yellow oil. A solution of this compound (6.65 g) in toluene (100 cc) containing paratoluenesulphonic acid (1.5 g) is refluxed for 3 hours, washed with water (2×100 cc) and then with saturated sodium chloride solution (100 cc), dried over magnesium sulphate and concentrated under reduced pressure (2.7 kPa). The residue is chromatographed on a silica gel column (particle size 0.04–0.063 mm, diameter 4 cm, height 30 cm), eluting under a nitrogen pressure of 0.5 bar with a mixture of cyclohexane and ethyl acetate (90/10) and collecting 15 cc fractions. Fractions 21 to 26 are combined and concentrated to dryness under reduced pressure (2.7 kPa) to give 4,4-bis-(2-fluorophenyl)-cyclohexenone (2.83 g) in the form of yellow oil.

Proton NMR spectrum (DMSO-$d_6$): 2.6 (m, 2H, —$CH_2$— in 5); 2.8 (dd wide, 2H, —$CH_2$— in 6); 6.2 (d, 1H, H in 2); 6.9 to 7.4 (m, 9H aromatic and H in 3).

bis-(2-Fluorophenyl)acetaldehyde can be prepared in the following way:

A solution of 1,2-bis-(2-fluorophenyl)oxirane (26.3 g) in toluene (500 cc) is treated dropwise with boron trifluoride etherate (7 cc) and the mixture is stirred for 2 hours at 25° C. and then washed with water (50 cc) and saturated sodium bicarbonate solution (50 cc). After drying over magnesium sulphate and concentrating to dryness under reduced pressure (2.7 kPa), bis-(2-fluorophenyl)acetaldehyde (25 g) is obtained in the form of a yellow oil.

1,2-bis-(2-Fluorophenyl)oxirane can be prepared by the method described by V. Mark (J. Am. Chem. Soc., 85, 1984 (1963)).

EXAMPLE 95

Triethylamine (0.45 cc) and then phenylacetyl chloride (0.49 g) are added to a solution of 7,7-bis-(3-chlorophenyl)-4-perhydroisoindolone hydrochloride (1.06 g) in dichloromethane (20 cc) cooled to +4° C. The reactio mixture is stirred for 2 hours at 25° C. and then washed with water (3×30 cc) and with saturated sodium chloride solution (3×30 cc). The organic phase is dried over magnesium sulphate and filtered and the filtrate is concentrated to dryness under reduced pressure (2.7 kPa). The residue is chromatographed on a silica gel column (particle size 0.04–0.063 mm, diameter 2.2 cm, height 23 cm), eluting under a nitrogen pressure of 0.5 bar with a mixture of cyclohexane and ethyl acetate (55/45 by volume) and collecting 15 cc fractions. Fractions 7 to 18 are concentrated to dryness under reduced pressure (2.7 kPa) and the residue is crystallized from acetonitrile. The crystals are drained, washed with isopropyl ether and dried. (3aRS,7aRS)-7,7-bis-(3-chlorophenyl)-2-(phenylacetyl)-4-perhydroisoindolone (0.21 g) is obtained. m.p.=160° C.

7,7-bis-(3-Chlorophenyl)-4-perhydroisoindolone hydrochloride can be prepared in the following way:

A solution of (3aRS,7aRS)-2-benzyl-7,7-bis-(3-chlorophenyl)-4-perhydroisoindolone (11.5 g) in 1,2-dichloroethane (250 cc) is treated with vinyl chloroformate (2.8 cc) and refluxed for 16 hours and then concentrated under reduced pressure (2.7 kPa). The residue is chromatographed on a silica gel column (particle size 0.04–0.063 mm, diameter 6 cm, height 32 cm), eluting under a nitrogen pressure of 0.5 bar with a mixture of cyclohexane and ethyl acetate (80/20) and collecting 25 cc fractions. Fractions 19 to 27 are combined and concentrated to dryness under reduced pressure (2.7 kPa). The meringue obtained is solidified in isopropyl ether and the precipitate is drained, washed with isopropyl ether and dried to give (3aRS,7aRS)-7,7-bis-(3-chlorophenyl)-2-vinyloxycarbonyl-4-perhydroisoindolone (6.7 g) in the form of a white solid.

Proton NMR spectrum (DMSO-$d_6$): 2.1 and 2.3 (2 ddd wide, 2H, —$CH_2$— in 5); 2.7 to 3 (m, 4H, —$CH_2$— in 1 and in 6); 3.3 (m, 1H, H in 3a); 3.45 (dd wide, 1H, 1H in 3); 4.1 (m, 2H, H in 7a and 1H in 3); 4.45 and 4.70 (2 d wide, 2H, =$CH_2$ of the vinyl); 7.05 ((dd, 1H, OCH= of the vinyl)); 7.2 to 7.7 (m, 8H aromatic).

(3aRS,7aRS)-7,7-bis-(3-chlorophenyl)-2-vinyloxycarbonyl-4-perhydroisoindolone (1.5 g) is treated with a 6N solution (7.4 cc) of hydrochloric acid in dioxane for 2 hours at 25° C. The solution is concentrated to dryness under reduced pressure (2.7 kPa) and the residue is heated for 1 hour in solution in ethanol at 60° C. and then stirred for 6 hours at 25° C. The solution is concentrated to dryness under reduced pressure (2.7 kPa) and the meringue obtained is solidified in isopropyl ether. The precipitate is drained and washed with isopropyl ether and then dried to give 7,7-bis-(3-chlorophenyl)-4-perhydroisoindolone hydrochloride (1 g).

Proton NMR spectrum (DMSO-$d_6$): 2 to 2.4 (m, 2H, —$CH_2$— in 5); 2.55 to 2.9 (m, 2H, —$CH_2$— in 6); 3.3 (dd wide, 1H, 1H in 3); 3.5 (m, 1H, H in 3a); 3.85 (d wide, 1H, 1H in 3); 3.95 (m, 1H, H in 7a); 7.1 to 7.76 (m, 8H aromatic).

(3aRS,7aRS)-2-Benzyl-7,7-bis-(3-chlorophenyl)-4-perhydroisoindolone can be obtained in the following way:

Trifluoroacetic acid (15 drops) is added to a solution of 4,4-bis-(3-chlorophenyl)-cyclohexenone (26.8 g) and N-butoxymethyl-N-trimethylsilylmethylbenzylamine (33 cc) in dry dichloromethane (200 cc). The reaction mixture is brought to reflux and then stirred for 16 hours after having allowed the temperature to return to 25° C. and for a further 15 minutes after addition of potassium carbonate (16 g). After filtering and concentrating the filtrate to dryness under reduced pressure (2.7 kPa), the residue is chromatographed on a silica gel column (particle size 0.04–0.063 mm, diameter 7 cm, height 40 cm), eluting under a nitrogen pressure of 0.5 bar with a mixture of cyclohexane and ethyl acetate (75/25 by volume) and collecting 500 cc fractions. Fractions 12 to 18 are combined and concentrated to dryness under reduced pressure (2.7 kPa) to give (3aRS,7aRS)-2-benzyl-7,7-bis-(3-chlorophenyl)-4-perhydroisoindolone (16.2 g) in the form of a yellow oil.

Proton NMR spectrum: (DMSO-$d_6$): 1.75 (ddd, 1H) and 2.1 to 2.45 (m, 3H): —$CH_2$— in 5 and in 6); 2.7 to 2.9 (m, 4H: —$CH_2$— in 1 and in 3); 3.1 (m, 1H, H in 3a); 3.5 (AB, 2H, benzyl—$CH_2$—); 3.8 (dd wide, 1H, H in 7a); 7.1 to 7.5 (m, 13H aromatic).

4,4-bis-(3-Chlorophenyl)-cyclohexenone can be obtained in the following way:

Butenone (11.3 cc) is added to a solution of bis-(3-chlorophenyl)acetaldehyde (36.9 g) in ethyl ether (200 cc) and then, after cooling to 0° C., a solution of potassium hydroxide (3.1 g) in ethanol (20 cc) is added dropwise. The reaction mixture is stirred for 2 h at 0° C. and then for 16 hours at 25° C. and diluted with ethyl acetate (100 cc) and water (200 cc). The aqueous phase is washed with ethyl acetate (100 cc). The combined organic phases are washed with saturated sodium chloride solution (3×100 cc), dried over magnesium sulphate and concentrated under reduced pressure (2.7 kPa). The residue is chromatographed on a silica gel column (particle size 0.04–0.063 mm, diameter 7 cm, height 42 cm), eluting under a nitrogen pressure of 0.5 bar with a mixture of cyclohexane and ethyl acetate (90/10 by volume). 4,4-bis-(3-Chlorophenyl)cyclohexenone (27.7 g) is obtained in the form of yellow oil.

Proton NMR spectrum (DMSO-$d_6$): 2.3 (dd wide, 2H, —$CH_2$— in 5); 2.7 (dd wide, 2H, —$CH_2$— in 6); 6.2 (d, 1H, H in 2); 7.2 to 7.4 (m, 8H aromatic); 7.6 (d, 1H, H in 3).

bis-(3-Chlorophenyl)acetaldehyde can be obtained in the following way:

A solution of 1,1-bis-(3-chlorophenyl)-2-methoxyethanol (47 g) (obtained by reaction of (3-chlorophenyl)-magnesium bromide on methyl 2-methoxyacetate in tetrahydrofuran) in formic acid (44 cc) is refluxed for 5 hours, cooled and poured into a mixture of saturated sodium carbonate solution (500 cc) and ethyl acetate (300 cc). The organic phase is washed with water (3×250 cc) and with saturated sodium chloride solution (200 cc), then dried and concentrated to dryness under reduced pressure (2.7 kPa) to give bis-(3-chlorophenyl)acetaldehyde (36.9 g) in the form of a yellow oil.

EXAMPLE 96

(2-Dimethylaminophenyl)acetic acid (1.1 g), 1-hydroxybenzotriazole (0.09 g) and diisopropylethylamine (1.06 cc) are added to a solution of 7,7-bis-3-chlorophenyl)-4-perhydroisoindolone hydrochloride (2.45 g) in dry dichloromethane (50 cc) cooled to +4° C. and a solution of 1-(3-dimethylaminopyl)-3-ethylcarbodiimide (1.3 g) in dry dichloromethane (100 cc) is then added dropwise. The reaction mixture is stirred for 5 hours at 0° C. and then for 16 hours at 25° C. and washed with water (2×250 cc) and with saturated sodium chloride solution (250 cc). The organic phase is dried over magnesium sulphate and concentrated to dryness under reduced pressure (2.7 kPa). The residue is chromatographed on a silica gel column (particle size 0.04–0.063 mm, diameter 3 cm, height 22 cm), eluting under a nitrogen pressure of 0.5 bar with a mixture of cyclohexane and ethyl acetate (55/45 by volume) and collecting 20 cc fractions. Fractions 13 to 24 are combined and concentrated to dryness under reduced pressure (2.7 kPa) to give (3aRS,7aRS)-7,7-bis-(3-chlorophenyl)-2-(2-dimethylaminophenyl)acetyl-4-perhydroisoindolone (2.3 g), from which the hydrochloride is prepared by dissolving in ethyl acetate (2 cc) and adding a 3N solution of hydrochloric acid in isopropyl ether. The precipitate is drained, washed with isopropyl ether and dried. (3aRS,7aRS)-7,7-bis-(3-chlorophenyl)-2-(2-dimethylaminophenyl)acetyl-4-perhydroisoindolone hydrochloride (1.94 g) is obtained in the form of a white solid.

Proton NMR spectrum (DMSO-$d_6$/CH$_3$COOD 90/10; at ambient temperature the mixture of the two rotamers is observed: 2.1 and 2.3 (m, 2H, —CH$_2$— in 5); 2.5 to 3.5 (m, 11H, —CH$_2$— in 1 and in 6, N(CH$_3$)$_2$ and H in 3a); 3.7 (m, 1H, 1H in 3); 4 (m, 3H, H in 7a and —CH$_2$CO); 4.4 and 4.2 (2 d, 1H, 1H in 3); 7.1 to 7.8 (m, 12H aromatic).

EXAMPLE 97

A suspension of (3aRS,7aRS)-7,7-bis-(3-tolyl)-4-perhydroisoindolone hydrochloride (1.5 g) in dichloromethane (30 cc) cooled to +4° C. is treated with triethylamine (1.15 cc) and then with phenylacetyl chloride (0.63 g). The reaction mixture is stirred for 5 hours at 25° C. and then washed with water (3×100 cc). The organic phase is dried over magnesium sulphate and filtered and the filtrate is concentrated to dryness under reduced pressure (2.7 kPa). The residue is crystallized twice from acetonitrile to give (3aRS,7aRS)-7,7-bis-(3-tolyl)-2-(phenylacetyl)-4-perhydroisoindolone (0.36 g). m.p.=207° C.

7,7-bis-(3-Tolyl)-4-perhydroisoindolone hydrochloride can be obtained in the following way:

A solution of (3aRS,7aRS)-2-benzyl-7,7-bis-(3-tolyl)-4-perhydroisoindolone (13.7 g) in 1,2-dichloroethane (150 cc) is treated with vinyl chloroformate (3.7 cc) and the mixture is refluxed for 3 hours and then concentrated under reduced pressure (2.7 kPa). The residue is chromatographed on silica gel (particle size 0.04–0.063 mm, column 5.4 cm in diameter and 39 cm high), eluting under a nitrogen pressure of 0.5 bar with a mixture of cyclohexane and ethyl acetate (80/20). Fractions 23 to 39 are combined and concentrated to dryness under reduced pressure (2.7 kPa) to give (3aRS,7aRS)-7,7-bis-(3-tolyl)-2-vinyloxycarbonyl-4-perhydroisoindolone (7.4 g) in the form of a white meringue.

Proton NMR spectrum (DMSO-$d_6$/CH$_3$COOD 90/10: At ordinary temperature the mixture of the two rotamers is observed. 1.95 to 2.4 (m, 2H, —CH$_2$— in 5); 2.27 and 2.32 (2s, 6H, ArCH$_3$); 2.4 to 2.95 (m, 4H, —CH$_2$— in 1 and in 6); 3.2 to 3.5 (m, 2H, H in 3a and 1H in 3); 4.03 (m, 1H H in 7a); 4.09 and 4.16 (2d wide, 1H, H in 3); 4.35 to 4.85 (4d wide, 2H, =CH$_2$ of the vinyl); 6.9 to 7.5 (m, 9H, aromatic and OCH= of the vinyl).

(3aRS,7aRS)-7,7-bis-(3-tolyl)-2-vinyloxycarbonyl-4-perhydroisoindolone (7.4 g) is treated with a 6N solution (39 cc) of hydrochloric acid in dioxane for 30 minutes at 25° C. The solution is concentrated to dryness under reduced pressure (2.7 kPa) and the residue is taken up in ethanol (100 cc). The solution is heated at 60° C. for 2 hours and stirred for 16 hours at 25° C. and then concentrated to dryness under reduced pressure (2.7 kPa). The residue is solidified using isopropyl ether and the solid is washed, drained and dried. 7,7-bis-(3-Tolyl)-4-perhydroisoindolone hydrochloride (6.36 g) is obtained in the form of a yellow solid.

Proton NMR spectrum (DMSO-$d_6$/CH$_3$COOD 90/10: 1.95 to 2.35 (m, 2H, —CH$_2$— in 5); 2.24 and 2.3 (2s, 6H, ArCH$_3$); 2.4 to 2.9 (m, 4H, —CH$_2$— in 6 and in 1); 3.3 (dd wide, 1H, 1H in 3); 3.48 (m, 1H, H in 3a); 3.85 (d wide, 1H, 1H in 3); 3.90 (m, 1H, H in 7a); 6.9 to 7.4 (m, 8H aromatic).

(3aRS,7aRS)-2-Benzyl-7,7-bis-(3-tolyl)-4-perhydroisoindolone can be obtained in the following way:

Trifluoroacetic acid (12 drops) is added to a solution of 4,4-bis-(3-tolyl)cyclohexenone (16.7 g) and N-butoxymethyl-N-trimethylsilylmethylbenzylamine (18.7 cc) in dry dichloromethane (150 cc). The reaction mixture is brought to reflux and then stirred for 3 hours allowing the temperature to return to 25° C. and for a further 10 minutes after addition of potassium carbonate (12 g). After filtering and concentrating the filtrate to dryness under reduced pressure (2.7 kPa), the residue is chromatographed on a silica gel column (particle size 0.04–0.063 mm, diameter 5 cm, height 50 cm), eluting under a nitrogen pressure of 0.7 bar with a mixture of cyclohexane and ethyl acetate (85/15 by volume) and collecting 25 cc fractions. Fractions 14 to 30 are combined and concentrated to dryness under reduced pressure (2.7 kPa) to give (3aRS,7aRS)-2-benzyl-7,7-bis-(3-tolyl)-4-perhydroisoindolone (13.9 g) in the form of white crystals.

Proton NMR spectrum (CDCl$_3$): 1.98 (ddd, 1H) and 2.2 to 2.5 (m, 3H): —CH$_2$— in 5 and in 6); (s, 6H, ArCH$_3$); 2.5 to 3.05 (m, 4H, —CH$_2$— in 1 and in 3); 3.2 (m, 1H, H in 3a); 3.45 and 3.65 (AB, 2H, —CH$_2$— Ar); 3.7 (m, 1H, H in 7a); 6.9 to 7.4 (m, 13H aromatic).

4,4-bis-(3-Tolyl)cyclohexenone can be obtained in the following way:

Butenone (7.23 cc) is added to a solution of bis-(3-tolyl)acetaldehyde (20.4 g) in ethyl ether (110 cc) and then, after cooling to 0° C., a solution of potassium hydroxide (2 g) in ethanol (12.7 cc) is added dropwise. The reaction mixture is stirred for 2 hours at 0° C. and then for 16 hours at 25° C. and diluted with ethyl acetate (200 cc) and water (200 cc). The aqueous phase is washed with ethyl acetate (2×250 cc). The combined organic phases are washed with water (2×250 cc) and then with saturated sodium chloride solution (250 cc), dried over magnesium sulphate and concentrated under reduced pressure (2.7 kPa). The residue is chromatographed on silica gel (particle size 0.04–0.063 mm, column 5.4 cm in diameter and 40 cm high), eluting under a nitrogen pressure of 0.5 bar with a mixture of cyclohexane and ethyl acetate (85/15 by volume). 4,4-bis-(3-Tolyl)-cyclohexenone (16.7 g) is obtained in the form of yellow oil.

bis-(3-Tolyl)acetaldehyde can be obtained in the following way:

A solution of 1,1-bis-(3-tolyl)-2-methoxyethanol (24.66 g) (obtained by reaction of (3-tolyl)magnesium bromide on methyl 2-methoxyacetate in tetrahydrofuran) in formic acid (30 cc) is refluxed for 12 hours, cooled and poured into a mixture of saturated sodium carbonate solution (400 cc) and ethyl acetate (400 cc). The organic phase is washed with water (3×300 cc) and with saturated sodium chloride solution (300 cc), then dried and concentrated to dryness under reduced pressure (2.7 kPa) to give bis-(3-tolyl)acetaldehyde (20.45 g) in the form of a yellow oil.

EXAMPLE 98

A solution of 4,4-diphenylcyclohex-2-en-1-one (25 g) and 1,3,5-tris-trimethylsilylmethyl-1,3,5-triazine (1.65 g) in 1,1,2-trichloroethane (17 cc) is treated with a solution of phenylacetyl fluoride (1.8 g) in 1,1,2-trichloroethane (5 cc) and the mixture is then heated at 120° C. for 22 hours. The reaction mixture is diluted with dichloromethane (100 cc), washed with saturated sodium bicarbonate solution (100 cc) and with saturated sodium chloride solution (100 cc), dried over magnesium sulphate and then concentrated to dryness under reduced pressure (2.7 kPa). The residue is chromatographed on a silica gel column (0.2-0.063 mm, diameter 3 cm, height 27 cm), eluting with a mixture of cyclohexane and ethyl acetate (90/10 by volume) and collecting 35 cc fractions. Fractions 33 to 36 are combined and concentrated to dryness under reduced pressure (2.7 kPa) to give (3aRS,7aRS)-7,7-diphenyl-2-(phenylacetyl)-4-perhydroisoindolone (0.25 g) in the form of white crystals melting at 212° C.

1,3,5-tris-Trimethylsilylmethyl-1,3,5-triazine can be prepared by the method of T. Morimoto, Y. Nezu and K. Achiwa: Chem. Pharm. Bull. 33, 4596 (1985).

Phenylacetyl fluoride can be obtained by the method of G. Olah, S. Kuhn and S. Beke: Chem. Ber. 89, 862, (1956).

EXAMPLE 99

Isopropyl iodide (0.34 cc) and potassium carbonate (0.89 g) are added to a solution of (3aRS,7aRS)-2-[(2-hydroxyphenyl)acetyl]-7,7-diphenyl-4-perhydroisoindolone (1.3 g) in butanone (26 cc) and dimethylformamide (1.3 cc). The mixture is refluxed for 6 hours and then cooled to ambient temperature. The solid is removed by filtration and washed with butanone (2×10 cc). The organic fractions are collected, dried over magnesium sulphate and concentrated under reduced pressure. The residue is chromatographed on a column of silica gel (150 g) eluting with a mixture of cyclohexane and ethyl acetate (80/20 by volume). The residue is taken up in methylene chloride (5 cc) and water (5 cc). The organic phase is decanted, washed with [lacuna] (2×5 cc), dried over sodium sulphate and evaporated under reduced pressure. The residue is crystallized from petroleum ether (b.p. 40° C.-60° C.) (50 cc). The crystals are drained, washed with petroleum ether and dried.

(3aRS,7aRS)-2-[(2-Isopropoxyphenyl)acetyl]-7,7-diphenyl-4-perhydroisoindolone (0.41 g) is obtained in the form of white crystals melting at 177° C.

EXAMPLE 100

(3aRS,7aRS)-2-[(2-Hydroxyphenyl)acetyl]-7,7-diphenyl-4-perhydroisoindolone (2.1 g) is added to a suspension of sodium hydride (0.26 g) (50% dispersion in oil) in toluene (3 cc) and the mixture is stirred for 30 minutes at 50° C. The solution, cooled to 25° C., is treated with a solution of N,N-dimethyl-2-chloroethylamine in dry toluene (4 cc) (obtained by liberation from the corresponding hydrochloride (2.16 g) by the action of caustic potash). The reaction mixture is refluxed for 21 hours and then treated with acetic acid (0.35 cc), diluted with water (20 cc) and ethyl acetate (20 cc). The organic phase is extracted with 0.2N hydrochloric acid (2×30 cc). The acid aqueous phase is washed with ethyl acetate, rendered alkaline by addition of N sodium hydroxide solution (25 cc), and reextracted with ethyl acetate. The organic phase is washed with water until neutral, dried over magnesium sulphate and concentrated to dryness under reduced pressure (2.7 kPa). After chromatographing twice on a column of silica gel (100 g) (0.2-0.045 mm), eluting with a mixture of toluene and diethylamine (90/10 by volume), the expected product (1.3 g) is isolated and is triturated with petroleum ether and dried. (3aRS,7aRS)-2-[(2-(2-dimethylaminoethoxy)-phenyl)acetyl]-7,7-diphenyl-4-perhydroisoindolone (0.47 g) melting at 90° C. is obtained.

EXAMPLE 101

Sodium hydride (0.18 g) (80% dispersion in oil) is added to a solution of (3aRS,7aRS)-2-[(2-hydroxyphenyl)acetyl]-7,7-diphenyl-4-perhydroisoindolone (2.1 g) in toluene (20 cc) and the mixture is stirred for 30 minutes at 20° C. The suspension is treated with a solution of N,N-dimethyl-3-chloropropylamine in dry toluene (20 cc) (obtained by liberation from the corresponding hydrochloride (2.3 g) by the action of caustic potash). The reaction mixture is refluxed for 16 hours and then treated with acetic acid (0.5 cc) and diluted with water (20 cc) and ethyl acetate (50 cc). The organic phase is extracted with 0.2N hydrochloric acid (2×25 cc). The acid aqueous phase is washed with ethyl acetate and filtered and the filtrate is concentrated to dryness under reduced pressure (2.7 kPa). The residue is dissolved in ethyl acetate (20 cc) and treated with a 3M solution (1.2 cc) of hydrochloric acid in dry dioxane. The expected product precipitates in the form of the impure hydrochloride. This yellow solid is redissolved in water and the solution is washed with ethyl acetate, rendered alkaline to pH 10 by the action of 0.1N sodium hydroxide solution and extracted with ethyl acetate. The aqueous phase is extracted with ethyl acetate. This organic phase is dried over magnesium sulphate and concentrated to dryness under reduced pressure (2.7 kPa). The product, obtained in the form of the base, is converted to the hydrochloride by dissolving in ethyl acetate (10 cc) and treating with a 3M solution (0.5 cc) of hydrochloric acid in dry dioxane.

(3aRS,7aRS)-2-[[2-(3-Dimethylaminopropoxy)-phenyl]acetyl]-7,7-diphenyl-4-perhydroisoindolone hydrochloride (0.45 g) is obtained in the form of a yellow solid.

Proton NMR spectrum: 2.05 to 2.35 (Mt, 4H, —CH$_2$— in 5 or 6 and central —CH$_2$— of the 3-dimethylaminopropoxy); 2.65 to 3 (Mt, —CH$_2$— in 6 or 5 and —CH$_2$— in 1); 2.83 (s, —N(CH$_3$)$_2$); 3.2 to 3.4 (Mt, 3H, —CH— in 3a and —N—CH$_2$—); 3.4, 3.65 (Mt, 3H, —N—CO—CH$_2$— and 1H of the —CH$_2$— in 3); 3.9 to 4.5 (Mt, 3H, —CH— in 7a and —O—CH$_2$—); 4.28 (D, J=11 Hz, 1H, 1H of the —CH$_2$— in 3); 6.8 to 7.65 (Mt, 14H, aromatic).

Infrared spectrum (KBr), characteristic bands (cm$^{-1}$): 3600-3250, 3100-3000, 3000-2850, 2750, 2250, 1715, 1640, 1600, 1495, 1475, 1455, 1445, 1440, 1245, 1050, 755, 705.

EXAMPLE 102

(3aRS,7aRS)-2-[(2-hydroxyphenyl)acetyl]-7,7-diphenyl-4-perhydroisoindolone (2.55 g) is added to a suspension of sodium hydride (0.32 g) (50% dispersion in oil) in toluene (10 cc) and, at 25° C., a solution of 1-(4-methyl-1-piperazinyl)-2-chloroethane in dry toluene (10 cc) (obtained by liberation from the corresponding dihydrochloride (1.14 g) by the action of caustic potash) is then added. The reaction mixture is refluxed for 18 hours and then treated with water (20 cc) and ethyl acetate (30 cc). The aqueous phase is extracted with ethyl acetate (10 cc) and the combined organic phases are washed with water until neutral, dried over sodium sulphate and concentrated to dryness under reduced pressure (2.7 kPa). The residue is washed with petroleum ether and then dissolved in a mixture of ethyl acetate and dilute methanesulphonic acid (pH 2). The organic phase is washed with water and the combined acid aqueous phases are washed with ethyl acetate and neutralized by the action of normal sodium hydroxide solution. The neutral phase is extracted with ethyl acetate and the organic phase obtained is then washed with water, dried over sodium sulphate and concentrated to dryness under reduced pressure (2.7 kPa). After chromatography on a column of silica gel (50 g) (0.2–0.045 mm), eluting with a mixture of toluene and diethylamine (90/10 by volume), the expected product (0.6 g) is isolated and is triturated in petroleum ether (15 cc) and dried. (3aRS,7aRS)-2-{2-[2-(4-methyl-1-piperazinyl)ethoxy]phenylacetyl}-7,7-diphenyl-4-perhydroisoindolone (0.36 g) melting at 78° C. is obtained.

1-(4-Methyl-1-piperazinyl)-2-chloroethane dihydrochloride is prepared by the method of G. Emptoz et al., Chim. Thér., 4 (4), 283 (1969).

EXAMPLE 103

Following the procedure of Example 102 and using (3aRS,7aRS)-7,7-diphenyl-2-(2-hydroxyphenylacetyl)-4-perhydroisoindolone and 1-benzyloxy-2-chloroethane as starting materials, (3aRS,7aRS)-7,7-diphenyl-2-{2-[2-(2-hydroxyethoxy)phenyl]acetyl}-4-perhydroisoindolone (0.5 g) is obtained in the form of white crystals melting at 150° C.

EXAMPLE 104

Ethyl phenylacetimidate hydrobromide (1.2 g) and triethylamine (1.4 cc) are added to a stirred suspension of (3aRS,7aRS)-7,7-diphenyl-4-perhydroisoindolone hydrochloride (1.6 g) in 1,2-dichloroethane (40 cc). Stirring of the reaction mixture is continued for 20 hours at ambient temperature and then for 6 hours under reflux. After the temperature has returned to ambient temperature, the reaction mixture is treated with a saturated aqueous solution (50 cc) of potassium carbonate; the organic phase is dried over magnesium sulphate and filtered and the filtrate is concentrated to dryness under reduced pressure (2.7 kPa). The residue is crystallized from acetonitrile (20 cc). The crystals obtained are drained and dried. (3aRS,7aRS)-2-(α-iminophenethyl)-7,7-diphenyl-4-perhydroisoindolone (0.9 g) melting at 195° C. is obtained.

Ethyl phenylacetimidate hydrobromide can be prepared by a method described by D. J. Morgan, Chem. and Ind., 854 (1959).

EXAMPLE 105

Triethyloxonium tetrafluoborate (8.4 g) is added to a stirred suspension of 2-(2-methoxyphenyl)acetamide (6.6 g) in anhydrous dichloromethane (20 cc). Stirring of the reaction mixture is continued for 20 hours at ambient temperature. The mixture is cooled to +5° C. and a solution of (3aR,7aR)-7,7-diphenyl-4-perhydroisoindolone hydrochloride (9.8 g) and triethylamine (10.4 cc) in dichloromethane (60 cc) is then added. After the temperature has returned to ambient temperature, the reaction mixture is refluxed for 4 hours. It is then treated, after the temperature has returned to ambient temperature, with a 10% aqueous potassium carbonate solution (40 cc); the organic phase is washed with distilled water (20 cc), dried over magnesium sulphate and concentrated to dryness under reduced pressure (2.7 kPa). The residue is crystallized from acetonitrile (20 cc); the crystals obtained are drained, washed with acetonitrile (5 cc) and with isopropyl ether (10 cc) and dried. The crystals are recrystallized from acetonitrile (45 cc); the crystals obtained are drained and dried. (3aR,7aR)-2-[1-imino-2-(2-methoxyphenyl)ethyl]-7,7-diphenyl-4-perhydroisoindolone (3.8 g) melting at 191° C. is obtained. $[\alpha]_D^{20} = -255°$ (c=1, methanol).

2-(2-Methoxyphenyl)acetamide can be prepared by the method described by U.S. Seth and S. S. Deshapande, J. Indian Chem. Soc., 27, 429 (1950).

EXAMPLE 106

A suspension of (2-methoxyphenyl)acetamide (0.9 g) in dry dichloromethane (3 cc) is treated with triethyloxonium tetrafluoborate (1.14 g) and the solution obtained is stirred for 20 hours at 25° C. After cooling to 0° C., a solution of 7,7-bis-(3-fluorophenyl)-4-perhydroisoindolone hydrochloride (1.5 g) and triethylamine (1.4 cc) in dichloromethane (9 cc) is added to the reaction mixture. The reaction mixture is stirred for 30 minutes at 25° C., then refluxed for 5 hours and finally stirred for a further 16 hours at 25° C. Saturated potassium carbonate solution (50 cc) is added, the mixture is stirred and filtered and the organic phase is washed with water (2×50 cc). After drying over magnesium sulphate and filtering and concentrating the filtrate to dryness under reduced pressure (2.7 kPa), the residue is chromatographed on an alumina column (diameter 2.6 cm, height 24 cm), eluting under a nitrogen pressure of 0.5 bar with a mixture of 1,2-dichloroethane and methanol (95/5 by volume) and collecting 15 cc fractions. Fractions 7 to 25 are combined and concentrated to dryness under reduced pressure (2.7 kPa) to give (3aRS,7aRS)-7,7-bis-(3-fluorophenyl)-2-[1-imino-2-(2-methoxyphenyl)ethyl]-4-perhydroisoindolone (0.54 g) in the form of a pale yellow meringue.

Proton NMR spectrum (CDCl$_3$): 2.20 and 2.45 (2m, 2H, —CH$_2$— in 5); 2.8 (m, 2H, —CH$_2$— in 6); 3.08 (m, 2H, —CH$_2$— in 1); 3.23 (m, 1H, H in 3a); 3.53 (dd, J=11 and 6.5, 1H, 1H of the —CH$_2$— in 3); 3.6 (s, 2H, —CH$_2$—Ar); 3.8 (m, 1H, H in 7a); 3.8 (s, 3H, OCH$_3$); 4.43 (d, J=11, 1H, 1H of the —CH$_2$— in 3); 6.8 to 7.5 (m, 14H aromatic).

Infrared spectrum (characteristic bands): 3425, 3100–3000, 3000–2850, 2835, 1715, 1592, 1610, 1595, 1460, 1250, 1030, 780, 755, 695.

EXAMPLE 107

Triethyloxonium tetrafluoborate (6.34 g) is added to a stirred suspension of (RS)-2-(2-methoxyphenyl)propionamide (5.4 g) in anhydrous dichloromethane (60 cc). The reaction mixture is stirred for 20 hours. A solution of (3aR,7aR)-7,7-diphenyl-4-perhydroisoindolone hydrochloride (6.65 g) and triethylamine (2.8 cc) in dichloromethane (30 cc) is added. The reaction mixture is refluxed for 5 hours. It is then cooled to +5° C. and is then treated with a 10% aqueous potassium carbonate solution (20 cc). After filtering, the organic phase is washed with distilled water (20 cc), dried over magnesium sulphate and concentrated to dryness under reduced pressure (2.7 kPa). The residue is chromatographed on a neutral alumina column (0.05 mm–0.160 mm, diameter 5 cm, height 20 cm), eluting with a mixture of cyclohexane and ethyl acetate (50/50) and collecting 250 cc fractions. The first fraction is concentrated to dryness under reduced pressure (2.7 kPa). The residue is chromatographed on a silica gel column (0.04 mm–0.06 mm, diameter 2 cm, height 35 cm), eluting with a mixture of n-butanol/acetic acid/pyridine/water (90/4/4/2 by volume) and collecting 20 cc fractions. Fractions 14 to 19 are concentrated to dryness under reduced pressure (0.13 kPa). The residue is taken up in dichloromethane (40 cc) and washed with aqueous potassium carbonate solution (10 cc). The organic phase is dried over magnesium sulphate and concentrated to dryness under reduced pressure (2.7 kPa). The residue is crystallized from diisopropyl ether. The crystals are drained and dried under reduced pressure (0.13 kPa). (3aR,7aR)-2-[1-imino-2-(2-methoxyphenyl)-2-methylethyl]-7,7-diphenyl-4-perhydroisoindolone, form A, (0.12 g) is obtained in the form of a white meringue.

Proton NMR spectrum (CDCl$_3$, 323° K.): 1.34 (D, J=7, 3H); 2.05 to 2.45 (m, 2H, 2H in 5); 2.7 to 3 (m, 4H, 2H in 6 and 2H in 1); 3.2 (m, 1H, 1H in 3a); 3.58 (DD, J=11 and 7, 1H of the —CH$_2$— in 3); 3.7 (S, 3H, —OCH$_3$); 3.75 (m, 1H, H in 7a); 4.04 ((Q, J=7, 1H, Ar—CH—CH$_3$); 4.37 (D, J=11, 1lH, 1H of the —CH$_2$— in 3); 6 6.7 to 7.6 (m, 14H, aromatic).

Infrared spectrum (KBr), characteristic bands (cm$^{-1}$): 3400, 3100–3000, 3000–2850, 2835, 1715, 1595, 1495, 1445, 1245, 1030, 750, 700.

EXAMPLE 108

Following the procedure described above in Example 107 for the preparation of form A, (3aR,7aR)-2-[1-imino-2-(2-methoxyphenyl)-2-methylethyl]-7,7-diphenyl-4-perhydroisoindolone, form B (0.1 g) is obtained in the form of a white meringue from the combined chromatographic fractions 21 to 30.

Proton NMR spectrum (CDCl$_3$, 333° K.): 2.20 (m, 1H, 1H of the —CH$_2$— in 5); 2.45 (m, 1H, 1H of the —CH$_2$— in 5); 2.8 (m, 2H, —CH$_2$— in 6); 3.08 (m, 2H, —CH$_2$— in 1); 3.23 (m, 1H, 1H in 3a); 3.53 (DD, J=11 and 6.5, 1H, 1H of the —CH$_2$— in 3); 3.6 (S, 3H, —OCH$_3$); 4.43 (D, J=11, 1H, 1H in 7a); 3.8 (S, 3H, —OCH$_3$—); 4.43 (D, J=11, 1H of the —CH$_2$— in 3); 6.8 to 7.5 (m, 14H, aromatic).

Infrared spectrum (KBr): bands identical to those for form A.

(RS)-2-(2-Methoxyphenyl)propionamide can be prepared in the following way:

N,N'-Carbonyldiimidazole (16.2 g) is added to a solution of 2-(2-methoxyphenyl)propionic acid (17.5 g) in dry dichloromethane (200 cc), cooled to +5° C. The mixture is stirred for 30 minutes at +5° C. and a stream of ammonia is then passed into the solution for 1 hour, maintaining the same temperature. After stirring for 2 hours at 20° C., the reaction mixture is washed with water (200 cc), dried over magnesium sulphate and then concentrated to dryness under reduced pressure (2.7 kPa). The residue is crystallized from isopropyl ether and the crystals are drained and dried under reduced pressure (2.7 kPa). (RS)-2-(2-Methoxyphenyl)propionamide (12.1 g) is obtained in the form of a white solid melting at 138° C.

(RS)-2-(2-Methoxyphenyl)propionic acid can be prepared in the following way:

A 1.6M solution (20 cc) of n-butyllithium in tetrahydrofuran is added in the course of 20 minutes to a solution of diisopropylamine (45.5 cc) in tetrahydrofuran (250 cc), cooled to +10° C. After stirring for 10 minutes, the mixture is brought to 0° C. and a solution of 2-(2-methoxyphenyl)acetic acid in tetrahydrofuran (100 cc) is added in the course of 20 minutes. After 30 minutes at 35° C., methyl iodide (10 cc) is added and the mixture is stirred for 1 hour at 35° C. Water (150 cc) is added to the reaction mixture and the resulting mixture is diluted with ethyl acetate. The aqueous phase is separated off, acidified with 4N hydrochloric acid and then extracted with ethyl acetate (2×100 cc). The organic phase is dried over magnesium sulphate and concentrated to dryness under reduced pressure (2.7 kPa). The residue is crystallized from isopropyl ether (100 cc) and the crystals are drained and dried under reduced pressure (2.7 kPa).

(RS)-2-(2-Methoxyphenyl)propionic acid (17.5 g) is obtained in the form of a white solid melting at 108° C.

EXAMPLE 109

Triethoxyloxonium tetrafluoroborate (4 g) is added to a stirred solution of N-(2-thienyl)methyl-2-(2-methoxyphenyl)acetamide (5.2 g) in anhydrous dichloromethane (50 cc). Stirring of the reaction mixture is continued for 7 hours, at ambient temperature. The mixture is cooled to +5° C. and a solution of (3aR,7aR)-7,7-diphenyl-4-perhydroisoindolone hydrochloride (4.6 g) and triethylamine (5 cc) in dichloromethane (50 cc) is then added. Stirring of the reaction mixture is then continued for 20 hours at ambient temperature and the reaction mixture is then refluxed for 1 hour. It is then treated, after the temperature has returned to ambient temperature, with a 10% aqueous potassium carbonate solution (100 cc); the organic phase is washed with distilled water (40 cc), dried over magnesium sulphate and concentrated to dryness under reduced pressure (2.7 kPa). The residue is chromatographed on a Péchiney CBT1 neutral alumina gel column (diameter 5 cm, height 40 cm), eluting with a mixture of cyclohexane and ethyl acetate (50/50 by volume) and collecting 100 cc fractions. Fractions 4 to 13 are combined and concentrated to dryness under reduced pressure (2.7 kPa). The residue is crystallized from isopropanol (20 cc); the crystals obtained are drained, washed with isopropyl ether (10 cc) and dried. (3aR,7aR)-2-[2-(2-methoxyphenyl)-1-(2-thienylmethyl)iminoethyl]-7,7-diphenyl-4-perhydroisoindolone (1.9 g) melting at 88° C. is obtained; $[\alpha]_D^{20} = -170°$ (c=1, methanol).

N-(2-Thienyl)methyl-2-(2-methoxyphenyl)acetamide can be prepared in the following way:

N,N'-Carbonyldiimidazole (8.1 g) is added to a stirred solution of 2-(2-methoxyphenyl)acetic acid (8.3 g) in anhydrous dichloromethane (80 cc), cooled to +5° C.; stirring of the reaction mixture is continued for 1 hour and a half and (2-thienyl)methylamine (5.1 cc) is then added. Stirring of the reaction mixture is continued for 1 hour at +5° C. and then for 2 hours at ambient temperature. The reaction mixture is then washed with distilled water (2×40 cc); the organic solution is dried over magnesium sulphate and concentrated to dryness under reduced pressure (2.7 kPa). The solid residue obtained is washed with isopropyl ether (30 cc), drained and dried. N-(2-Thienyl)methyl-2-(2-methoxyphenyl)acetamide (10.5 g) melting at 84° C. is obtained.

EXAMPLES 110 TO 136

Carrying out the procedure as described in Example 4 and using (3aRS,7aRS)- or (3aR,7aR)-7,7-diphenyl-2-phenylacetyl-4-perhydroisoindolone, (3aRS,7aRS)-7,7-diphenyl-2-(2-fluorophenyl)acetyl-4-perhydroisoindolone or (3aRS,7aRS)- or (3aR,7aR)-7,7-diphenyl-2-(2-methoxyphenyl)acetyl-4-perhydroisoindolone as the starting material, the following products are prepared:

| Example No. | R3 | Form | Melting point | Yield % | Infrared spectrum |
|---|---|---|---|---|---|
| 110 | —CH$_2$—C$_6$H$_5$ p-CH$_3$ | (3aRS, 7aRS) | 182° C. | 63 | |
| 111 | —(CH$_2$)$_2$—N(CH$_3$)$_2$ | (3aRS, 7aRS) | 147° C. | 53 | |
| 112 | —CH$_2$—(imidazole) | (3aRS, 7aRS) | 143° C. | 50 | |
| 113 | —(CH$_2$)$_6$—N(CH$_3$)CH$_2$C$_6$H$_5$ | (3aRS, 7aRS) | 172° C. | 56 | |
| 114 | —(CH$_2$)$_6$—N(CH$_3$)$_2$ | (3aRS, 7aRS) | 104° C. | 5.6 | |
| 115 | —CH$_2$—CON(CH$_3$)—(CH$_2$)$_2$—N(CH$_3$)$_2$ | (3aRS, 7aRS) | 75° C. | 58 | |
| 116 | —(CH$_2$)$_5$—CONH$_2$ | (3aRS, 7aRS) | 174° C. | 48 | |
| 117 | —(CH$_2$)$_5$—COO(CH$_2$)$_2$—N(CH$_3$)$_2$ | (3aRS, 7aRS) | 102° C. | 6.8 | |
| 118 | —(CH$_2$)$_5$—CON(CH$_3$)$_2$ | (3aRS, 7aRS) | 130° C. | 27 | |
| 119 | —(CH$_2$)$_4$—N(CH$_3$)$_2$ | (3aRS, 7aRS) | 134° C. | 32.5 | |
| 120 | —(CH$_2$)$_5$—N(CH$_3$)$_2$ | (3aRS, 7aRS) | 112° C. | 28.6 | |
| 121 | —(CH$_2$)$_4$—NHCOCH$_3$ | (3aRS, 7aRS) | 114° C. | 20.2 | |
| 122 | —(CH$_2$)$_3$—NHCOCH$_3$ | (3aRS, 7aRS) | 180° C. | 20 | |
| 123 | —(CH$_2$)$_8$—NHCOCH$_3$ | (3aRS, 7aRS) | | 26 | 3300 cm$^{-1}$ ν NH; 3100–3000 cm$^{-1}$ ν CH aromatic; 2925 cm$^{-1}$ ν$_a$ CH$_2$; 2850 cm$^{-1}$ ν$_s$ CH$_2$; 1715 cm$^{-1}$ ν C=O ketone; 1655 cm$^{-1}$ ν C=O amide; 1600; 1585; 1495; 1445 cm$^{-1}$ aromatic rings; 1550 cm$^{-1}$ δ NH; 750; 700 cm$^{-1}$ γ CH |
| 124 | —(CH$_2$)$_{10}$—NHCOCH$_3$ | (3aRS, 7aRS) | | 14.5 | 3400 cm$^{-1}$ ν NH; 3100–3000 cm$^{-1}$ ν CH aromatic; 2925 cm$^{-1}$ ν$_a$ CH$_2$; 2850 cm$^{-1}$ ν$_s$ CH$_2$; 1715 cm$^{-1}$ ν C=O ketone; 1650 cm$^{-1}$ ν C=O amide; 1620 cm$^{-1}$ ν C=N; 1600; 1580; 1495; 1450 cm$^{-1}$ aromatic rings; 1550 cm$^{-1}$ δ NH; 750; 700 cm$^{-1}$ γ CH |
| 125 | —(CH$_2$)$_{12}$—NHCOCH$_3$ | (3aRS, 7aRS) | | 30 | 3300 cm$^{-1}$ ν NH; 3100–3000 cm$^{-1}$ ν CH aromatic; 2925 cm$^{-1}$ ν$_a$ CH$_2$; 2850 cm$^{-1}$ ν$_s$ CH$_2$; 1715 cm$^{-1}$ ν C=O ketone; 1655 cm$^{-1}$ ν C=O amide; 1600; 1585; 1495; 1455 cm$^{-1}$ aromatic rings; 1550 cm$^{-1}$ δ NH; 750; 700 cm$^{-1}$ γ CH |
| 126 | —(CH$_2$)$_6$—NHCOOC(CH$_3$)$_3$ | (3aRS, 7aRS) | | 79.8 | 3500–2250 cm$^{-1}$ ν OH + ν NH + ν N$^+$H; 3100–3000 cm$^{-1}$ ν CH aromatic; 3000–2850 cm$^{-1}$ ν$_a$ + ν$_s$ CH$_2$ + CH$_3$; 1715 cm$^{-1}$ ν C=O ketone + carbamate; 1640 cm$^{-1}$ ν C=N + ν$_a$ C=O carboxylate; 1600; 1585; 1495; 1445 cm$^{-1}$ aromatic rings; 1510 cm$^{-1}$ δ NH; 1235 cm$^{-1}$ ν CO phenols; 1165 cm$^{-1}$ ν CO carbamate; 750; 700 cm$^{-1}$ γ CH |
| 127 | —(CH$_2$)$_6$—NHCHO | (3aRS, 7aRS) | | 46.5 | 3240 cm$^{-1}$ ν NH; 3100–3000 cm$^{-1}$ ν CH aromatic; 3000–2825 cm$^{-1}$ ν$_a$ + ν$_s$ CH$_2$ |

-continued

| Example No. | R3 | Form | Melting point | Yield % | Infrared spectrum | |
|---|---|---|---|---|---|---|
| | | | | | 1710 cm$^{-1}$ | $\nu$ C=O ketone |
| | | | | | 1670 cm$^{-1}$ | $\nu$ C=O amide |
| | | | | | 1610 cm$^{-1}$ | $\nu$ C=N |
| | | | | | 1595; 1580; 1495; 1445 cm$^{-1}$ aromatic rings | |
| | | | | | 750; 700 cm$^{-1}$ | $\gamma$ CH |
| 128 | —(CH$_2$)$_4$—CON(CH$_3$)$_2$ | (3aRS, 7aRS) | | 34.8 | 3100–3000 cm$^{-1}$ | $\nu$ CH aromatic |
| | | | | | 3000–2825 cm$^{-1}$ | $\nu_a + \nu_s$ CH$_2$ + CH$_3$ |
| | | | | | 1715 cm$^{-1}$ | $\nu$ C=O ketone |
| | | | | | 1645 cm$^{-1}$ | $\nu$ C=O amide |
| | | | | | 1615 cm$^{-1}$ | $\nu$ C=N |
| | | | | | 1580; 1495; 1445 cm$^{-1}$ aromatic rings | |
| | | | | | 750; 700 cm$^{-1}$ | $\gamma$ CH |
| 129 | —CH(C$_6$H$_5$)—CON(CH$_3$)—(CH$_2$)$_2$—N(CH$_3$)$_2$(S) | (3aR, 7aR) | | 35 | 3100–3000 cm$^{-1}$ | $\nu$ CH aromatic |
| | | | | | 3000–2850 cm$^{-1}$ | $\nu_a + \nu_s$ CH$_2$ + CH$_3$ |
| | | | | | 2825; 2770 cm$^{-1}$ | $\nu$ CH N(CH$_3$)$_2$ |
| | | | | | 1715 cm$^{-1}$ | $\nu$ C=O ketone |
| | | | | | 1635 cm$^{-1}$ | $\nu$ C=O amide |
| | | | | | 1605 cm$^{-1}$ | $\nu$ C=N |
| | | | | | 1580; 1495; 1445 cm$^{-1}$ aromatic rings | |
| | | | | | 750; 700 cm$^{-1}$ | $\gamma$ CH |

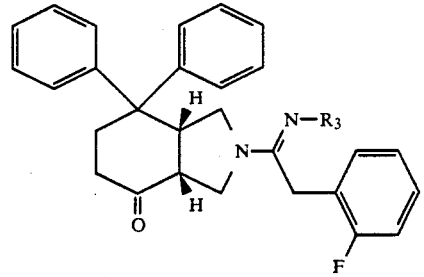

| 130 | —CH$_2$—C$_6$H$_5$ | (3aRS, 7aRS) | 162° C. | 27 |
| 131 | —H | (3aRS, 7aRS) | 170° C. | 10 |

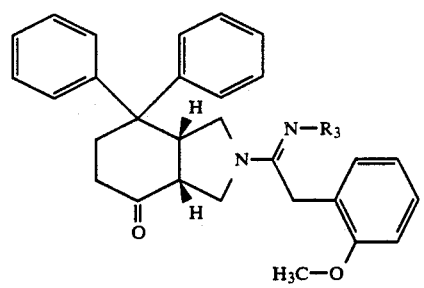

| 132 | —CH$_2$—C$_6$H$_5$ | (3aR, 7aR) | 110° C. | 24 | | |
| 133 | 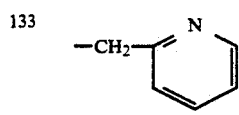 | (3aR, 7aR) | 168° C. | 9 | | |
| 134 | —(CH$_2$)$_6$—NHCOCH$_3$ | (3aRS, 7aRS) | 152° C. | 17.2 | | |
| 135 | —CH$_2$—CON(CH$_3$)—(CH$_2$)N(CH$_3$)$_2$ | (3aRS, 7aRS) | | 47 | 3100–3000 cm$^{-1}$ | $\nu$ CH aromatic |
| | | | | | 3000–2750 cm$^{-1}$ | $\nu_a + \nu_s$ CH$_2$ + CH$_3$ |
| | | | | | 2835 cm$^{-1}$ | $\nu$ CH$_3$ O—CH$_3$ |
| | | | | | 1715 cm$^{-1}$ | $\nu$ C=O ketone |
| | | | | | 1640 cm$^{-1}$ | $\nu$ C=O amide |
| | | | | | 1610 cm$^{-1}$ | $\nu$ C=N |
| | | | | | 1495 cm$^{-1}$ | aromatic rings |
| | | | | | 1245 cm$^{-1}$ | $\nu_a$ CO ether |
| | | | | | 1030 cm$^{-1}$ | $\nu_s$ CO ether |
| | | | | | 755–750 cm$^{-1}$ | $\gamma$ CH |

-continued

| Example No. | R3 | Form | Melting point | Yield % | Infrared spectrum | |
|---|---|---|---|---|---|---|
| 136 | —CH—C$_6$H$_5$ (S)<br>    \|<br>   COOH | (3aR, 7aR) | | 4.8 | 3100–3000 cm$^{-1}$<br>3000–2850 cm$^{-1}$<br>2840 cm$^{-1}$<br>1715 cm$^{-1}$<br>1625 cm$^{-1}$<br><br>1495; 1450 cm$^{-1}$<br><br>1350 cm$^{-1}$<br><br>1250 cm$^{-1}$<br>1025 cm$^{-1}$<br>750; 730; 700 cm$^{-1}$ | $\nu$ CH aromatic<br>$\nu_a + \nu_s$ CH$_2$<br>$\nu$ CH $\phi$-O—CH$_3$<br>$\nu$ C=O ketone<br>$\nu$ C=N + $\nu$ C=O<br>carboxylate<br>aromatic<br>rings<br>$\nu_s$ C=O<br>carboxylate<br>$\nu_a$ CO ether<br>$\nu_s$ CO ether<br>$\gamma$ CH |

EXAMPLE 137

Carrying out the procedure as described in Example 104, using (3aR,7aR)-7,7-diphenyl-4-perhydroisoindolone hydrochloride as the starting material, (3aR,7aR)-7,7-diphenyl-2-[1-imino-2-(2-dimethylaminophenyl)ethyl]-4-perhydroisoindolone melting at 188° C. is obtained in a yield of 55%.

The present invention also relates to the pharmaceutical compositions consisting of a product of general formula (I), or a salt where such exist, optionally in combination with any other pharmaceutically compatible product, which can be inert or physiologically active. The compositions according to the invention can be administered parenterally, orally or rectally or applied topically.

The sterile compositions for parenteral administration which can be used, in particular, in the form of perfusions are preferably aqueous or non-aqueous solutions or suspensions or emulsions. The solvent or vehicle used can be water, propylene glycol, a polyethylene glycol, vegetable oils, in particular olive oil, injectable organic esters, for example ethyl oleate, or other suitable organic solvents. These compositions may also contain adjuvants, in particular wetting agents, agents for rendering isotonic, emulsifiers, dispersants and stabilizers. Sterilization can be effected in various ways, for example by aseptizing filtration, by incorporating sterilizing agents into the composition, by irradiation or by heating. They may also be prepared in the form of sterile solid compositions which can be dissolved at the time of use in an injectable sterile medium.

The compositions for rectal administration are suppositories or rectal capsules which contain, in addition to the active product, excipients such as cacao butter, semi-synthetic glycerides or polyethylene glycols.

Solid compositions for oral administration which can be used are tablets, pills, powders or granules. In these compositions, the active product according to the invention (optionally in combination with another pharmaceutically compatible product) is mixed with one or more inert diluents or adjuvants, such as sucrose, lactose or starch. These compositions may also comprise substances other than the diluents, for example a lubricant, such as magnesium stearate.

Liquid compositions for oral administration which can be used are pharmaceutically acceptable emulsions or solutions, suspensions, syrups and elixirs containing inert diluents such as water or paraffin oil. These compositions may also comprise substances other than the diluents, for example wetting agents, sweeteners or flavorings.

The compositions for topical application can be, for example, creams, ointments or lotions.

In human therapy the products according to the invention can be particularly useful in the treatment of pain of traumatic, post-surgical, menstrual or cephalic origin, in the treatment of anxiety, psychoses, Parkinson's disease, schizophrenia or Alzheimer's disease, in muscle-relaxing treatments, in the treatment of spasmodic, painful and inflammatory occurrences in the digestive tracts (ulcerous colites, irritable colon syndrome, Crohn's disease), of the urinary tract (cystites) and of the respiratory tract (asthma, rhinites) or in gynaecology and in the treatment of migraine. The new isoindolone derivatives are also useful in the treatment of rheumatoid arthritis and in disorders due to disturbance of the immune system, in the treatment of inflammation in dermatology, such as psoriasis, herpes, urticarias, eczemas and photodermates, and in occular and dental inflammatory disorders.

The products according to the invention can also find application in the treatment of cardiovascular disorders, such as hypotension.

The dosages depend on the desired effect and on the duration of the treatment. For an adult, they are generally between 0.25 and 1500 mg per day taken at intervals.

In general, the physician will determine the posology, which he estimates most appropriately as a function of the age, the body weight and all of the other factors inherent to the subject to be treated.

The following example, which is given without any restriction being implied, illustrates a composition according to the invention.

EXAMPLE

Using the customary technique, active product tablets having the following composition are prepared:

| | |
|---|---|
| (3aR,7aR)-2-[1-imino-2-(2-methoxyphenyl)-ethyl]-7,7-diphenyl-4-perhydroisoindolone | 25 mg |
| starch | 83 mg |
| silica | 30 mg |
| magnesium stearate | 3 mg |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:
1. An isoindolone derivative comprising the formula:

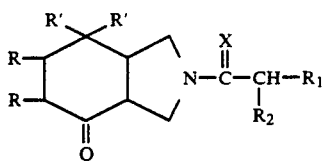

in which
the radicals R are identical and are selected from a group consisting of hydrogen atoms or together form a bond,
the symbols R' are identical and are selected from a group consisting of phenyl or phenyl moieties optionally substituted by a halogen atom or by a methyl radical in position 2 or 3,
the symbol X is selected from the group consisting of an oxygen or sulphur atom or a radical N-$R_3$, for which $R_3$ is a hydrogen atom or an alkyl radical containing 1 to 12 carbon atoms and optionally substituted from a group consisting of at least one carboxyl, dialkylamino, acylamino, alkoxycarbonyl, alkoxy-carbonylamino, carbamoyl, alkylcarbamoyl or dialkylcarbamoyl radicals, the alkyl portions of these radicals being able themselves to carry a dialkylamino or phenyl substituent, or substituted from a group consisting of phenyl, substituted phenyl, substituted by halogen, alkyl, alkoxy or dialkylamino, naphthyl, thienyl, furyl, pyridyl or imidazolyl radicals or a dialkylamino radical,
the symbol $R_1$ is selected from the group consisting of an unsubstituted phenyl radical or substituted phenyl radical wherein the phenyl substituents are selected from the group consisting of at least one halogen atom, hydroxyl, unsubstituted or substituted alkyl radicals, unsubstituted or substituted alkoxy or alkylthio radicals, amino, alkylamino, or dialkylamino radicals in which the alkyl parts can form, with the nitrogen atom to which they are attached, a 5- to 6-membered heterocycle which can contain another hetero-atom selected from the group consisting of oxygen, sulphur or nitrogen, and heterocycle being unsubstituted or substituted by an alkyl radical, or a cyclohexadienyl or naphthyl radical or a saturated or unsaturated monocyclic or polycyclic heterocycle containing 5 to 9 carbon atoms and at least one hetero-atom selected from the group consisting of oxygen, nitrogen or sulphur, and
the symbol $R_2$ is selected from the group consisting of a hydrogen or halogen atom or a hydroxyl, alkyl, aminoalkyl, alkylaminoalkyl, dialkylaminoalkyl, alkoxy, alkylthio, acyloxy, carboxyl, alkoxycarbonyl, dialkylaminoalkoxycarbonyl, benzyloxycarbonyl, amino, acylamino or alkoxycarbonylamino radical, the abovementioned alkyl and acyl radicals being straight-chain or branched and containing 1 to 4 carbon atoms, in its 3aR,7aR or 3aRS,7aRS forms or their mixtures or salts where such exist.

2. The isoindolone derivative according to claim 1, wherein:
the radicals R are identical and are selected from the group consisting of hydrogen atoms or together form a bond,
the symbols R' are identical and are selected from the group consisting of phenyl radicals optionally substituted by a fluorine or chlorine atom or by a methyl radical in position 2 or 3,
the symbol X is selected from the group consisting of an oxygen or sulphur atom or a radical N-$R_3$ for which $R_3$ is a hydrogen atom, or an alkyl radical containing 1 to 12 carbon atoms and optionally substituted from the group consisting of at least one carboxyl, dialkylamino, acylamino, alkoxycarbonyl, alkoxycarbonylamino, carbamoyl, alkylcarbamoyl or dialkylcarbamoyl radicals, the alkyl portions of these radicals being able themselves to carry a dialkylamino or phenyl substituent, or substituted from a group consisting of phenyl, substituted phenyl, substituted by a fluorine or chlorine atom or by an alkyl, alkoxy or dialkylamino radical, naphthyl, 2-thienyl, 2-furyl, pyridyl or imidazolyl radicals or a dialkylamino radical,
the symbol $R_1$ is selected from the group consisting of a phenyl radical or substituted phenyl radical wherein the phenyl substituents are selected from the group consisting of at least one fluorine, chlorine or bromine atoms, hydroxyl radicals, unsubstituted or substituted alkyl radicals, unsubstituted or substituted alkoxy or alkylthio radicals, amino, alkylamino or dialkylamino radicals, in which the alkyl parts can form, with the nitrogen atom to which they are attached, a saturated 5- or 6-membered heterocycle, which can also contain another oxygen atom, or a cyclohexadienyl or naphthyl radical or a saturated or unsaturated monocyclic or polycyclic heterocyclic radical containing 5 to 9 carbon atoms and at least one hetero-atom selected from the group consisting of nitrogen or sulphur, and
the symbol $R_2$ represents a hydrogen or fluorine atom or a hydroxyl, alkyl, aminoalkyl, alkylaminoalkyl, dialkylaminoalkyl, alkoxy, alkylthio, acyloxy, carboxyl, alkoxycarbonyl, dialkylaminoalkoxycarbonyl, benzyloxycarbonyl, amino, acylamino or alkoxycarbonylamino radical, the abovementioned alkyl and acyl radicals being straight-chain or branched and containing 1 to 4 carbon atoms, in its 3aR,7aR or 3aRS,7aRS forms or their mixtures as well as its salts where such exist.

3. 2-[1-Imino-2-(2-methoxyphenyl)ethyl]-7,7-diphenyl-4-perhydroisoindolone in its 3aR,7aR or 3aRS,7aRS forms as well as its salts.

4. 7,7-Diphenyl-2-[2-(2-dimethylaminophenyl)acetyl]-4-perhydroisoindolone in its 3aR,7aR or 3aRS,7aRS forms as well as its salts.

5. 7,7-Diphenyl-2-[(R)-2-(2-methoxyphenyl)-propionyl]-4-perhydroisoindolone in its 3aR,7aR or 3aRS,7aRS forms.

6. 2-{[2-(3-Dimethylaminopropoxy)phenyl]acetyl}-7,7-diphenyl-4-perhydroisoindolone in its 3aR,7aR or 3aRS,7aRS forms as well as its salts.

7. 2-[(S)-1-Carboxybenzylimino-2-(2-methoxyphenyl)ethyl]-7,7-diphenyl-4-perhydroisoindolone in its 3aR,7aR or 3aRS,7aRS forms as well as its salts.

8. A process for the preparation of an isoindolone derivative according to claim 1, wherein an acid or a reactive derivative of the acid of formula

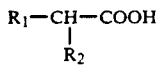

in which $R_1$ and $R_2$ are defined as in claim 1, to act on an isoindolone derivative of formula

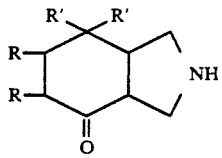

in which the symbols R are defined as in claim 1, and, optionally, then converting the amide obtained to a thioamide or to an amidine for which X represents a radical $N-R_3$, $R_3$ being defined as above in claim 1, and, optionally, the product obtained is converted to a salt where such exist.

9. A process for the preparation of an isoindolone derivative according to claim 1, wherein $R_2$ is defined as in claim 1, with the exception of representing or carrying hydroxyl, amino, alkylamino, dialkylamino or carboxyl substituents, and R, R', $R_3$ and X are defined as in claim 1, comprising allowing 1,3,5-tris-trimethylsilylmethyl-1,3,5-triazine and an acid fluoride of formula

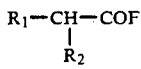

in which $R_1$ and $R_2$ are defined as above, to act on a cyclohexenone derivative of formula

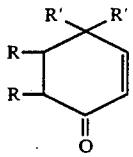

in which R and R' are defined as in claim 1, and, optionally, then converting the amide obtained to a thioamide or to an amidine for which X is a radical $N-R_3$, $R_3$ being defined as in claim 1.

10. A process for the preparation of an isoindolone derivative according to claim 1, wherein the symbol $R_1$ represents an alkoxyphenyl radical, the symbol $R_2$ is other than a hydroxyl radical and the symbols R, R', $R_3$ and X are defined as in claim 1, comprising, allowing a halogenated derivative of formula $R_4$-Hal in which $R_4$ is an alkyl radical optionally substituted by a protected hydroxyl radical or dialkylamino in which the alkyl parts can optionally form, with the nitrogen atom to which they are attached, a heterocycle as defined in claim 1, and Hal is a halogen atom, to act on an isoindolone derivative according to claim 1, for which $R_1$ is a hydroxyphenyl radical, and, optionally, then removing the hydroxyl protective radical.

11. A process for the preparation of an isoindolone derivative according to claim 1, wherein X is a radical $N-R_3$ and the symbols R, R', $R_1$, $R_2$ and $R_3$ are defined as in claim 1, comprising allowing a product of formula:

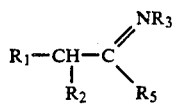

optionally in the form of a salt, in which $R_1$, $R_2$ and $R_3$ are defined as in claim 1 and $R_5$ is selected form a group consisting of a straight-chain or branched alkoxy radical containing 1 to 4 carbon atoms or a methylthio, ethylthio, benzylthio or alkoxycarbonylmethylthio radical or, if $R_3$ is other than a hydrogen atom, $R_5$ is select from a group consisting of an acyloxy radical containing 1 to 4 carbon atoms or a chlorine atom, to act on an isoindolone derivative of formula:

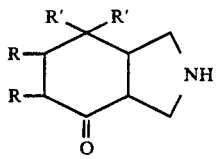

in which R is defined as in claim 1, and, optionally, then converting the product to a salt, if such exists.

12. A pharmaceutical composition therapeutically useful with a substance P antagonist to be administered orally or rectally, topically, or parenterally, comprising an effective an effective amount of at least one compound of claim 1 as a substance P inhibitor in the pure state as a pharmaceutically-acceptable salt, with pharmaceutically-acceptable carriers or diluents.

13. The isoindolone derivative according to claim 1, wherein the alkyl radical is substituted by halogen atoms or amino, alkylamino or dialkylamino radicals.

14. The isoindolone derivative according to claim 1, wherein the alkoxy or alkylthio radicals are substituted by hydroxyl or dialkylamino radicals in which the alkyl parts form, with the nitrogen atom to which they are attached, a 5- to 6-membered heterocycle which can contain another hetero-atom selected from the group consisting of oxygen, sulphur or nitrogen, said heterocycle being unsubstituted or substituted by an alkyl radical.

15. The isoindolone derivative according to claim 2, wherein the alkyl radical is substituted by halogen or amino radicals.

16. The isoindolone derivative according to claim 2, wherein the alkoxy or alkylthio radicals are substituted by hydroxyl or dialkylamino radicals in which the alkyl parts form, with the nitrogen atom to which they are attached, a 6-membered heterocycle which can contain a nitrogen atom, said heterocycle being unsubstituted or substituted by an alkyl radical.

* * * * *